US011672786B2

(12) United States Patent
Pearson et al.

(10) Patent No.: US 11,672,786 B2
(45) Date of Patent: Jun. 13, 2023

(54) METHODS OF TREATING DISEASES ASSOCIATED WITH REPEAT INSTABILITY

(71) Applicants: The Hospital for Sick Children, Toronto (CA); Osaka University, Osaka (JP)

(72) Inventors: Christopher E. Pearson, Toronto (CA); Masayuki Nakamori, Osaka (JP); Kazuhiko Nakatani, Osaka (JP)

(73) Assignees: The Hospital for Sick Children; Osaka University, Osaka (JP)

( * ) Notice: Subject to any disclaimer, the term of this patent is extended or adjusted under 35 U.S.C. 154(b) by 842 days.

(21) Appl. No.: 16/325,066

(22) PCT Filed: Aug. 12, 2017

(86) PCT No.: PCT/IB2017/054932
§ 371 (c)(1),
(2) Date: Feb. 12, 2019

(87) PCT Pub. No.: WO2018/029660
PCT Pub. Date: Feb. 15, 2018

(65) Prior Publication Data
US 2021/0283114 A1    Sep. 16, 2021

Related U.S. Application Data

(60) Provisional application No. 62/374,072, filed on Aug. 12, 2016.

(51) Int. Cl.
*A61K 31/4375* (2006.01)
*A61P 25/28* (2006.01)
*A61K 9/00* (2006.01)
*A61K 9/127* (2006.01)

(52) U.S. Cl.
CPC ........ *A61K 31/4375* (2013.01); *A61K 9/0019* (2013.01); *A61K 9/127* (2013.01); *A61P 25/28* (2018.01)

(58) Field of Classification Search
CPC ........ A61K 31/4375; A61K 9/00; A61P 25/28
See application file for complete search history.

(56) References Cited

U.S. PATENT DOCUMENTS

2010/0184833 A1    7/2010  De Kimpe et al.

FOREIGN PATENT DOCUMENTS

| WO | WO 2011/016840 |   | 2/2011 | |
|---|---|---|---|---|
| WO | WO-2011016840 | * | 2/2011 | |
| WO | WO-2011016840 A2 | * | 2/2011 | ............. A61P 43/00 |

OTHER PUBLICATIONS

Jinxing-Li et al. Naphthyridine-Benzoazaquinolone: Evaluation of a Tricyclic system for the binding to (CAG) Repeat DNA and RNA, Chem. Asian Journal 2106, 11(13),1971-1981. (Year: 2016).*
Jinxing Li et al. Naphthyridine-Benzoazaquinolone: Evaluation of a Tricyclic System for the Binding to (CAG0n Repeat DNA and RNA, Chem. Asian J. (Year: 2016).*
Sakata, "Development of naphthyridine-azaquinolone derivative targeting CAG repeat DNA and RNA, and its inhibitory effect on transcription and translation," Proceedings of the 136th Annual Meeting of the Pharmaceutical Society of Japan, Mar. 26-29, 2016, 28S-am01S.
JP Notice of Rejection in Japanese Appln. No. 2019-529315, dated Jul. 21, 2021, 10 pages (with English translation).
Cummings and Zoghbi, "Trinucleotide Repeats: Mechanisms and Pathophysiology," Annual Review of Genomics and Human Genetics, 2000, 1:281-328.
Abeliovich et al, "Negative Expansion of the Myotonic Dystrophy Unstable Sequence," Am. J. Hum. Genet., 1993, 52:1175-1181.
Anvret et al, "Larger expansions of the CTG repeat in muscle compared to lymphocytes from patients with myotonic dystrophy," Hum. Mol. Genet., 1993, 2:1397-1400.
Aoki et al, "Reduction of CAG expansions in cerebellar cortex and spinal cord of DRPLA," Clin. Genet., 1996, 50:199-201.
Axford et al, "Detection of Slipped-DNAs at the Trinucleotide Repeats of the Myotonic Dystrophy Type I Disease Locus in Patient Tissues," PLos Genet., 2013, 9:e1003866, 13 pages.
Barbe et al, "CpG Methylation, a Parent-of-Origin Effect for Maternal-Biased Transmission of Congenital Myotonic Dystrophy," The American Journal of Human Genetics, 2017, 488-505.
Barcelo et al, "Removal of DNA Curving by DNA Ligands: Gel Electrophoresis Study," Biochem., 1991, 30:4863-4873.
Bernat et al, "RNA Structures as Mediators of Neurological Diseases and as Drug Target," Neuron, 2015, 87:28-46.
Brook et al., "Molecular basis of myotonic dystrophy: Expansion of a trinucleotide (CTG) repeat at the 3' end of a transcript encoding a protein kinase family member," 1992, Cell, 68:799-808.
Cancel et al, "Somatic mosaicism of the CAG repeat expansion in spinocerebellar ataxia type 3/Machado-Joseph disease," Hum. Mutat., 1998, 11:23-27.
Carlsson et al, "Double bands in DNA gel electrophoresis caused by bis-intercalating dyes," Nuc. Acids Res., 1995, 23:2413-2420.
Castel et al, "Expanded CTG repeat demarcates a boundary for abnormal CpG methylation in myotonic dystrophy patient tissues," Hum. Mol. Genet., 2011, 20:1-15.
Castel et al., "Repeat instability as the basis for human diseases and as a potential target for therapy," Nature Reviews, Mol. Cell. Biol., 2010, 11:165-170.
Cleary & Pearson, "The contribution of cis-elements to disease-associated repeat instability: clinical and experimental evidence," Cytogenet. Genome Res., 2003, 100:25-55.

(Continued)

*Primary Examiner* — Johann R Richter
*Assistant Examiner* — Jagadishwar R Samala
(74) *Attorney, Agent, or Firm* — Fish & Richardson P.C.

(57) ABSTRACT

Methods of treating diseases caused by repeat DNA instability are described herein. The methods described herein can inhibit the further expansion of repeat DNA and, in some instances, reduce the size of the repeat DNA (e.g., reduce the number of repeats).

7 Claims, 45 Drawing Sheets

Specification includes a Sequence Listing.

(56) References Cited

OTHER PUBLICATIONS

Cleary et al, "Evidence of cis-acting factors in replication-mediated trinucleotide repeat instability in primate cells," Nat. Genetics, 2002, 31:37-46.
De Rooij et al, "Somatic expansion of the (CAG)n repeat in Huntington disease brains," Hum. Genet., 1995, 95:270-274.
Dietmaier et al., "Diagnostic Microsatellite Instability: Definition and Correlation with Mismatch Repair Protein Expression," 1997, Cancer Res., 57:4749-4756.
Fox & Woolley, "The strong binding of luzopeptin to DNA," Biochem. Pharmacol., 1990, 39:941-948.
Fox et al, "Sequence-specific binding of luzopeptin to DNA," Nuc. Acids Res., 1998, 16:2489-2507.
Gomes-Pereira et al, "Chemical modifiers of unstable expanded simple sequence repeats: what goes up, could come down.," Mutat. Res., 2006, 598:15-34.
Goula et al., "Stoichiometry of Base Excision Repair Proteins Correlates with Increased Somatic CAG Instability in Striatum over Cerebellum in Huntington's Disease Transgenic Mice," 2009, PLoS Genet., 5:e1000749.
Hagihara et al, "Inhibition of DNA replication by a d(CAG) repeat binding ligand," Nuc. Acids Symp. Ser. (Oxf.), 2006, 50:147-148.
Hagihara et al, "Small Molecule Modulates Hairpin Structures in CAG Trinucleotide Repeats," Chembiochem, 2011, 12:1686-1689.
Hou et al, "Incision-dependent and error-free repair of (CAG)n/(CTG)n hairpins in human cell extracts," Nature Struct. & Mol. Biol., 2009, 16:869-75.
Ishiguro et al, "Regulatory Role of RNA Chaperone TDP-43 for RNA Misfolding and Repeat-Associated Translation in SCA31," Neuron, 2017, 94(1):108-124.e7.
Ishii et al. "Small increase in triplet repeat length of cerebellum from patients with myotonic dystrophy," Hum. Genet., 1996, 98:138-140.
Kabbarah et al., A Panel of Repeat Markers for Detection of Microsatellite Instability in Murine Tumors, Mol. Carcinogen., 2003, 38:155-159.
Kennedy et al, "Dramatic tissue-specific mutation length increases are an early molecular event in Huntington disease pathogenesis," 2003, Human Mol. Genet., 12:3359-3367.
Koob et al., "An untranslated CTG expansion causes a novel form of spinocerebellar ataxia (SCA8)," 1999, 21:379-384.
Kovalenko et al, "Msh2 Acts in Medium-Spiny Striatal Neurons as an Enhancer of CAG Instability and Mutant Huntingtin Phenotypes in Huntington's Disease Knock-In Mice," PLoS One, 2012, 7:e44273, 10 pages.
Kremer et al., "Sex-Dependent Mechanisms for Expansions and Contractions of the CAG Repeat on Affected Huntington Disease Chromosomes," Am. J. Hum. Genet., 1995, 57:343-50.
Larson et al, "Age-, tissue- and length-dependent bidirectional somatic CAG•CTG repeat instability in an allelic series of R6/2 Huntington disease mice," Neurobiol. Dis., 2015 76:98-111.
Lee et al, "A novel approach to investigate tissue-specific trinucleotide repeat instability," BMC Syst. Biol., 2010, 4:29, 16 pages.
Lee et al, "Quantification of Age-Dependent Somatic CAG Repeat Instability in Hdh CAG Knock-In Mice Reveals Different Expansion Dynamics in Striatum and Liver," PLoS One, 2011, 6:e23647, 8 pages.
Li et al, "Naphhthyridine-Benzoazaquinolone: Evaluation of a Tricyclic System for the Binding t0 (CAG)n Repeat DNA and RNA," Chemistiy An Asian Journal, 2016, 11:13:1971-1981.
Lin et al, "R loops stimulate genetic instability of CTG • CAG repeats," PNAS USA, 2010, 107:692-697.
Mollersen et al, "Continuous and Periodic Expansion of CAG Repeats in Huntington's Disease R6/1 Mice," PLoS Genet., 2010, 6:e1001242, 12 pages.
Nakamori et al, "Bidirectional transcription stimulates expansion and contraction of expanded (CTG)†(CAG) repeats," Human Mol. Genet., 2011, 20:580-588.

Nakamori et al, "Scaled-down genetic analysis of myotonic dystrophy type 1 and type 2," Neuromuscul. Disord., 2009, 19:759-762.
Nakamori et al., "Stabilization of Expanded (CTG)•(CAG) Repeats by Antisense Oligonucleotides ," Mol. Ther., 2011, 19:2222-2227.
Nakatani et al, "Small-molecule ligand induces nucleotide flipping in (CAG)n trinucleotide repeats," Nat. Chem. Biol., 2005, 1:39-43.
Nakatani et al, "Solution structure of a small-molecular ligand complexed with CAG trinucleotide repeat DNA," Nuc. Acids Symp. Ser. (Oxf), 2005, 49:49-50.
Nielsen et al, "Sequence-Influenced Interactions of Oligoacridines with DNA Detected by Retarded Gel Electrophoretic Migrations," Biochem., 1998, 27:67-73.
Panigrahi et al, "In Vitro (CTG)•(CAG) Expansions and Deletions by Human Cell Extracts," J. Biol. Chem., 2002, 277:13926-34.
Panigrahi et al., "Isolated short CTG/CAG DNA slip-outs are repaired efficiently by hMutSβ, but clustered slip-outs are poorly repaired," PNAS USA, 2010, 107:(28):12593-12598.
Panigrahi et al., "Slipped (CTG) (CAG) repeats can be correctly repaired, escape repair or undergo error-prone repair," Nat. Struct. & Mol. Biol., 2005, 12:654-662.
PCT International Search Report and Written Opinion in International Appln. No. PCT/IB2017/054932, dated Dec. 19, 2017, 14 pages.
Pearson et al, "Alternative structures in duplex DNA formed within the trinucleotide repeats of the myotonic dystrophy and fragile X loci," Biochemistiy, 1996, 35:5041-5053.
Pearson et al, "Repeat instability: mechanisms of dynamic mutations," Genet., 2005, 6:729-742.
Pearson et al, "Slipped-strand DNAs formed by long (CAG)'(CTG) repeats: slipped-out repeats and slip-out junctions," Nuc. Acids Res., 2002, 30:4534-47.
Pearson et al., "Structural analysis of slipped-strand DNA (S-DNA) formed in (CTG)n•(CAG)n repeats from the myotonic dystrophy locus," Nuc. Acids Res., 1998, 26:816-823.
Pearson et al., "Human MSH2 binds to trinucleotide repeat DNA structures associated with neurodegenerative diseases," Hum. Mol. Genet., 1997 6:1117-1123.
Peterlin et al,"CTG repeat analysis in lymphocytes, muscles and fibroblasts in patients with myotonic dystrophy," Pflugers Arch., 1996, 431(6 Suppl 2):R199-200.
Pluciennik et al, "Extrahelical (CAG)/(CTG) triplet repeat elements support proliferating cell nuclear antigen loading and MutLα endonuclease activation," PNAS USA, 2013, 110:12277-12282.
Reddy et al, "Processing of double-R-loops in (CAG)•(CTG) and C9orf72 (GGGGCC)•(GGCCCC) repeats causes instability," Nuc. Acids Res., 2014, 42:10473-10487.
Sathasivam et al, "Identification of an HD patient with a (CAG)180 repeat expansion and the propagation of highly expanded CAG repeats in lambda phage," Hum. Genet., 1997, 99:692-695.
Seriola et al, "Huntington's and myotonic dystrophy hESCs: down-regulated trinucleotide repeat instability and mismatch repair machinery expression upon differentiation," 2011, Hum. Mol. Genet., 20:176-185.
Slean et al, "Absence of MutSbeta leads to the formation of slipped-DNA for CTG/CAG contractions at primate replication forks," DNA Repair, 2016, 42:107-118.
Tanaka et al, "Differential pattern in tissue-specific somatic mosaicism of expanded CAG trinucleotide repeat in dentatorubral-pallidoluysian atrophy, Machado-Joseph disease, and X-linked recessive spinal and bulbar muscular atrophy," J. Neurol. Sci., 1996, 135:43-50.
Telenius et al, "Somatic and gonadal mosaicism of the Huntington disease gene CAG repeat in brain and sperm," Nat. Genet., 1994, 6:409-414.
Thornton et al, "Myotonic dystrophy patients have larger CTG expansions in skeletal muscle than in leukocytes," Ann. Neurol., 1994, 35:104-107.
Tome et al., "MSH3 Polymorphisms and Protein Levels Affect CAG Repeat Instability in Huntington's Disease Mice," PLoS Genet., 9:e1003280, 16 pages.
Wohrle et al., "Heterogeneity of DM kinase repeat expansion in different fetal tissues and further expansion during cell proliferation

(56) References Cited

OTHER PUBLICATIONS in vitro: evidence for a causal involvement of methyl-directed DNA mismatch repair in triplet repeat stability," Hum. Mol. Genet., 1995, 4:1147-1153.
Yang et al, "Replication Inhibitors Modulate Instability of an Expanded Trinucleotide Repeat at the Myotonic Dystrophy Type 1 Disease Locus in Human Cells," Am. J. Hum. Genet., 2003, 73:1092-105.
Yoon et al, "Reply: Autosomal recessive cerebellar ataxia caused by a homozygous mutation in PMPCA," Brain, 2016, 139:1-2.
Liao et al., "Genetics Eugenics and Clinics," Hunan Science and Technology Press, 1st ed., Apr. 2000, Chapters, pp. 112-114 (with English translation).

\* cited by examiner

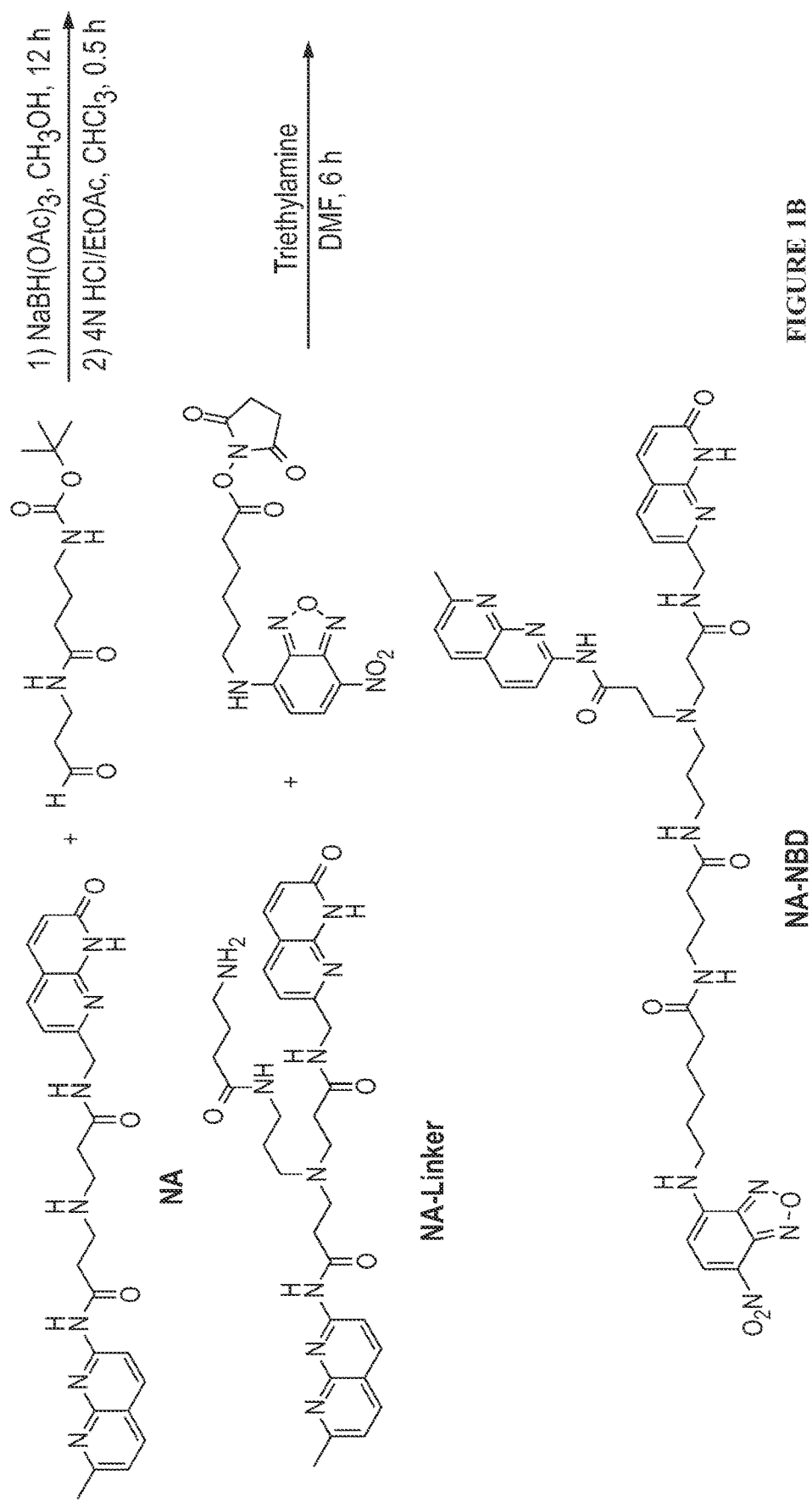
FIGURE 1A
FIGURE 1B

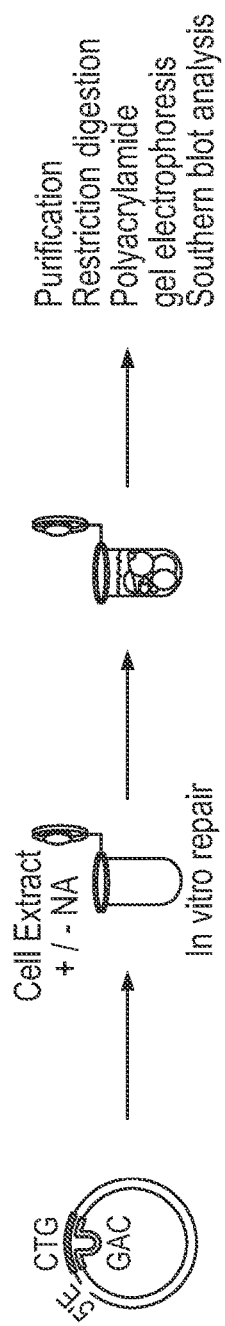
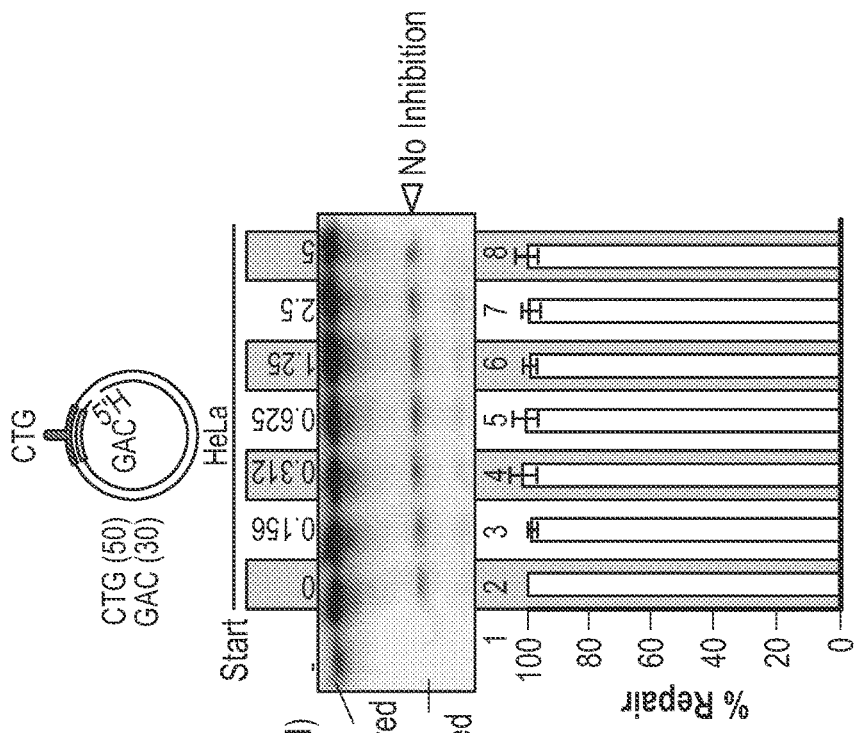
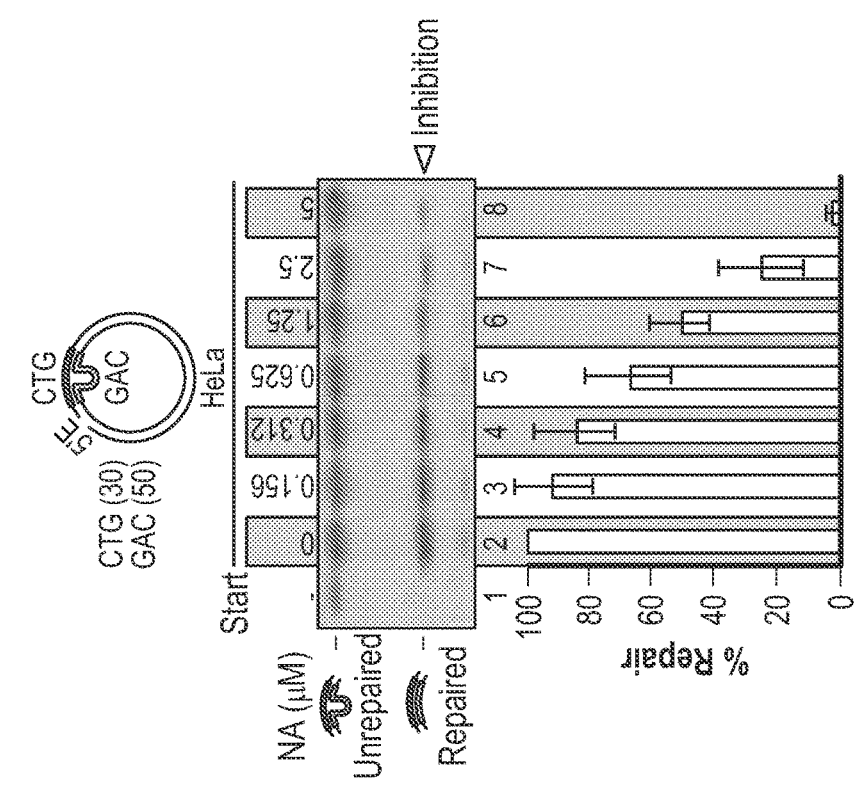
FIGURE 3A
FIGURE 3B
FIGURE 3C

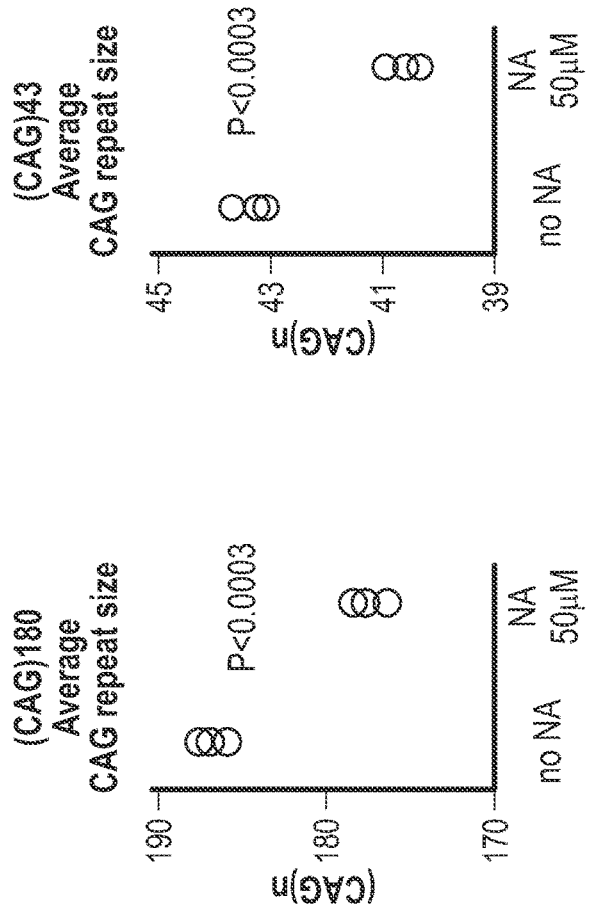
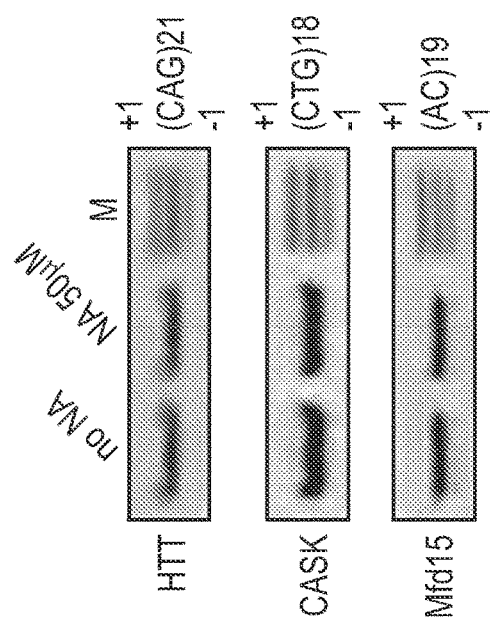
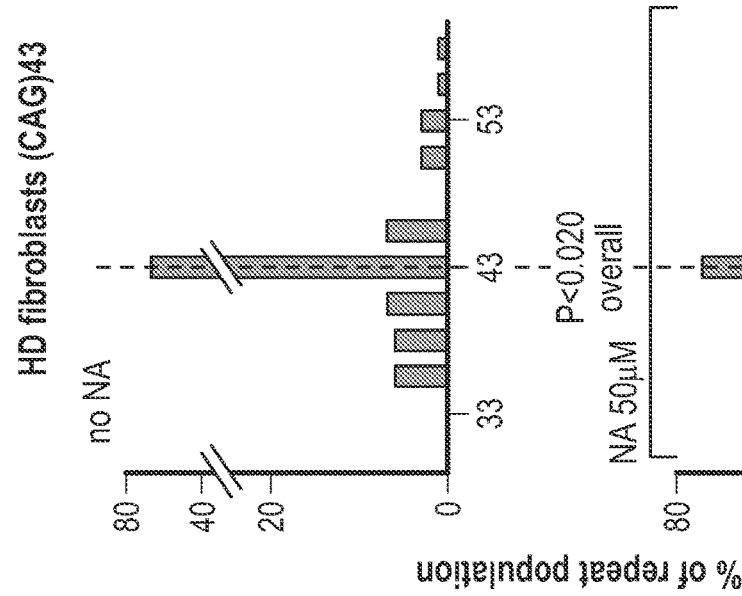
FIGURE 4E
FIGURE 4F
FIGURE 4G
FIGURE 4H

NA does not affect transcription across CAG

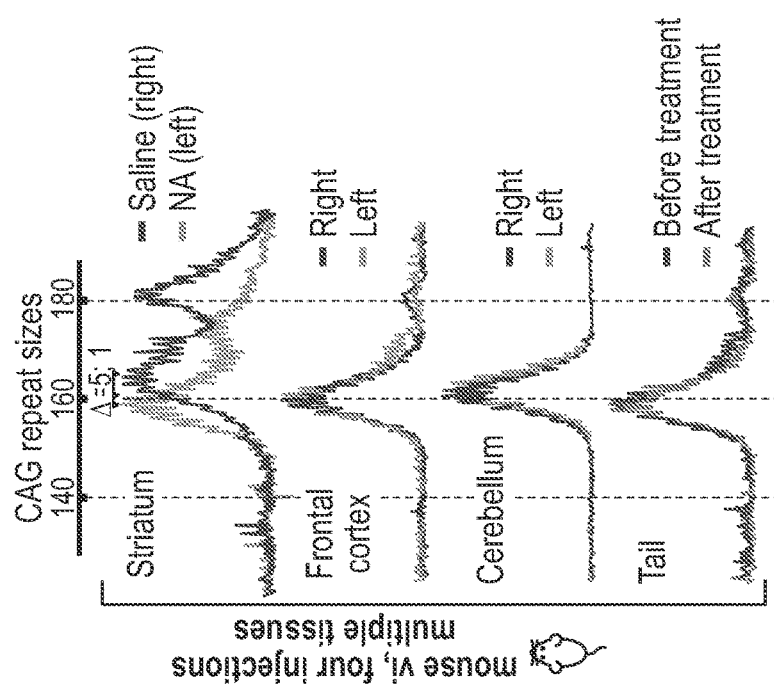
FIGURE 6D
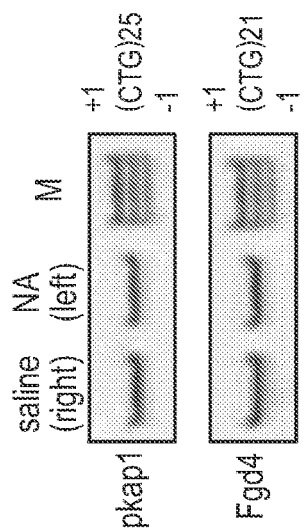
FIGURE 6F
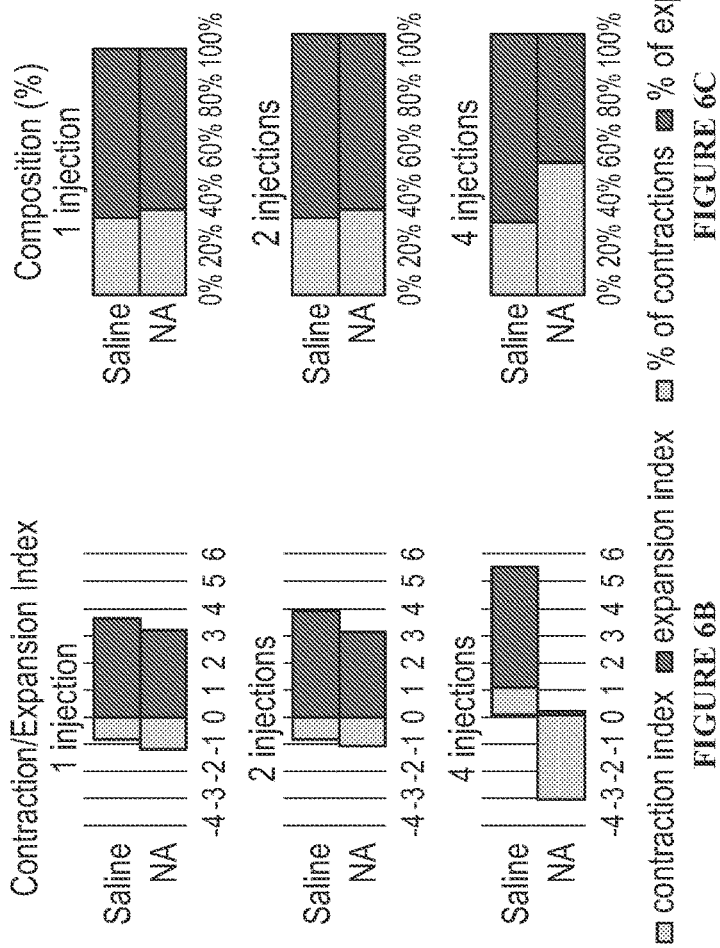
FIGURE 6C
FIGURE 6B
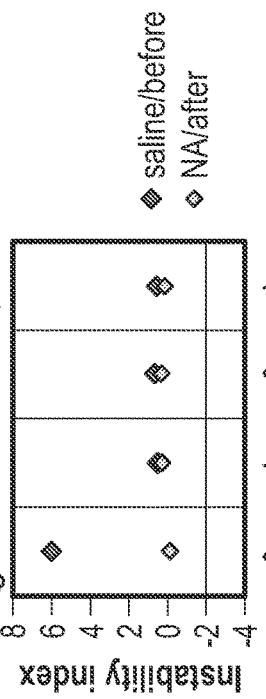
FIGURE 6E Quality control: Representative reads of insert results for sample 1 control

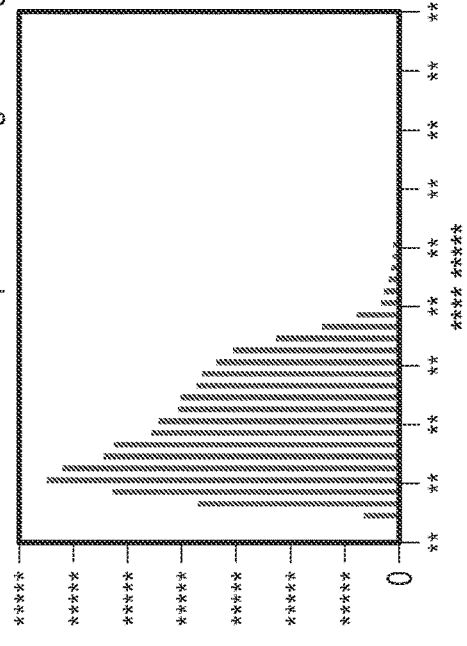

A Distribution of reads by PacBio SMRTbell insert length (bp)

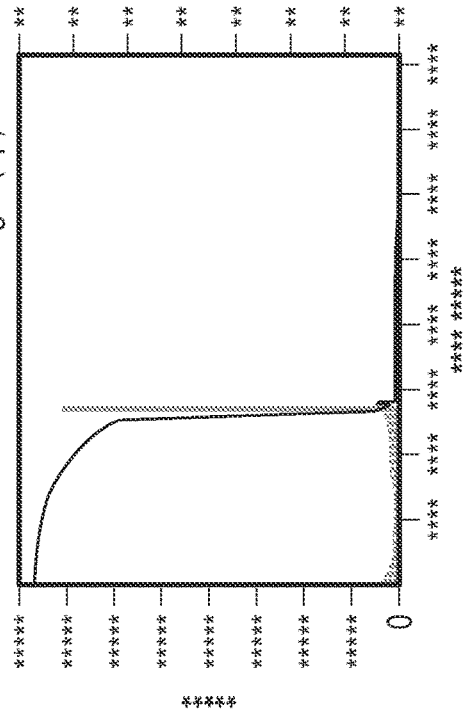

B Distribution of reads by the number of times a PacBio SMRTbell's insert was sequenced in a given long read

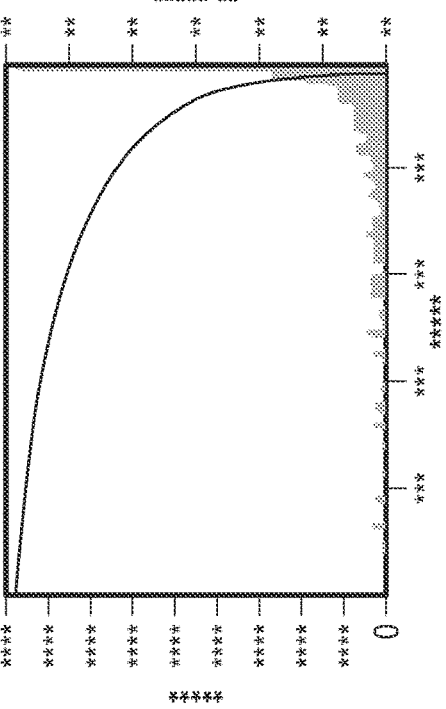

C Distribution of reads by the accuracy of the sequence called from all insert sequences contained in a given long read

FIGURE 13C

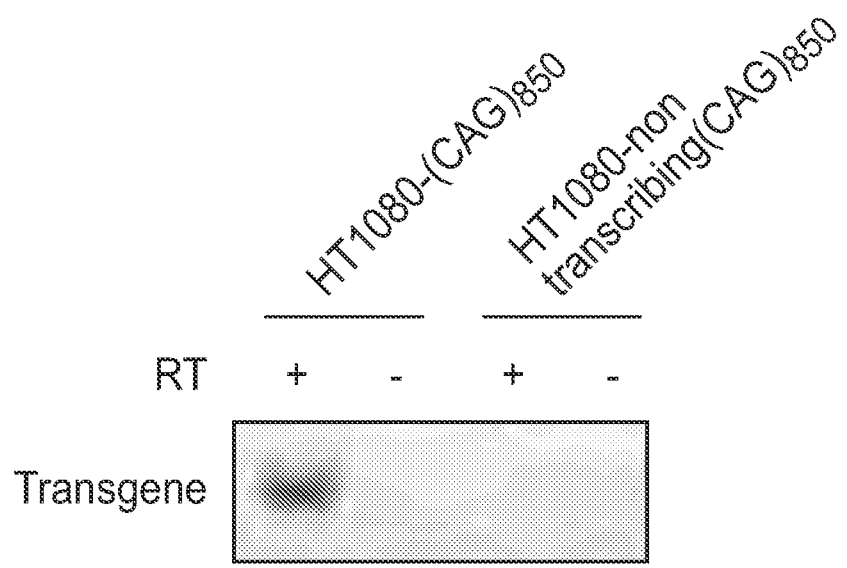
FIGURE 16A
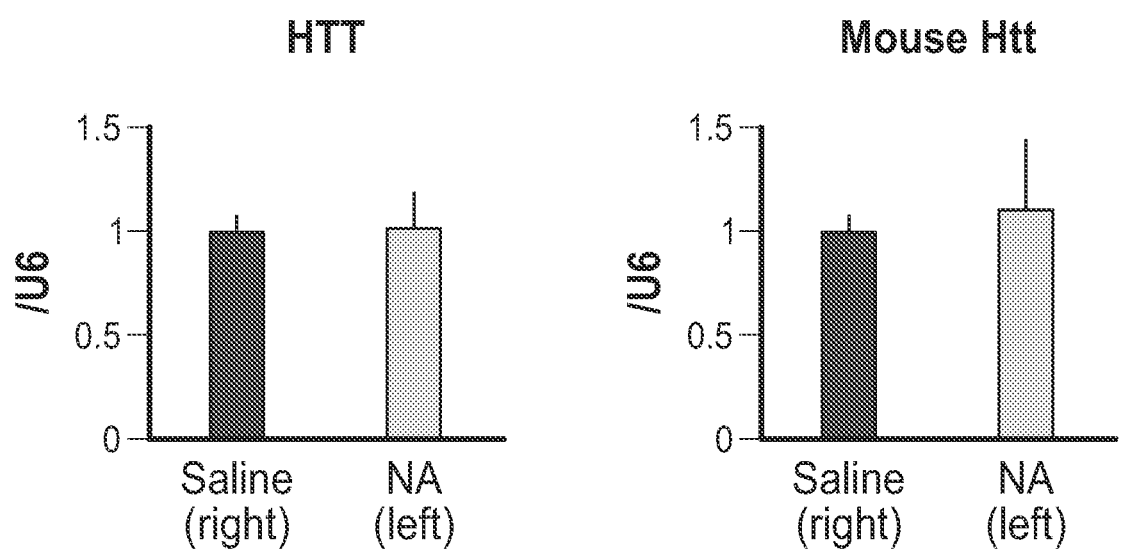
FIGURE 16B
FIGURE 16C

NA does not affect transcription in cells

Strategy for R-loop formation

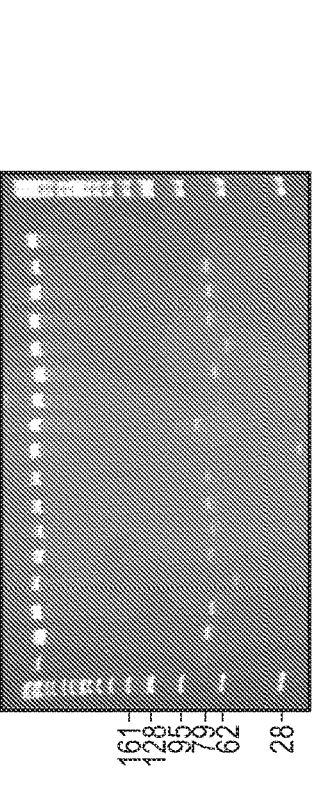
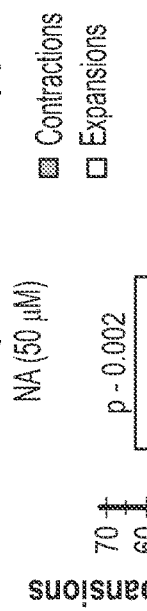
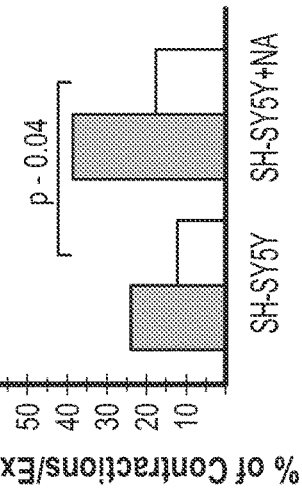
FIGURE 18A
FIGURE 18B
FIGURE 18C

5'-ATCATGGCTTTCCCCACGTTGACTGATTGCCCGAGGCACGCCTCGAGATCTAGCGTACGTCAGCTTGCGATA CTTTCCCCGTCTAGTCGCTA
TCGCCGAATTGCTAGCAAGCTTTCGATTCTAGAAATTCGG CTTTCCCCGTCTAGTCGCTA
AGCGGGCTTAACGATCGTTCGAAAGCTAAGATCTTTAAGCCGAAAGGGGCAGATCAGCGAT

FIGURE 22D

New Figure S19A

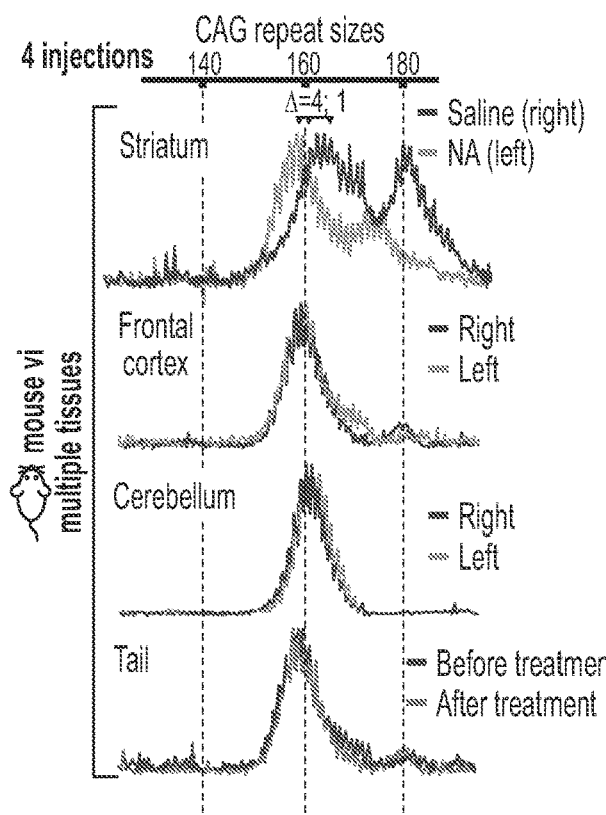

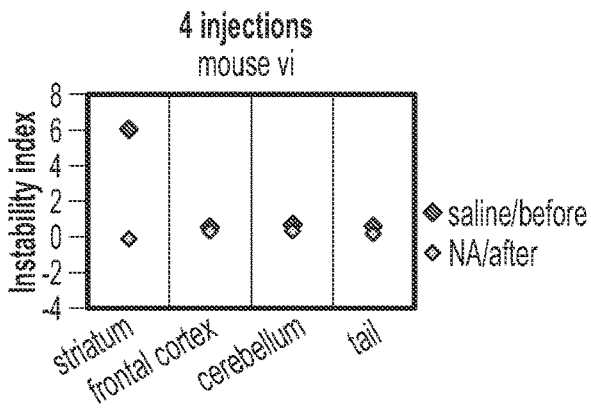

We have treated a total of 13 mice (one for 1 injection, two for 2 injections, and ten for 4 injections) in total (mice i, ii+iii, iv-xiii, respectively). CAG length analysis for mice i-vi are shown in Figure 5 and Fig. S19A-H. The repeat instability indices of each mouse is shown in Figure 5B, 5C, & 5E, and in Figure S21B mic In this Supplementary Figure (S19A-H) we provide CAG repeat length analysis in striatum, cortex, cerebellum and tail for eight of the ten mice treated with 4 injections (mice vi-xii). The the CAG scans of the other two mice (mice iv and v) are shown in Figure 5A.

New Figure S19B

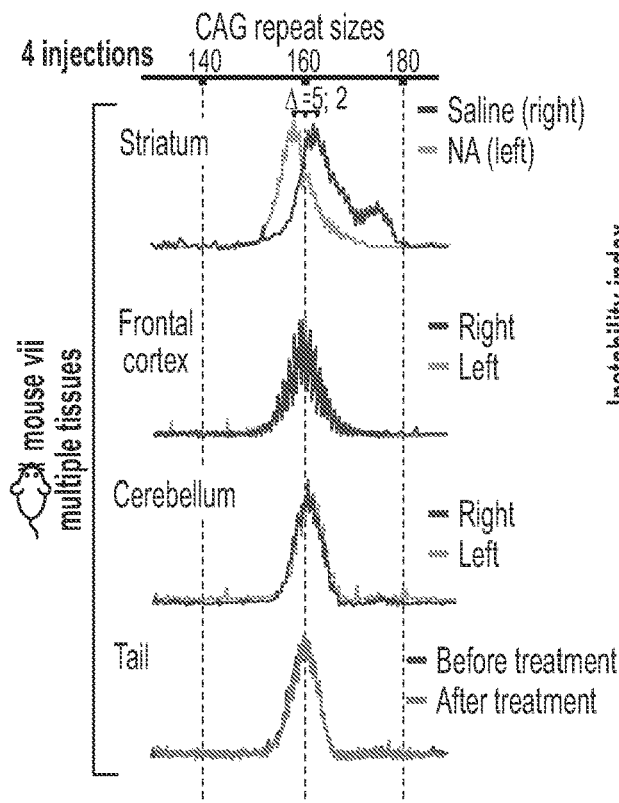

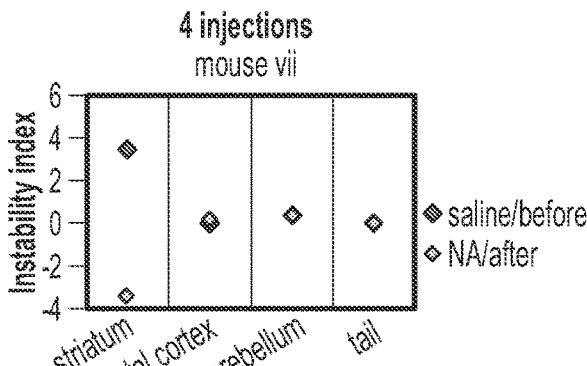

FIGURE 25

New Figure S19C

New Figure S19D

SALINE

| | | | | | | | | | | | | | | | | | | Sum |
|---|---|---|---|---|---|---|---|---|---|---|---|---|---|---|---|---|---|---|
| 3. Peak height | 1.99 | 3.22 | 4.94 | 6.75 | 7.77 | 8.24 | 8.08 | 7.30 | 6.25 | 4.82 | 3.45 | 3.18 | 3.59 | 3.88 | 4.28 | 4.85 | 5.13 | 4.87 | 4.55 | 4.20 | 4.04 | 3.06 | 1.95 → 110.39 |
| 4. Normalized peak height (peak height/ sum of peak height) | 0.0180 | 0.0292 | 0.0448 | 0.0611 | 0.0704 | 0.0746 | 0.0732 | 0.0661 | 0.0566 | 0.0437 | 0.0313 | 0.0288 | 0.0325 | 0.0351 | 0.0388 | 0.0439 | 0.0465 | 0.0441 | 0.0412 | 0.0380 | 0.0366 | 0.0277 | 0.0177 |
| 5. Change from the main allele | -5 | -4 | -3 | -2 | -1 | 0 | 1 | 2 | 3 | 4 | 5 | 6 | 7 | 8 | 9 | 10 | 11 | 12 | 13 | 14 | 15 | 16 | 17 |
| 6. Normalized peak (height x change) | -0.0901 | -0.1167 | -0.1343 | -0.1223 | -0.0704 | 0.0000 | 0.0732 | 0.1323 | 0.1699 | 0.1747 | 0.1563 | 0.1728 | 0.2276 | 0.2812 | 0.3489 | 0.4394 | 0.4394 | 0.5112 | 0.5294 | 0.5358 | 0.5327 | 0.5490 | 0.4435 | 0.3003 |

7. INSTABILITY INDEX    Sum = 5.0443

NA

| | | | | | | | | | | | | | | | | | | Sum |
|---|---|---|---|---|---|---|---|---|---|---|---|---|---|---|---|---|---|---|
| 3. Peak height | 2.77 | 5.01 | 6.71 | 8.26 | 8.37 | 7.67 | 5.95 | 4.60 | 3.41 | 2.67 | 2.75 | 2.91 | 2.91 | 2.76 | 2.67 | 2.44 | 2.15 | 2.00 | 2.07 | 2.15 | 2.04 → 84.71 |
| 4. Normalized peak height (peak height/ sum of peak height) | 0.0327 | 0.0591 | 0.0792 | 0.0975 | 0.0988 | 0.0905 | 0.0702 | 0.0543 | 0.0403 | 0.0315 | 0.0325 | 0.0344 | 0.0326 | 0.0315 | 0.0288 | 0.0254 | 0.0236 | 0.0244 | 0.0254 | 0.0241 |
| 5. Change from the main allele | -8 | -7 | -6 | -5 | -4 | -3 | -2 | -1 | 0 | 1 | 2 | 3 | 4 | 5 | 6 | 7 | 8 | 9 | 10 | 11 | 12 | 13 |
| 6. Normalized peak (height x change) | -0.2616 | -0.4140 | -0.4753 | -0.4875 | -0.3952 | -0.2716 | -0.1405 | -0.0543 | 0.0000 | 0.0315 | 0.0649 | 0.1031 | 0.1374 | 0.1629 | 0.1891 | 0.2016 | 0.2304 | 0.2361 | 0.2688 | 0.3046 | 0.3131 |

7. INSTABILITY INDEX    Sum = -0.0281

FIGURE 27A (Cont.)

METHODS OF TREATING DISEASES ASSOCIATED WITH REPEAT INSTABILITY

CROSS-REFERENCE TO RELATED APPLICATIONS

This application is a National Stage Application under 35 U.S.C. § 371 and claims the benefit of priority to International Application No. PCT/IB2017/054932 filed Aug. 12, 2017, which claims priority to U.S. Application No. 62/374,072 filed Aug. 12, 2016. The disclosures of the foregoing applications are hereby incorporated by reference in their entirety.

TECHNICAL FIELD

This disclosure generally relates to methods of treating diseases associated with repeat expansions.

BACKGROUND

Gene-specific CAG/CTG trinucleotide repeat expansions are responsible for at least 16 of the >40 neurodegenerative diseases caused by unstable repeats, including Huntington's disease (HD) and myotonic dystrophy (DM1). Ongoing repeat expansions occurring in affected tissues correlate with disease age-of-onset, severity, and progression. Dramatic repeat length variations exist between tissues of the same individual, with differences >5,000 repeats, with the largest expansions in heart, cerebral cortex and striatum. The considerably larger expansions in the clinically affected tissues of individuals further correlate ongoing somatic expansions with disease onset, severity and progression. Recent studies reveal that, for at least six of the sixteen CAG diseases (HD, SCA1, SCA2, SCA3, SCA7, & SCA17), DNA repair proteins are major modifiers of age-of-onset (Genetic Modifiers of Huntington's Disease (GeM-HD) Consortium, 2015, Cell, 162:516-526; Bettencourt et al., 2016, Annals Neurol., in press), lending further support to the correlation between ongoing somatic expansions and age-of-onset. This association is likely to be true for all 16 CAG diseases, each of which show somatic expansions, as well as other diseases associated with repeat instabilities.

Thus, methods of arresting or reversing somatic repeat expansions could be used to arrest or reverse disease progression and would be extremely beneficial in a therapeutic setting.

SUMMARY

This disclosure provides for methods of treating diseases caused by repeat DNA instability. This disclosure also provides for methods of inhibiting the further expansion of repeat DNA and, in some instances, reducing the size of the expanded repeat DNA (e.g., reducing the number of repeats).

In one aspect, a method of inhibiting the expansion of a repeat DNA sequence in a cell is provided. Such a method typically includes contacting the cell with naphthyridine-azaquinolone (NA).

In some embodiments, the contacting is in vivo. In some embodiments, the contacting step is performed a plurality of times. In some embodiments, the method further includes, prior to the contacting step, determining the number of repeats within the repeat DNA sequence. In some embodiments, the method further includes, after the contacting step, determining the number of repeats within the repeat DNA sequence.

In some embodiments, the cells are contacted with an amount of NA that is dependent on the number of repeats within the repeat DNA sequence. In some embodiments, the NA is a modified NA.

In another aspect, a method of reducing the number of repeats within a repeat DNA sequence in the genome of an individual is provided. Such a method typically includes administering at least one dose of a therapeutic amount of naphthyridine-azaquinolone (NA) to the individual.

In some embodiments, the NA is administered directly into the affected tissue. In some embodiments, the NA is administered systemically. In some embodiments, the administration is via injection.

In some embodiments, the NA is administered a plurality of times. In some embodiments, a plurality of doses of NA are administered. In some embodiments, the method further includes repeating the administering step a plurality of times.

In some embodiments, the therapeutic amount of NA is based on the number of repeats. In some embodiments, the therapeutic amount of NA is about 0.01 µM to about 1 M.

In some embodiments, the method further includes identifying an individual having a repeat DNA sequence. In some embodiments, the method further includes determining the number of repeats in one or more cells from the individual. In some embodiments, the method further includes monitoring the number of repeats in one or more cells from the individual.

In some embodiments, the NA is modified to increase its in vivo stability. In some embodiments, the NA is delivered via a liposome or an intracranial pump.

In still another aspect, a method of treating or preventing a disease in an individual caused by expansion of a repeat DNA sequence is a provided. Such a method typically includes administering at least one dose of a therapeutic amount of naphthyridine-azaquinolone (NA) to the individual.

In some embodiments, such a method further includes identifying an individual having a disease caused by repeat DNA instability. Representative diseases caused by expansion of a repeat DNA sequence include, without limitation, Huntington's disease (HD), Huntington's disease-like 2 (HDL2), myotonic dystrophy (DM1), Spinocerebellar ataxia type 1 (SCA1), SCA2, SCA3, SCA6, SCA7, SCA8, SCA12, SCA17, Spinal and bulbar muscular atrophy (SBMA), Dentatorubropallidoluysian atrophy (DRPLA), Fuch's Endothelial Corneal Dystrophy 2 (FECD2), schizophrenia, bipolar disorder (KCNN3), and breast cancer risk factor AIB1.

In some embodiments, the NA is administered prior to expansion of the repeat DNA sequence. In some embodiments, the administering step occurs prior to expansion of the repeat DNA sequence. In some embodiments, the NA is administered to the individual prior to birth (in utero). In some embodiments, the NA is administered to the individual following expansion of the repeat DNA sequence.

In one aspect, a method of treating an individual having a disease caused by an expanded repeat DNA sequence is provided. Such a method typically includes administering at least one dose of a therapeutic amount of naphthyridine-azaquinolone (NA) to the individual.

In another aspect, a method of reducing the number of repeats within a repeat DNA sequence in an individual is provided. Such a method typically includes administering at least one dose of a therapeutic amount of naphthyridine-azaquinolone (NA) to the individual.

In still another aspect, a method of inhibiting the expansion of a repeat DNA sequence in an individual is provided. Such a method typically includes administering at least one dose of a therapeutic amount of naphthyridine-azaquinolone (NA) to the individual. In some embodiments, the administration is into the affected tissue. In some embodiments, the administration is via injection. In some embodiments, the administration is systemic.

In some embodiments, the dose of a therapeutic amount of NA is administered more than once. In some embodiments, the dose of a therapeutic amount of NA is administered in a dose-dependent manner based upon the number of repeats. In some embodiments, the dose of a therapeutic amount of NA is about 0.01 µM to about 1 M. In some embodiments, any of the methods described herein further includes repeating the administering step a plurality of times.

In some embodiments, any of the methods described herein further includes identifying an individual having a disease caused by repeat DNA instability. In some embodiments, any of the methods described herein further includes identifying an individual having a repeat expansion. In some embodiments, any of the methods described herein further includes determining the size of the repeat in cells from the individual. In some embodiments, any of the methods described herein further includes monitoring the size of the repeat in cells from the individual.

In some embodiments, the NA is modified to increase its in vivo stability. In some embodiments, the NA is delivered via a liposome or an intracranial pump.

In some embodiments, the disease caused by trinucleotide repeat DNA instability includes Huntington's disease (HD), Huntington's disease-like 2 (HDL2), myotonic dystrophy (DM1), Spinocerebellar ataxia type 1 (SCA1), SCA2, SCA3, SCA6, SCA7, SCA8, SCA12, SCA17, Spinal and bulbar muscular atrophy (SBMA), Dentatorubropallidoluysian atrophy (DRPLA), Fuch's Endothelial Corneal Dystrophy 2 (FECD2), schizophrenia, bipolar disorder (KCNN3), or breast cancer risk factor AIB1.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DESCRIPTION OF DRAWINGS

FIG. 1A shows the structure of naphthyridine-azaquinolone (NA).

FIG. 1B shows the chemical reactions that were used to label NA with NBD.

FIG. 16 shows that NA does not affect transcription across HTT. Panel A of FIG. 16 shows RT-PCR analysis of transgene expression in HT1080-(CAG)850 and HT1080-non transcribing (CAG)850 cells. Results demonstrate that the CAG repeat is not transcribed in HT1080-non transcribing cells and that it is integrated as a single copy. Strand specific RT-PCR (1 weeks). AttB-PhiC31 system have been widely used for single copy integration. Panel B of FIG. 16 was determined by quantitative real-time reverse transcriptase (qRT)-PCR and normalized to U6 RNA, expressed as the ratio of NA-treated vs. PBS-treated R6/2 striatum. Data are indicated as the mean±SD of triplicates.

Figure 17A:
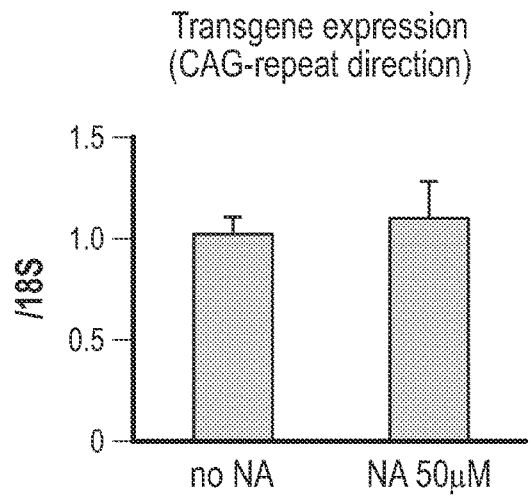
Figure 17B:
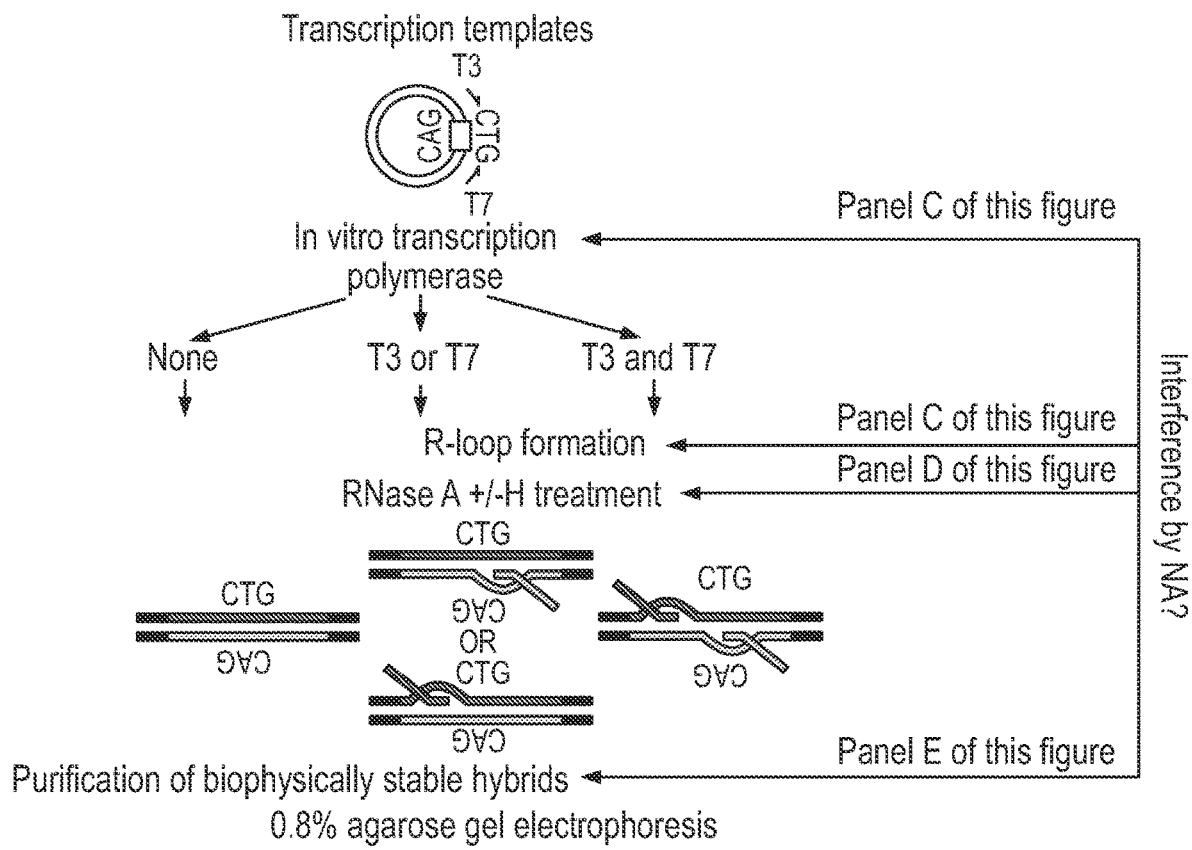
Figure 17C:
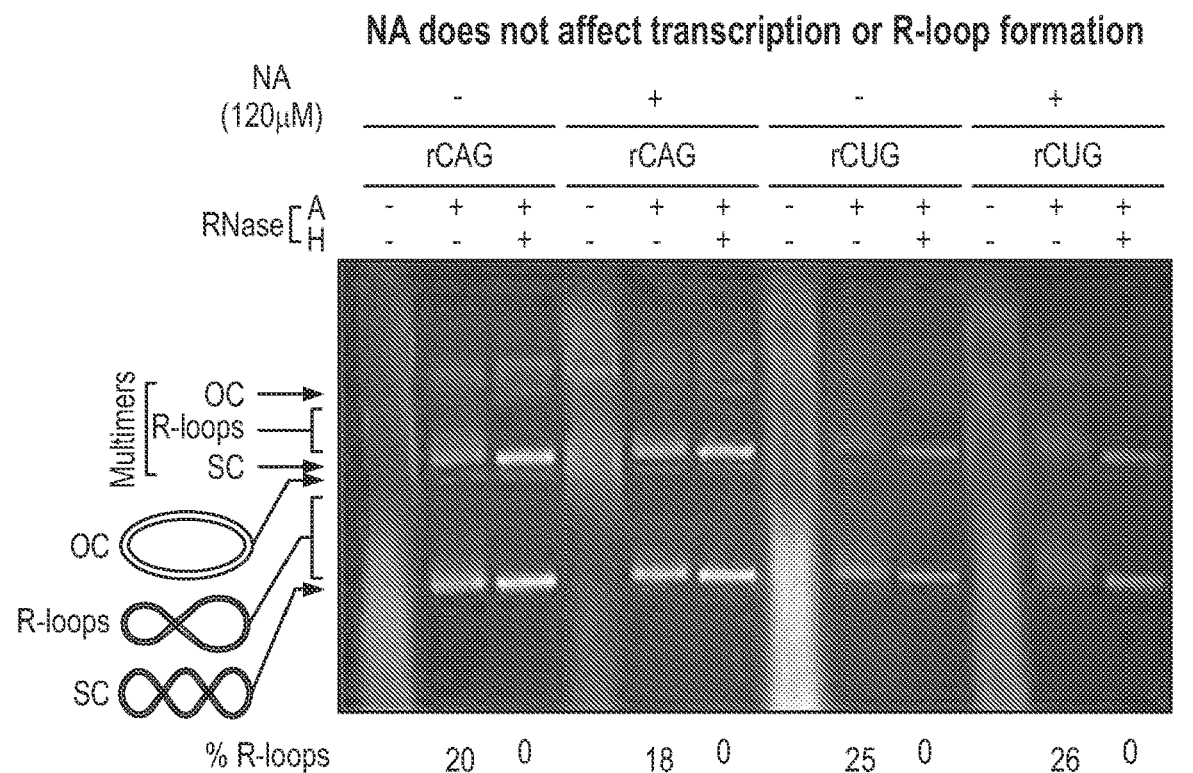
Figure 17D:
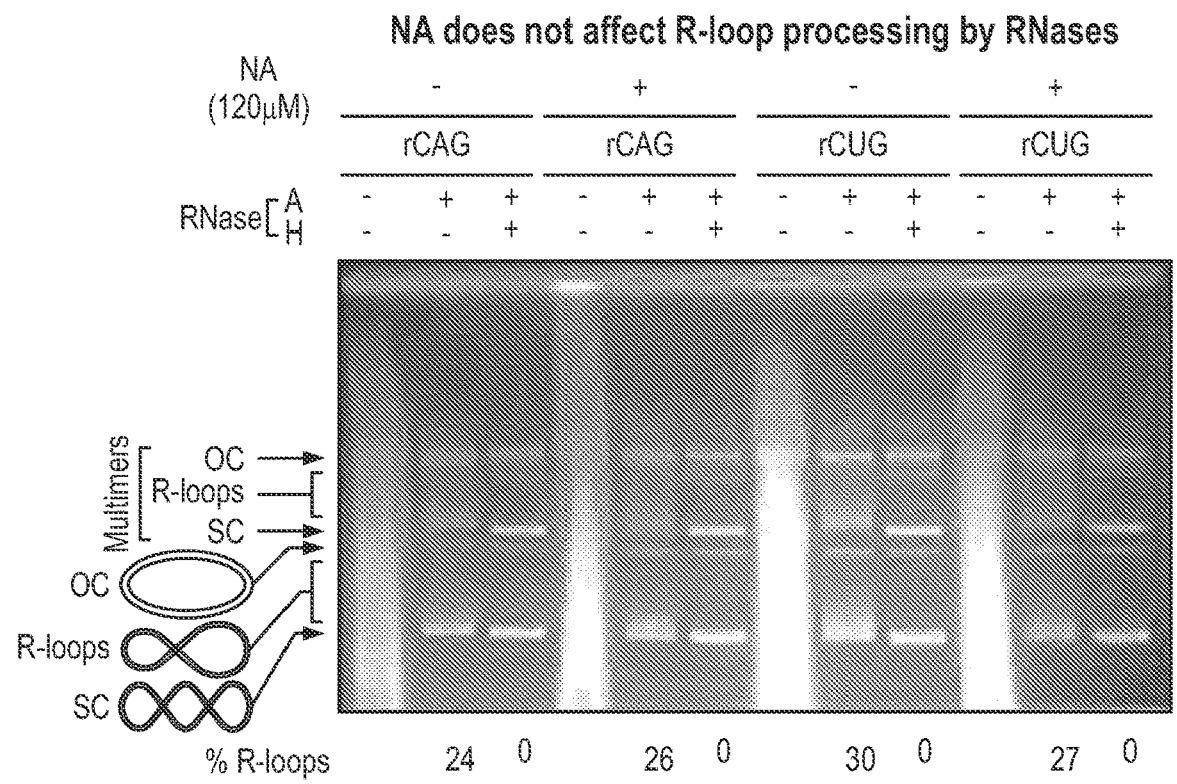
Figure 17E:
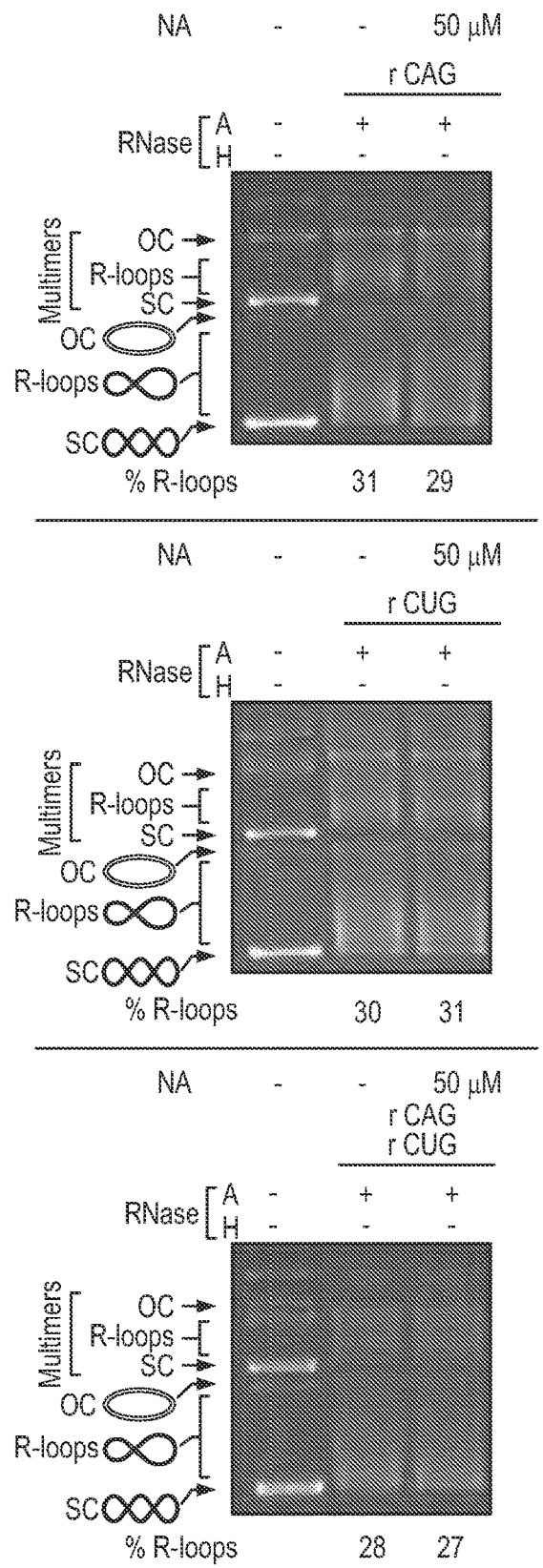

NA-induced displacement of the RNA component from the R-loop was not observed, which one might expect were NA to competitively bind for RNA away from the R-loop (FIG. 17E). The inability of NA to compete for the binding to RNA repeats is likely due to its low binding to these RNAs. A study of NA interacting with RNAs of one repeat length, r(CAG)9 (Li et al., 2016, Chem. Asian J., 11:1971-1981). Notably, the affinity of NA for RNA (CAG)9 versus DNA (CAG)9 was several fold different. Moreover, the binding stoichiometry of NA to d(CAG)9 and r(CAG)9 was quite different. According to the surface plasmon resonance (SPR) assay for d(CAG)9 (amount of immobilization was 497 RU) and r(CAG)9 (524 RU), NA binding to d(CAG)9 produced significant changes in the SPR intensity (140 RU) whereas only modest changes were observed for r(CAG)9 (8 RU). Electrospray ionization time-of-flight mass spectrometry clearly suggested the much higher affinity of NA to d(CAG)9 as compared to r(CAG)9. Due to the ambiguity in the stoichiometry of NA-binding to d(CAG)9 and r(CAG)9, it is scientifically difficult to accurately measure the binding constant for NA-binding to d(CAG)9 and r(CAG)9. In addition, all these experiments were conducted in vitro, where there were only nucleic acids and NA in the buffer solution. It seems reasonable that NA binding to r(CAG)9 is not significantly effective in the cell. The absence of strong binding of NA to RNA repeats is consistent with its inability to compete away the RNA from the R-loop (FIG. 17E).

FIG. 17 are the results of experiments that show that NA does not affect transcription, R-loop formation, processing by RNAses, or R-loop biophysical stability. Panel A of FIG. 17 is a graph of RNA transcript levels of transgene (transcript in the CAG-direction) in HT1080-(CAG)850 cells treated with or without NA (50 µM). Quantitative reverse transcription (RT)-PCR was performed using TaqMan Gene Expression assays. NA (50 µM) did not affect transcription of the CAG-repeats containing transcript. Data are the mean±SD of triplicates. Panel B of FIG. 17 is a schematic for R-loop formation and processing. Arrows identify the steps at which NA may disrupt either transcription, R-loop formation, RNaseA/H digestion, R-loop biophysical stability, or R-loop processing, tested in panels A, D, C and E, respectively, of FIG. 17. Panel C of FIG. 17 shows a plasmid harboring (CAG)79●(CTG)79 repeats that was in vitro transcribed on either strand with T3 or T7 RNA polymerases, in the presence or in the absence of NA (120 µM). Reaction products were then treated with RNase A (labeled "A"), to cleave all single-stranded RNAs, and resolved on 1% agarose gel. Control treatment with RNaseH (labeled "H"), eliminating RNA:DNA hybrids, was performed to reveal the RNA-free supercoiled DNAs. The presence of NA (50 µM) during transcription did not affect R-loop formation. Panel D of FIG. 17 shows in vitro transcription of a supercoiled plasmid containing an expanded tract of (CAG)79●(CTG)79 repeats was performed using T3 or T7 RNA polymerases transcription products and treated with RNaseA (labeled "A") or with both RNaseA and RNaseH (labeled "H"), in the presence or in the absence of NA (120 µM). Reaction products then were resolved on 1% agarose gel. NA (50 µM) didn't affect the cleavage of ssRNAs by RNaseA, nor did NA affect the processing of RNA:DNA hybrids by RNaseH. Panel E of FIG. 17 shows supercoiled DNAs with (CAG)79° (CTG)79 (lane 1) were transcribed in vitro across the repeats on both strands, with T3 and T7 RNA polymerases to yield double-R-loops. Double-R-loops were then treated with RNaseA or H (labeled "A" or "H") and incubated with NA (50 µM). Reaction products were then resolved on 1% agarose gel. Control reactions with double-R-loops treated with both RNaseA and RNaseH (labeled "H") (lane 5) and the supercoiled plasmid itself (lane 6) were unaltered by NA (500 M, not shown). The position of supercoiled plasmid in dimer or monomer form is indicated by "SC". The top "SC" represents linked dimers and the bottom "SC" represents monomers. In Panels C, D, and E, NA was either included in the transcription reaction (Panel C), only in the RNAse A/H reaction, only following the RNAse A/H clean-up. NA does not inhibit transcription, R-loop formation, digestion of R-loops by RNase A/H or disruption of the RNA from the R-loop.

FIG. 18 shows the effect of NA on R-loop formation, processing, and instability. Panel A of FIG. 18 shows supercoiled DNAs with (CAG)79●(CTG)79 (lane 1) were transcribed in vitro across the repeats on both strands with T3 and T7 RNA polymerases to yield double-R-loops. Double-R-loops were then treated with RNaseA or H (labeled "A" or "H") and incubated with 50 µM of NA. Reaction products were then resolved on 1% agarose gel. At the higher concentration of NA, the R-loop smear is reduced (lane 4). Control reactions with double-R-loops treated with both RNaseA and RNaseH (labeled "H") (lane 5) and the supercoiled plasmid alone (lane 6) were unaltered by the higher NA concentration. Positions of supercoiled plasmid in dimer or monomer forms are indicated by "SC". Panel B of FIG. 18 is a schematic of R-loop formation, processing, and analysis. Pre-formed double-R-loops were processed by terminally differentiated (retinoic acid) human neuron-like cell extracts (SH-SY5Y) in the absence or presence of NA (50 µM), as described and DNA repeat lengths were assessed as expansions, contractions, or stable, by the STRIP assay. Panel C of FIG. 18 is a graph showing a representative example of STRIP analysis. Transcription products were isolated, processed and transformed in *E. coli* cells, previously shown to stably maintain the (CAG)79●(CTG)79 lengths. Plasmids isolated from individual bacterial colonies were digested with restriction enzymes to release the repeat containing fragment, resolved on 4% polyacrylamide gels and scored for instability.

Figure 19:
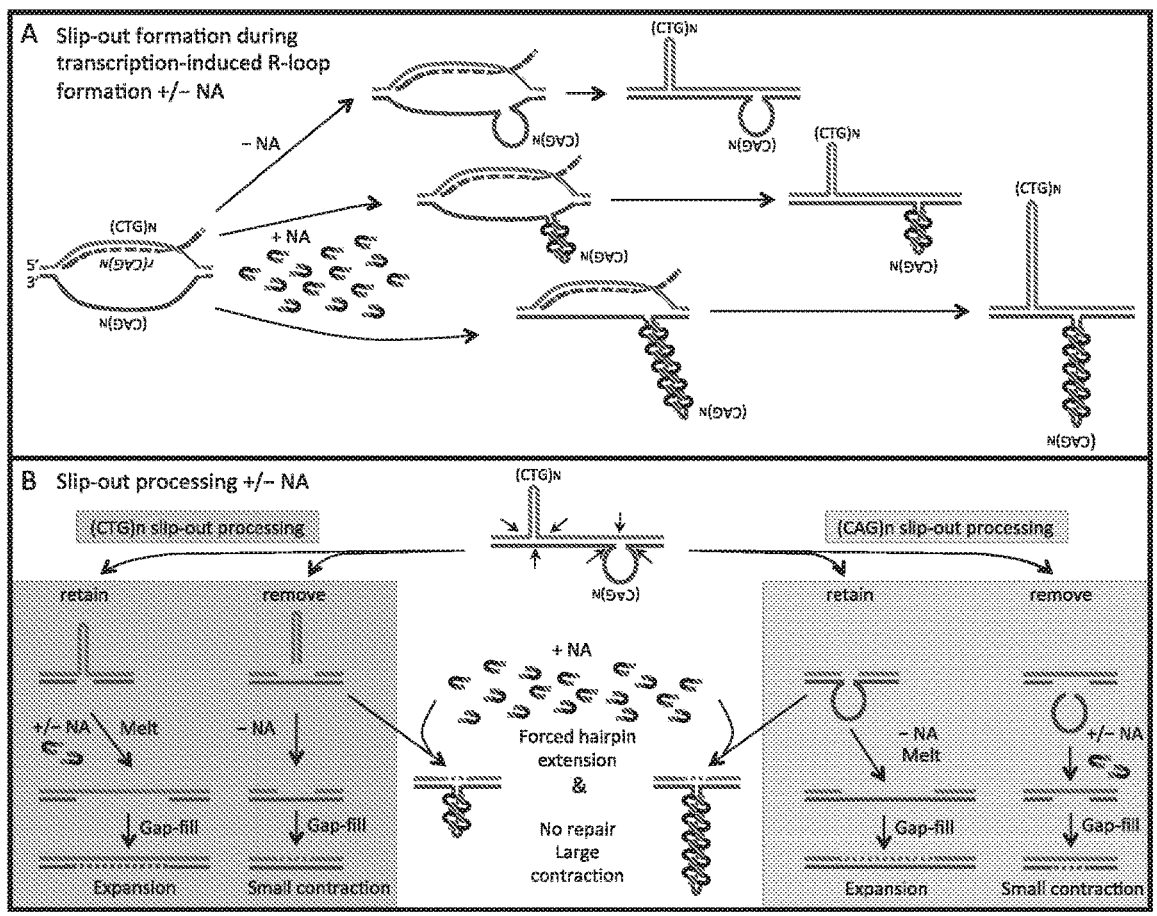

FIG. 19 shows a possible mechanism through which NA may induce contractions of expanded CAG tracts. Panel A of FIG. 19 shows transcription-induced R-loop formation with a r(CAG)n in a hybrid with the CTG DNA template strand will displace the CAG strand, making it available to be bound by NA. NA may bind varying amounts, making shorter or longer hairpins. Intra-strand DNA repeat structures formed at R-loops, or at the reannealed DNA strands upon RNA removal, could be processed to repeat expansions and contractions by unclear mechanisms. Slipped-out CAG and slipped-out CTG repeats were predominantly in the random-coil and hairpin conformations, respectively. Repeat instability following the processing of R-loops has been shown to occur through the formation of slipped-DNAs from the R-loops, and their subsequent aberrant repair (Panigrahi et al., 2010, PNAS USA, 107:12593-9). It is possible that during formation of the rCAG-dCTG R-loop, NA may bind the intra-strand hairpins formed on the displaced dCAG strand and possibly further extend these hairpins as demonstrated in Panel D of FIG. 2. Panel B of FIG. 19 shows that, similarly, NA may bind to CAG slip-outs formed by out-of-register reannealing of DNA strands following removal of RNA (Panel B of FIG. 19). These NA-bound structures may shift processing to contractions over expansions. Processing of slipped-CAG/CTG repeats is complex, and has been shown to involve multiple endonucleolytic incisions (see arrows in panel B of FIG. 19) by unknown nucleases (Hou et al., 2009, Nature Struct. & Mol. Biol., 16:869-75; Pluciennik et al., 2013, PNAS USA, 110:12277-82). NA also can bind to gaps of single-stranded (CAG)10 repeats, which can arise during the removal of CTG slip-outs. That NA blocked the repair of a (CAG)20 slip-out is consistent with the inability of human and other DNA polymerases to extend primers along NA-bound (CAG)10 templates. These results suggest that the effect of NA upon transcription-enhanced repeat instability could have arisen by NA perturbation of R-loop processing.

Figure 20:
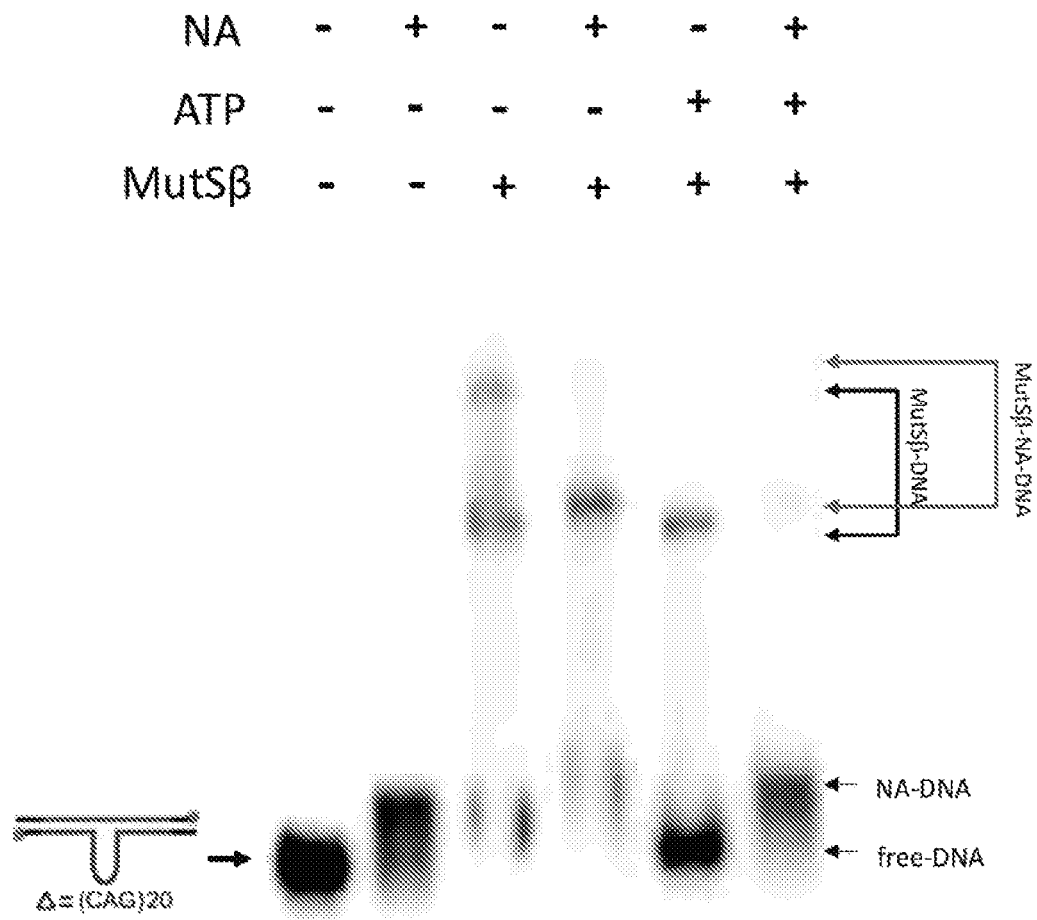

FIG. 20 shows that MutS beta was allowed to bind radio-labelled slipped-DNA, containing a single slip-out of (CAG)20, at room temperature for 30 min in a buffer containing 10 mM Hepes-KOH pH 7.5, 110 mM KCl, 1 mM EDTA, and 1 mM DTT. Addition of ATP (+/−Mg+) into this reaction disrupts binding of MutS beta to the DNA, as previously demonstrated. Addition of NA has no effect on binding or dissociation of MutS beta with this substrate.

Figure 21:
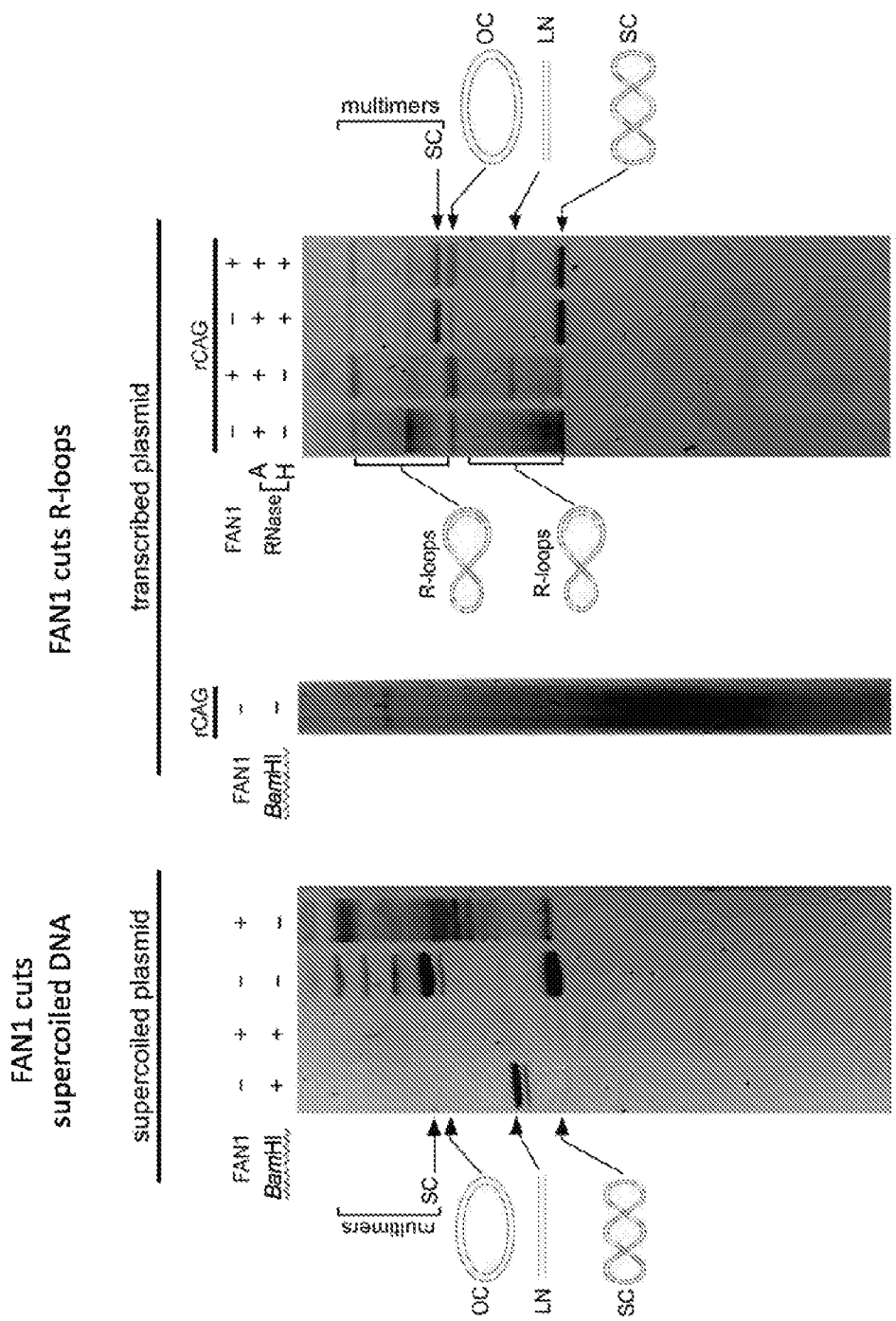

FIG. 21 shows FAN1 cleavage of supercoiled DNA, linear DNA and transcription-induced R-loops. A supercoiled plasmid harboring (CAG)79■(CTG)79 repeats, was linearized with BamHI, then incubated at 37° C. for 15 min with 200 nM FAN1 (left panel, first two lanes). The same supercoiled plasmid was treated directly with 200 nM FAN1 (left panel, second two lanes). The same plasmid was in vitro transcribed across the CTG strand with T3 RNA polymerase (middle panel). Transcription reaction products were then treated with RNase A, to cleave all single-stranded RNAs, or both RNase A and with RNaseH, to also eliminate RNA: DNA hybrids. These reactions were purified by extraction with phenol/chloroform/isoamyl alcohol (25:24:1, v/v/v) and ethanol precipitation, and incubated at 37° C. for 15 min with 200 nM FAN1 (right panel). All reaction products were analyzed on 1% agarose gels run in 1×TBE buffer at 80 V for 3 h. Gels were subsequently stained with ethidium bromide (0.5 mg/ml) to allow visualization of total nucleic acid under ultraviolet (UV) light. FAN1 cleaves supercoiled and linear DNAs (left panel), as well as the transcription-induced R-loop containing DNAs, releasing the supercoil-dependent RNA portion (right panel). The position of supercoiled plasmid in monomer or multimer form is indicated by 'SC'. 'OC' indicates the open circular form. 'LN' indicates the linearized plasmid.

FIG. 22 shows that FAN1 cleavage is altered by the presence of a CAG hairpin in the flap-DNA substrate and this activity is inhibited by NA-binding to the CAG hairpin. Flap-DNA substrates (see sequences in Panels D-F of FIG. 22) are schematically shown in the top panel: 5'-flap DNA with no repeats (Panel A of FIG. 22), 5'-flap DNA with (CAG)20 repeats in the flap (Panel B of FIG. 22), 5'-flap DNA with (CAG)20 repeats in the duplex region (Panel C of FIG. 22). All DNA structures were $^{32}$P radiolabeled at the 5'-end of the flap strand. 1 pmol of each substrate was incubated with increasing concentration of NA (7.5 µM, 15 µM, 50 µM) and then treated with 200 nM FAN1. Nuclease reactions were analyzed on a native 8% polyacrylamide gel at 200V for 1 h. The amount of digested product was quantified by densitometric analysis. All lanes are from the same gel, and they were separated for clarity. Histograms indicate the mean of three independent experiments and the corresponding standard deviation. To map FAN1 digestion sites, reaction products were separated on a 8% denaturing gel, together with Maxam-Gilbert sequencing reactions. Cut sites are indicated by arrowheads (going from white to black to indicate the increasing digestion efficacy). The different digestion fragments are indicated by letters (a,b,c). 's' indicates the starting substrate: 's+NA' indicates the shifted substrate due to NA binding to the CAG slip-out. The cut sites are indicated by the nucleotide location relative to either the end of the DNA, the junction point, or the repeat unit number. Panels D-F of FIG. 22: cleavage sites were mapped for the three substrates; Panel D of FIG. 22 corresponds to Panel A of FIG. 22; Panel E of FIG. 22 corresponds to Panel B of FIG. 22; Panel F of FIG. 22 corresponds to Panel C of FIG. 22.

Figure 23:
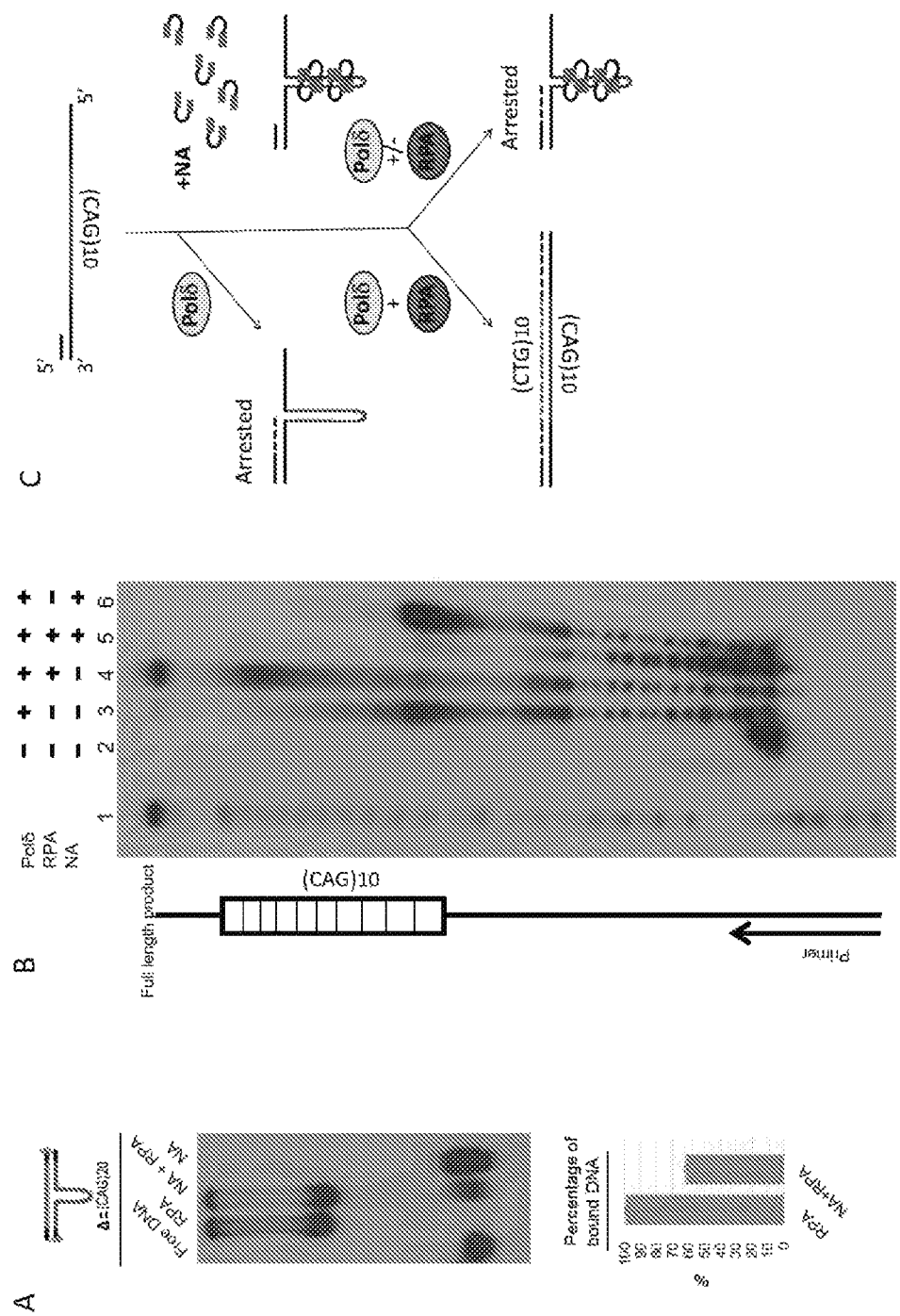

FIG. 23 shows that NA competes with RPA binding and blocks the enhanced progression of pol delta along a CAG template. Panel A of FIG. 23 shows the binding of RPA (250 nM) to a DNA substrate containing a slip-out of (CAG)20 (lane 2), $^{32}$P labelled on both strands (schematic on top). The substrate was incubated with NA (50 µM) for 10 min at RT, prior addition of RPA. NA competes with RPA binding to the (CAG)20 substrate (lane 3). The percentage of DNA bound to RPA was quantified by densitometric analysis. Histograms indicate the mean of three independent experiments and the corresponding standard deviation. Panel B of FIG. 23 shows that a polymerase extension assay was performed as previously described. 0.1 µM of a (CAG)10 template oligo was annealed with 0.1 µM of a $^{32}$P labelled primer and incubated with or without NA (50 µM) for 30 min at RT. 250 nM RPA and/or 20 nM Pol delta was added to the reaction and incubated for 15 min at 37° C. Reaction products were separated on a 6% sequencing gel together with Maxam-Gilbert sequencing reactions (lane 1). Primer only is in lane 2. Pol delta alone cannot synthesize through the CAG tract (lane 3) but its activity is enhanced by the addition of RPA (lane 4). NA blocks the enhanced progression of pol delta along the CAG template (lane 5 and 6), a result consistent with NA binding competitively against RPA for the CAG tract. Panel C of FIG. 23 shows a schematic of a possible mechanism for NA-induction of contraction through an inability of polymerases to synthesize across NA-bound CAG templates.

Figure 24:
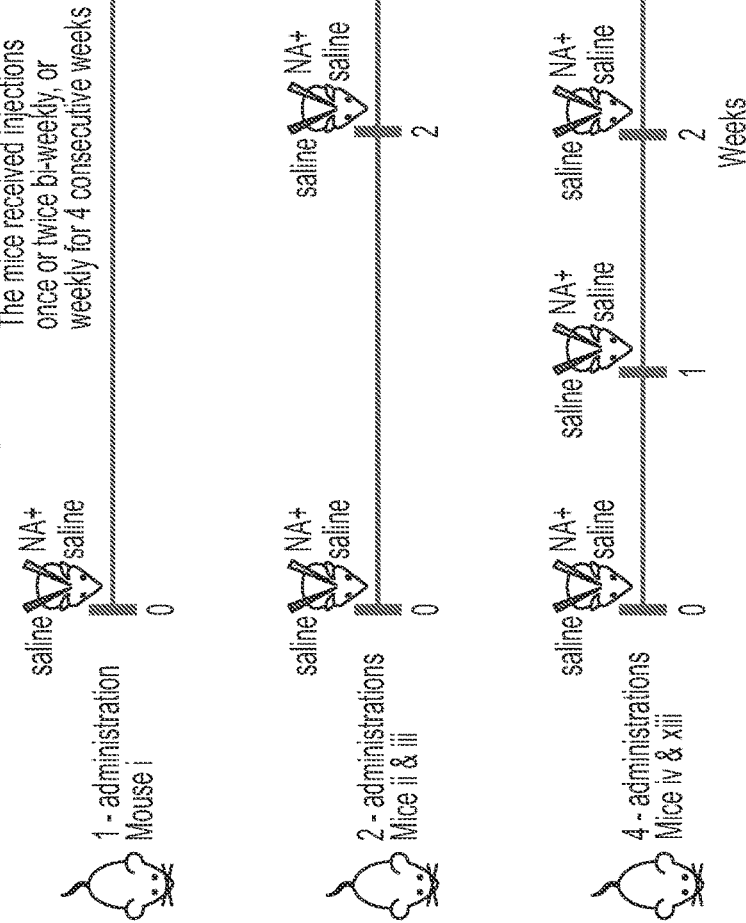

FIG. 24 shows the NA and saline injection regimen for R6/2 HD mice.

Figure 6A:
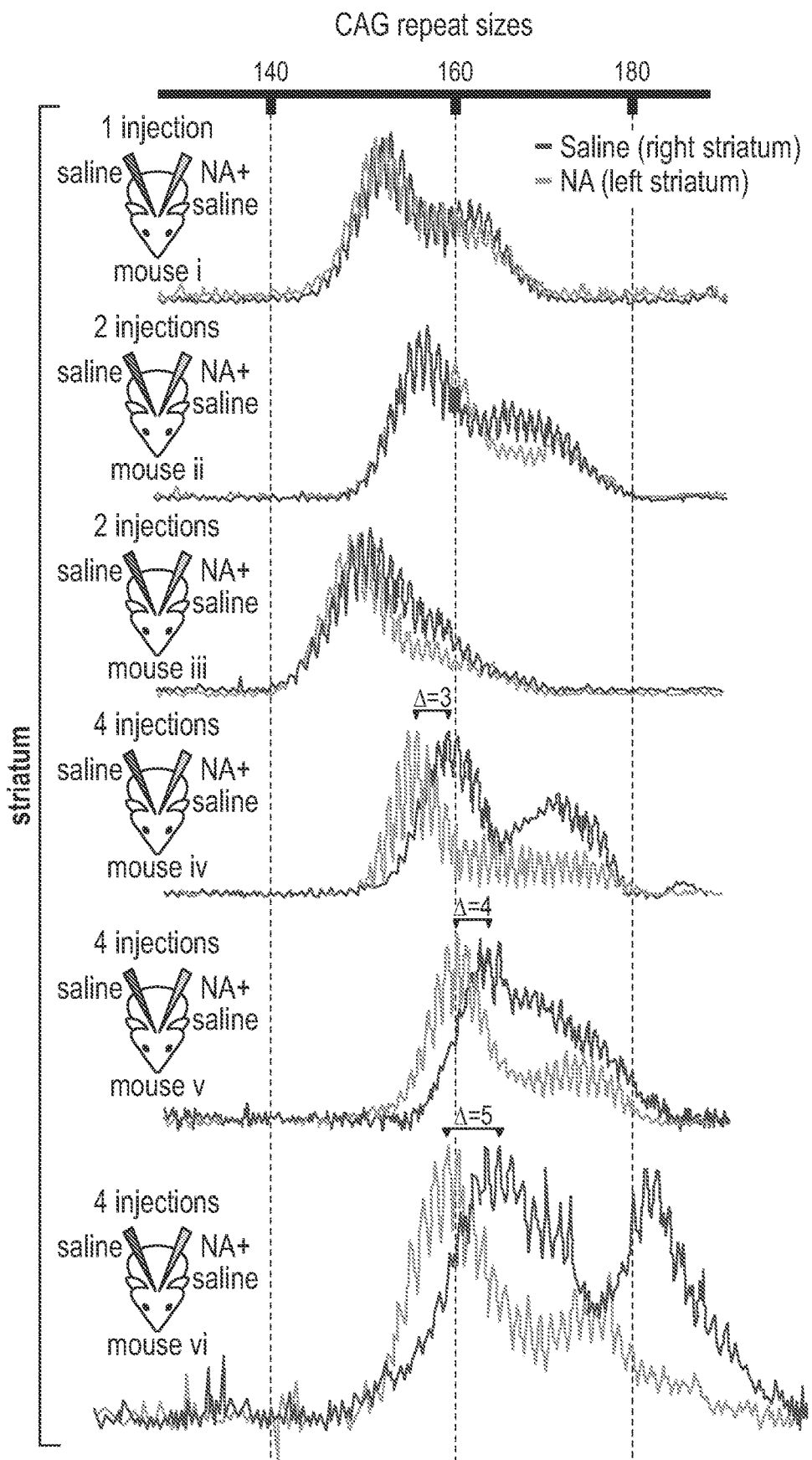
FIG. 6 are the results of experiments showing that NA induces CAG contractions in R6/2 mouse striatum. Panel A of FIG. 6 is an analysis of CAG length and shows the distribution of CAG repeat lengths in striatum from six representative R6/2 mice with one (mouse i), two (mice ii and iii) or four injections of NA (mice iv, v, vi) over a four-week period. NA, dissolved in saline, was injected into left striatum (blue) and saline only was injected into right striatum (red) (see FIG. 24). NA does not affect transcription across the CAG transgene (FIG. 15B). All mice treated 4-times are shown in FIG. 25A-25H. Panel B of FIG. 6 shows the effect of one, two or four NA injections, reflected by Contraction and Expansions instability indices, calculated as described (Lee et al., 2010, BMC Syst. Biol., 4:29) (see, also, FIG. 27). Panel C of FIG. 6 shows the effect of one, two or four NA injections reflected by Relative composition of contractions and expansions, calculated as described (see also FIG. 27). Panel D of FIG. 6 is CAG length analysis showing the distribution of CAG repeat lengths in striatum, frontal cortex, cerebellum and tail from one representative R6/2 mouse (mouse vi) following four injections of NA into the left striatum over a four-week period. DNAs were isolated from the left (blue) and right (red) sides of striatum, frontal cortex, and cerebellum, and from the tail before (red) and after (green) NA treatment. Notably, CAG repeats in the NA-treated half of the striatum were shorter than the inherited length in the tail (estimated progenitor allele length based upon the CAG length in the tail, as this length does not change from birth over the life of the mice; ePAL=159). Repeat size change brackets, with the first number representing the NA-induced contractions of the major peak relative to the somatic expansions without NA, and the second number representing the contractions relative to the inherited allele. These brackets do not account for the size changes in the second mode of the bimodal distribution in the striatum (see also FIG. 25A-25H). Panel E of FIG. 6 shows the Instability Indices in various tissues shown in D, where red and blue diamonds represent values of saline-treated/right side and NA-treated/left side of the striatum, respectively (see also FIG. 25A-25H & FIG. 27B). Panel F of FIG. 6 shows the repeat-tract lengths of the Mapkap1 and Fgd4 loci in both sides of striatum from R6/2 mouse with four injections (see also FIGS. 12A & 12C). Length variation was not observed at any of these repeats of normal length.
Figure 25:
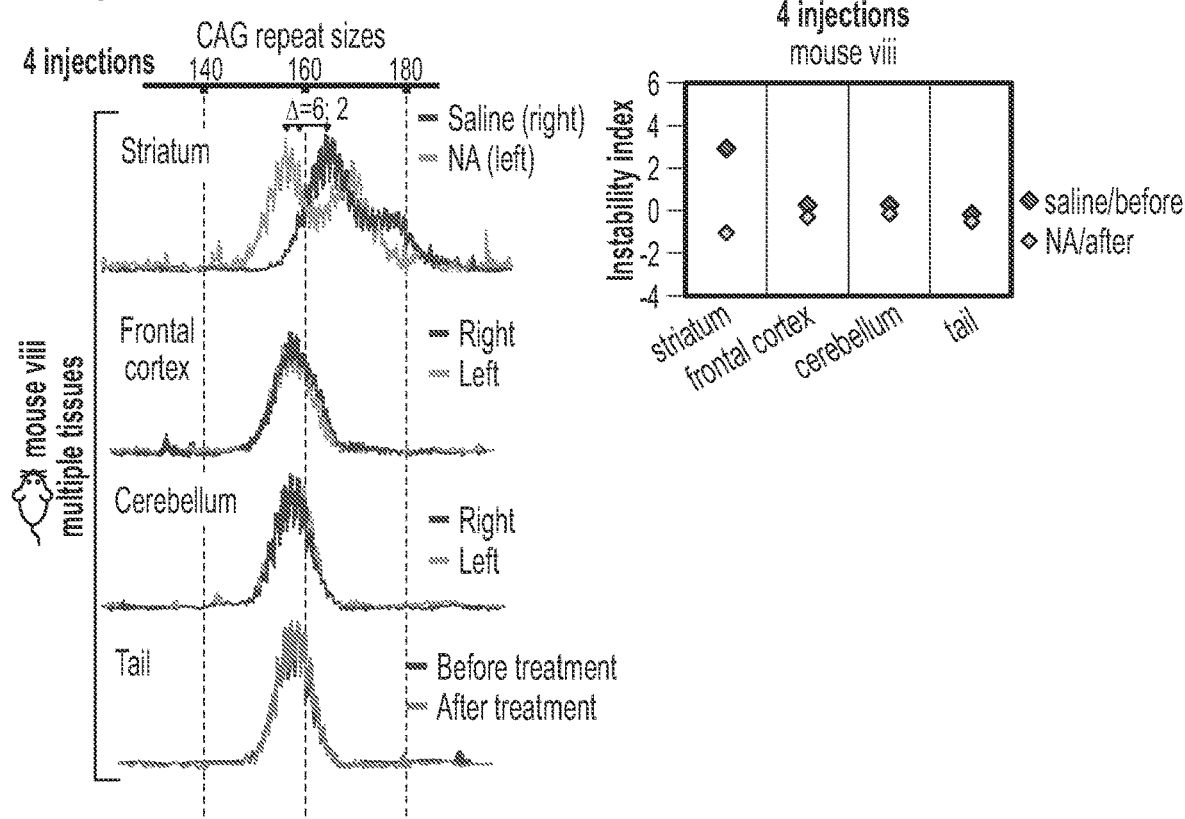
Figure 25:
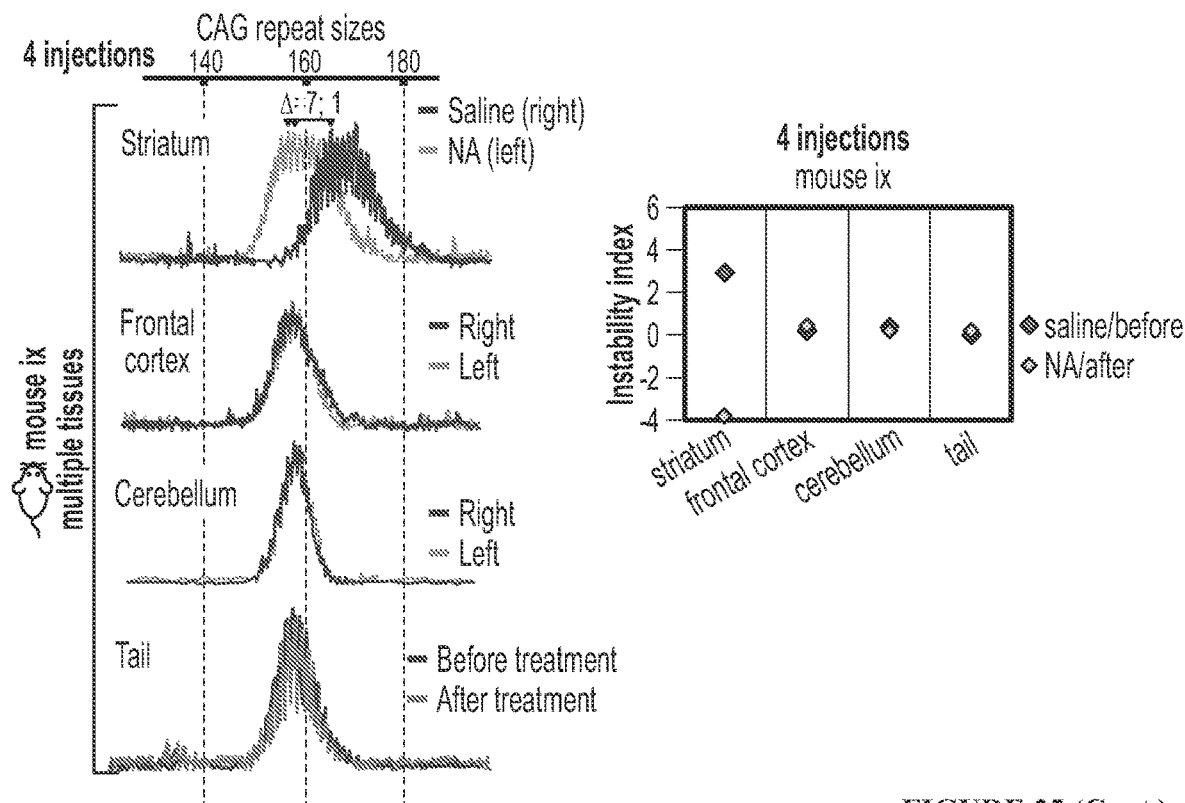
Figure 25:
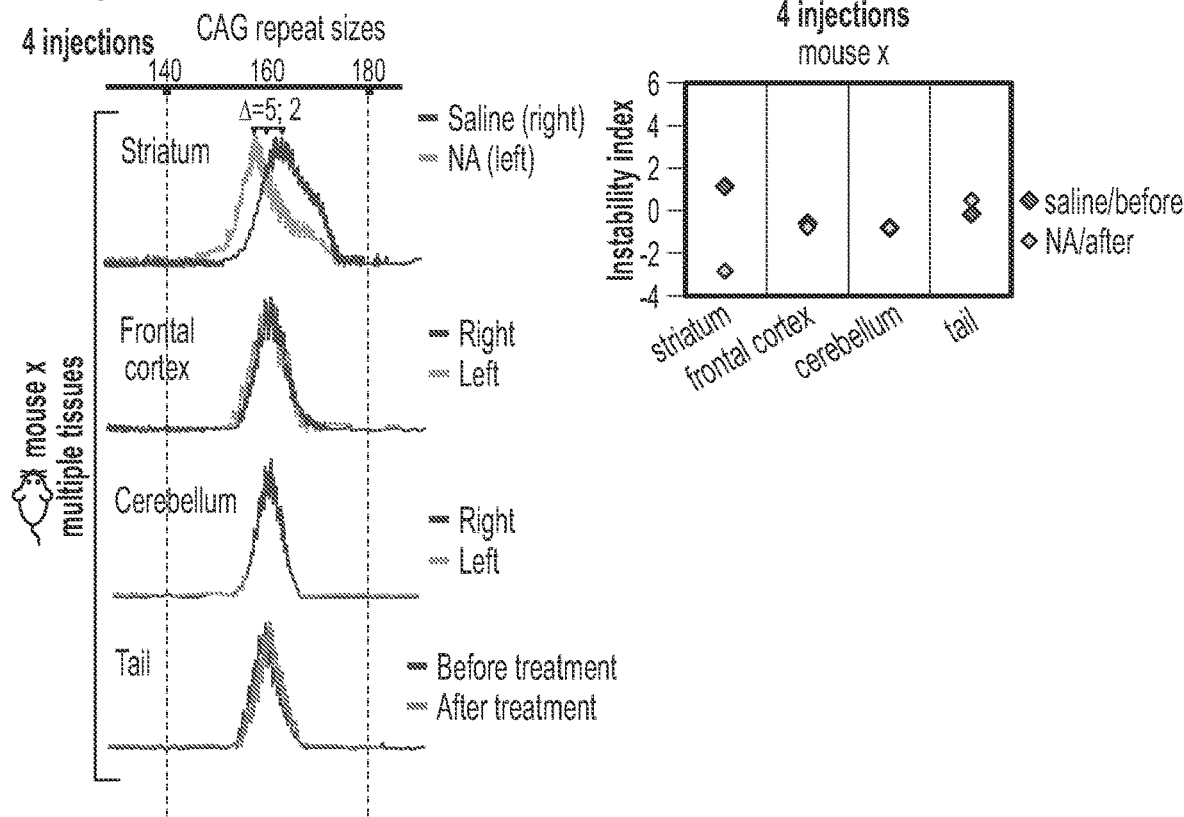
Figure 25:
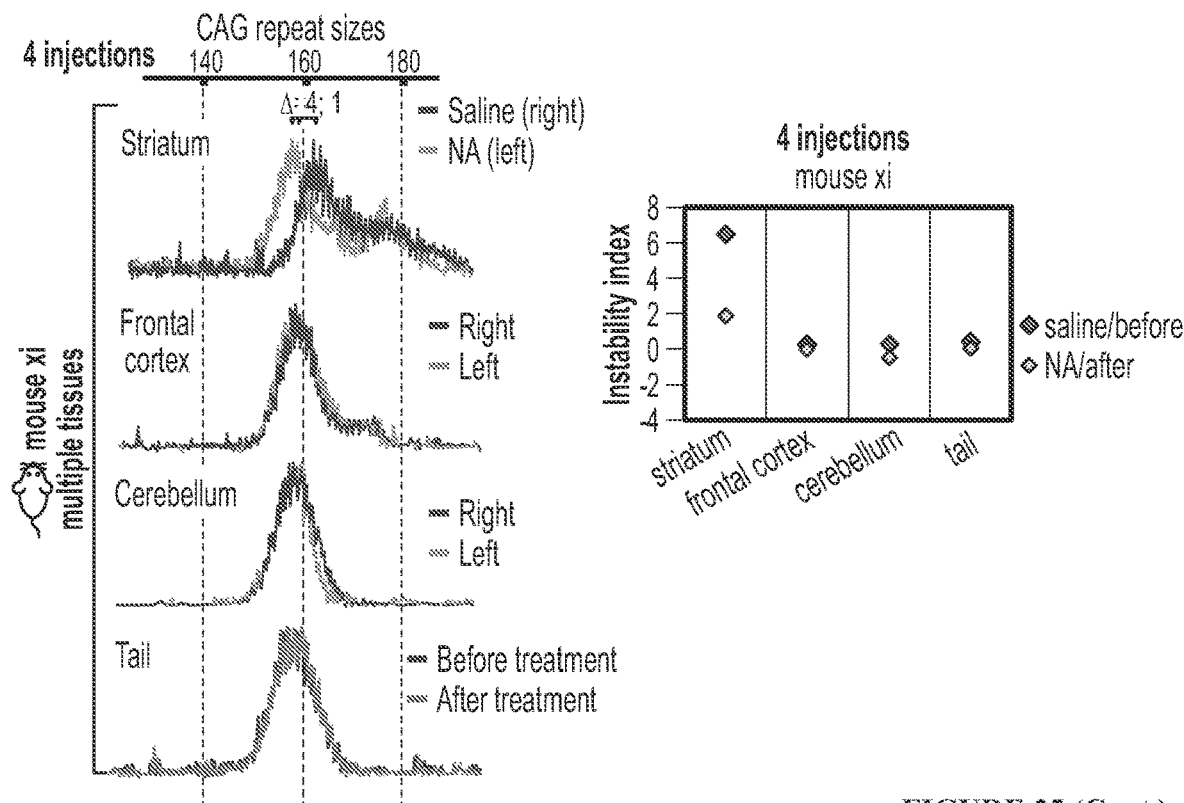
Figure 25:
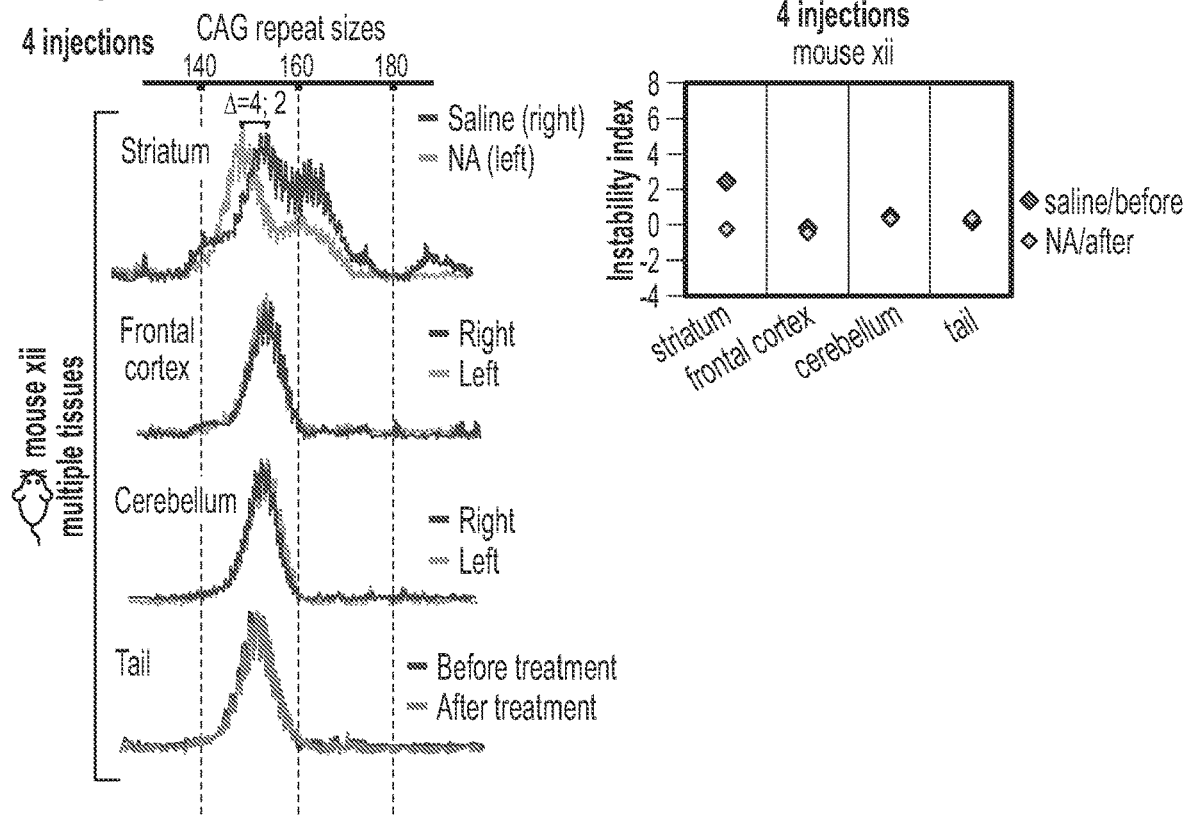
Figure 25:
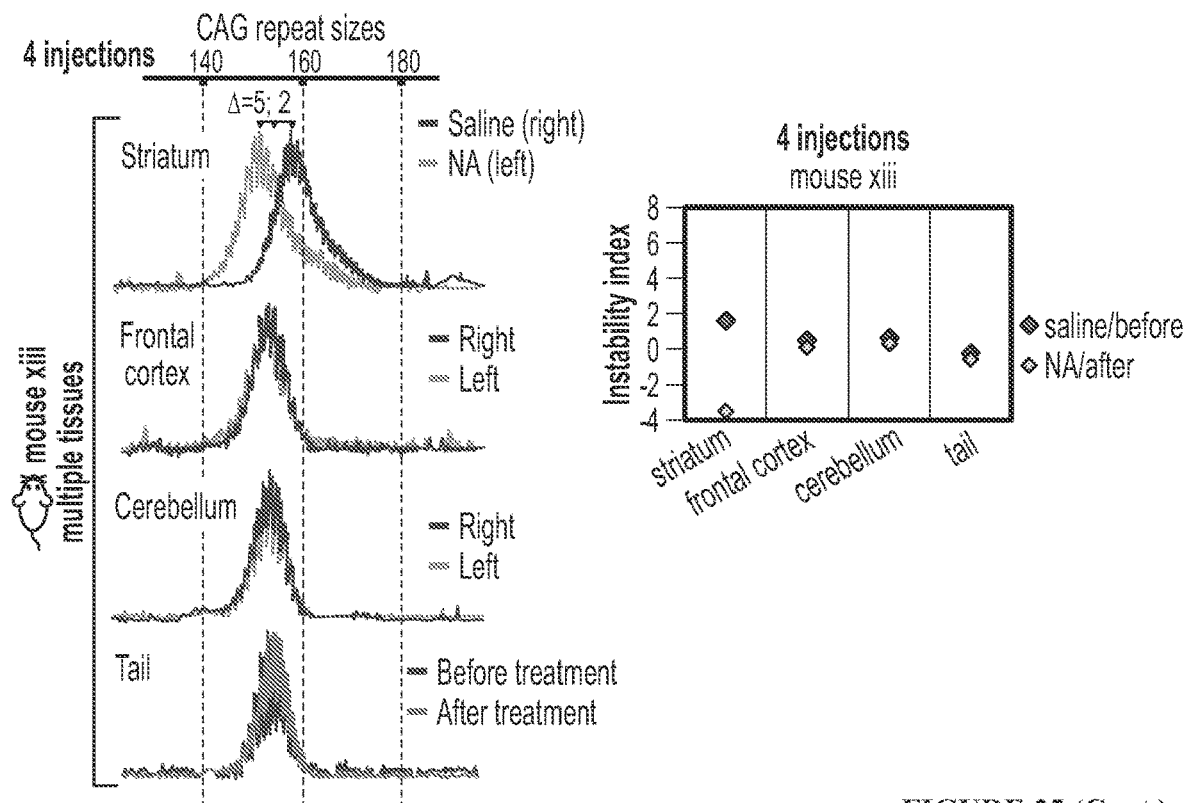

FIG. 25 show CAG repeat length analysis and instability indices for the striatum, cortex, cerebellum and tail of eight of the ten mice treated with 4 injections (mice vi-xii) (Panels A-H of FIG. 25). The CAG scans of the other two mice (mice iv and v) are shown in FIG. 6A.

Figure 26:
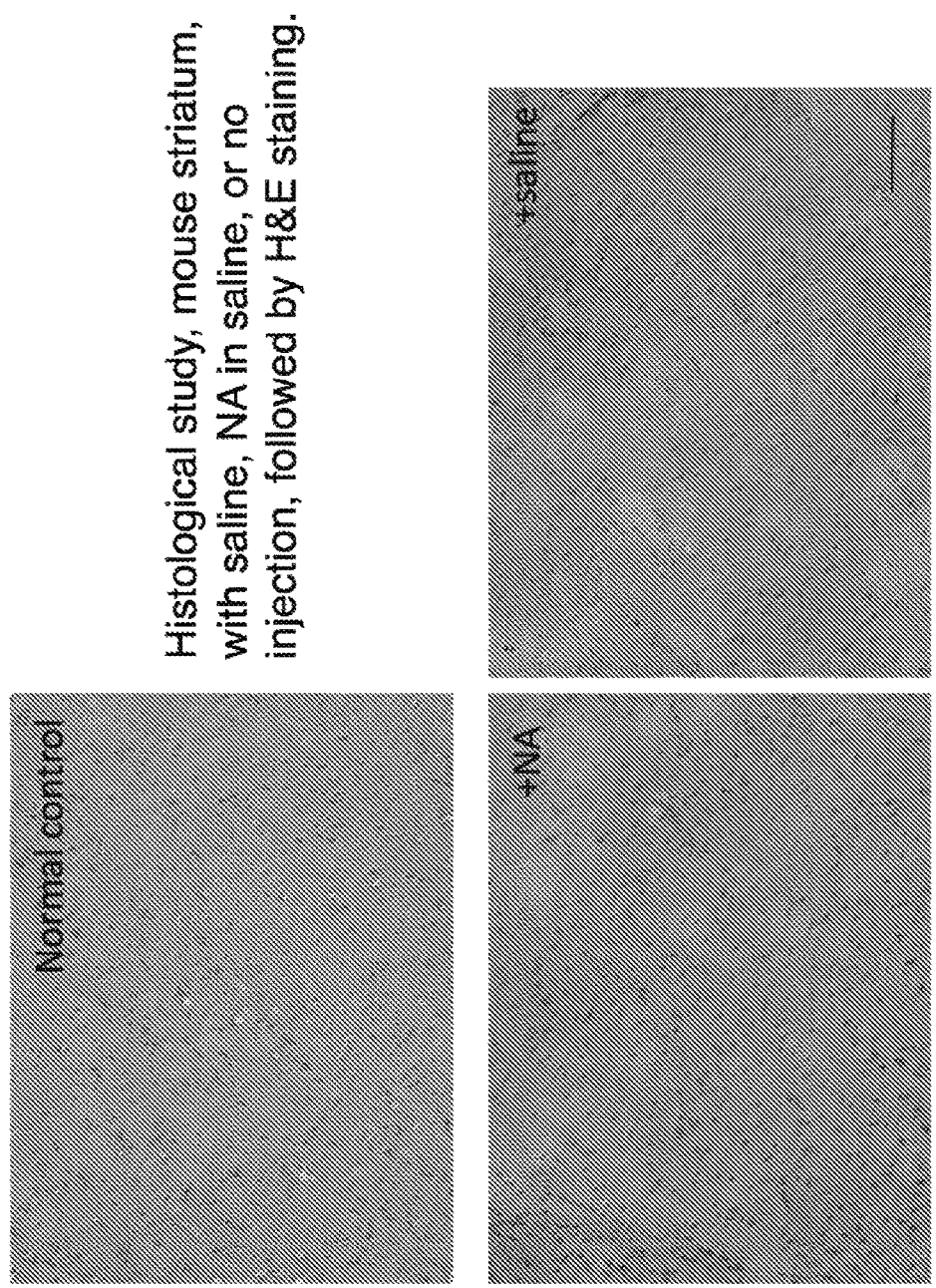

FIG. 26 shows histological study, mouse striatum, with saline, NA in saline, or no injection, followed by H&E staining.

Figure 27A:
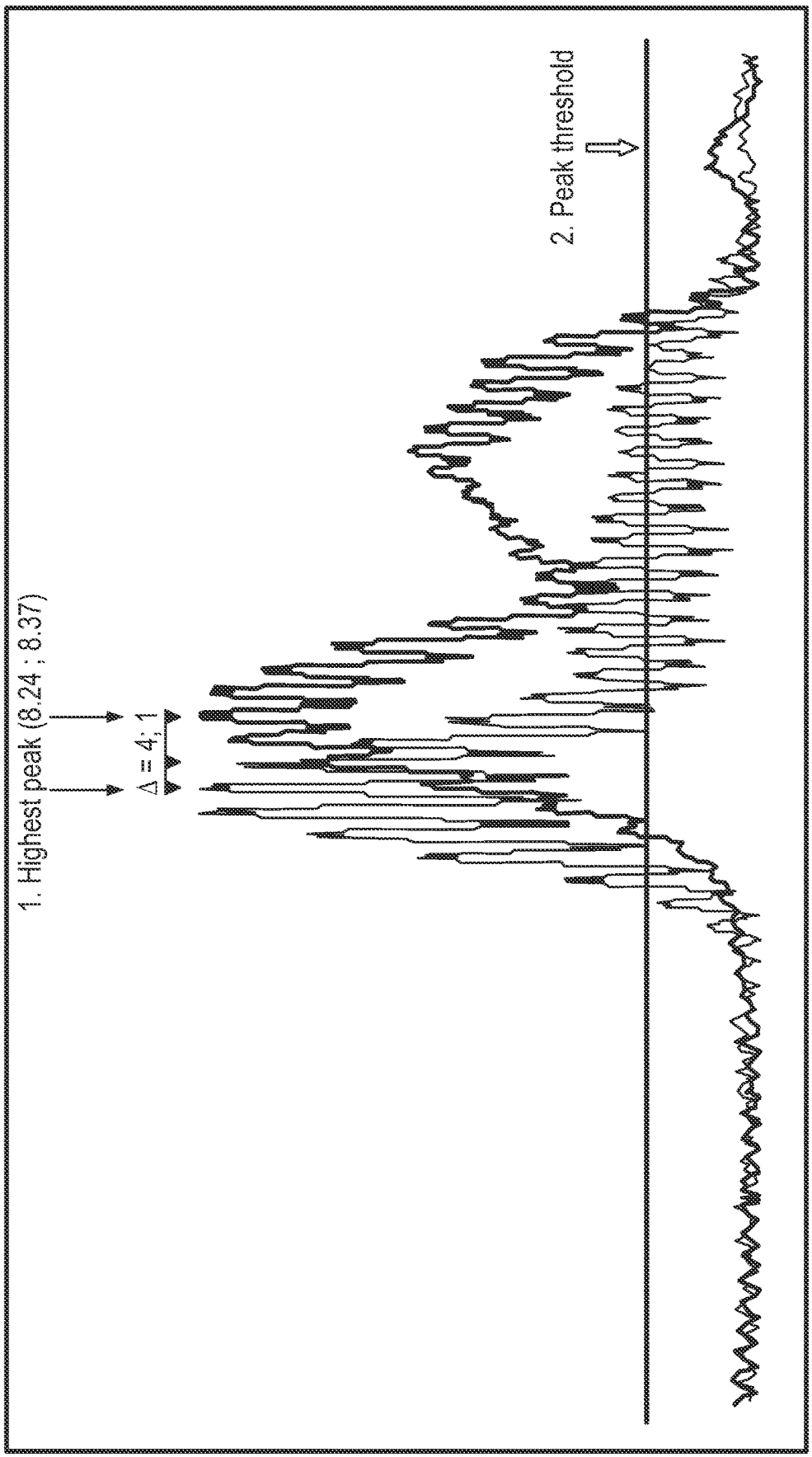
Figure 27B:
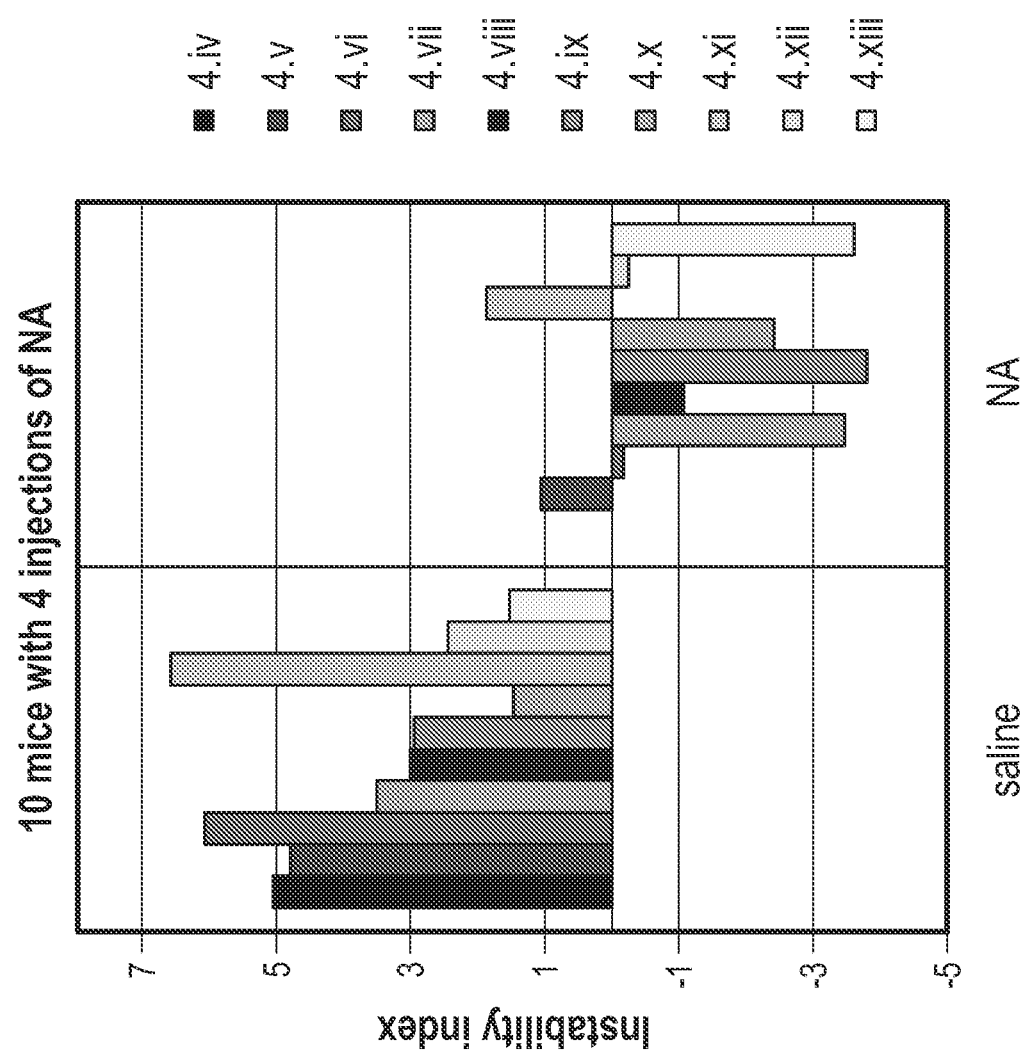

FIG. 27 shows that, most, if not all alleles in the NA-treated striatum had incurred repeat contractions, indicating that NA had affected most cells. Panel A of FIG. 27 shows the quantification of the somatic "instability index" from the gene scan traces of CAG repeat sizes using an established method. This calculation corrects background using a relative height threshold and normalizes data efficiently, generating an "instability index" that represents the mean CAG length change from the main allele per cell in a population of cells: greater indices reflect greater expansions, lower indices-lower expansions. Analysis of striatum treated with and without NA revealed instability indexes that were progressively reduced with subsequent NA injections of 1, 2 and 4 administrations (FIG. 6B, FIG. 25A-25H). Panel B shows the Instability Indices summarized for all ten mice treated 4-times with NA. The repeat size distributions in striatum treated four times with NA were significantly different from the mock-treated striatum (Mann-Whitney, p=0.00035). The relative peak height correction permitted quantification of a contraction and expansion index and the relative composition of contracted/expanded peaks, as described—both of which revealed increasing contractions with subsequent NA treatments. The effect of NA was localized to the site of injection, as the CAG tract in the cerebral cortex and cerebellum from the same mice that had intra-striatal injections, showed identical patterns of CAG length heterogeneity in the right and left sides (FIG. 6C-D, FIG. 25A-25H).

Figure 28:
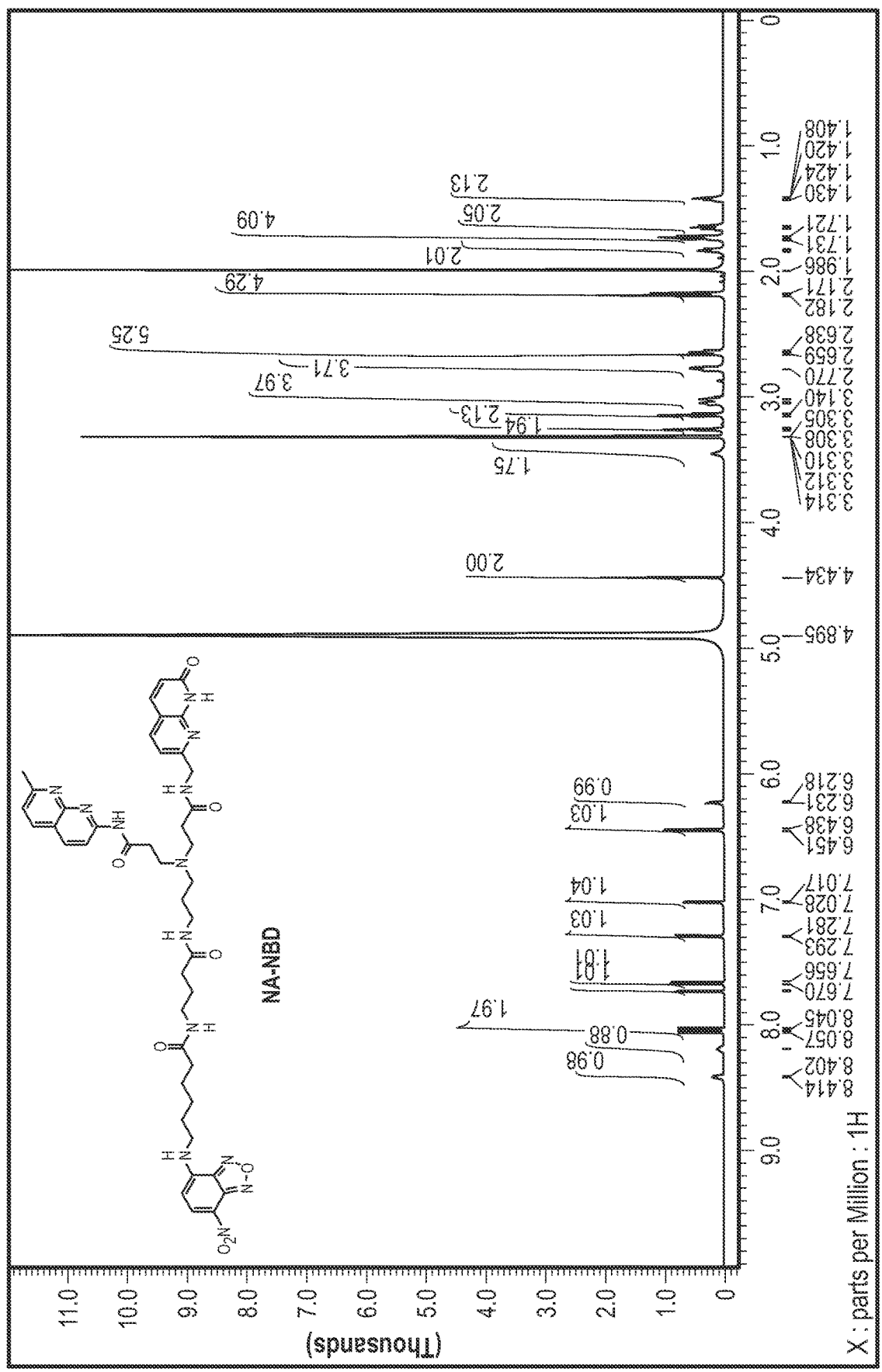

FIG. 28 shows NMR data to confirm the structures of NBD-labeled NA.

DETAILED DESCRIPTION

Small molecules that specifically target genetically unstable disease-causing repeat DNA sequences, or structures that form as a result of these sequences, can have the potential to control their genetic instability, as ongoing somatic repeat expansions can contribute to disease onset and progression. Ligands designed for therapeutic application must bind their target with high specificity for the mutant allele, and arrest expansions or induce contractions with little to no overall toxicity. This disclosure describes small molecules designed to bind specifically to slipped-CAG/CTG repeat structures (Nakatani et al., 2005, Nat. Chem. Biol., 1:39-43; Hagihara et al., 2006, Nuc. Acids Symp. Ser. (Oxf.), 50:147-8; and Hagihara et al., 2011, Chembiochem., 12:1686-9), and modify instability of the expanded repeat, leading to repeat contractions. This disclosure describes the first potential therapy that specifically reduces repeat expansions. Specifically, it is reported herein that NA can arrest expansions, which may slow or arrest disease onset, progression or severity, as well as induce contractions of the expanded repeat, possibly even below the inherited length.

This disclosure describes methods for reducing the number of trinucleotide repeats within a trinucleotide repeat DNA sequence in an individual. This disclosure also describes methods that can be used to inhibit the expansion, or further expansion, of a trinucleotide repeat DNA sequence in an individual. The methods described herein can be used to treat an individual having a disease caused by a trinucleotide repeat DNA instability. As used herein, treating a disease caused by a trinucleotide repeat DNA instability can refer to arresting or halting the progression of the expansion and, hence, the symptoms associated with expansion of the trinucleotide repeat DNA sequence. Also as used herein, treating a disease caused by a trinucleotide repeat DNA instability can refer to reversing progression of the disease. For example, if the number of trinucleotide repeats within a trinucleotide repeat DNA sequence can be reduced to within or below a threshold number, the symptoms associated with the disease can be halted, or prevented, or possibly even reversed to some extent given early intervention (e.g., prior to significant degeneration of cells and tissues).

The methods described herein include administering at least one dose of a therapeutic amount of naphthyridine-azaquinolone (NA) to the individual. NA consists of a 2-amino-1,8-naphthyridine moiety and an 8-azaquinolone moiety (see, for example FIG. 1A). Two molecules of NA intercalate into the DNA helix, with the 2-amino-1,8-naphthyridine moiety available for hydrogen bonding to guanine and the 8-azaquinolone moiety available for hydrogen bonding to adenine, which results in two cytosines being extruded or pushed out of the helix. Without being bound by any particular theory, the results presented herein indicate that NA acts in post-mitotic cells during transcription of the mutant repeat, is specific for the expanded mutant allele, and is mediated by modulating the repair of CAG slip-outs.

Diseases that are caused by trinucleotide repeat instability are known in the art, and currently number in the dozens. The trinucleotide repeat instability diseases that can be treated with NA as described herein include the diseases associated with the CAG/CTG trinucleotide repeats. Such diseases include, without limitation, Huntington's disease (HD), Huntington's disease-like 2 (HDL2), myotonic dystrophy (DM1), Spinocerebellar ataxia type 1 (SCA1), SCA2, SCA3, SCA4, SCA6, SCA7, SCA8, SCA12, SCA17, Spinal and bulbar muscular atrophy (SBMA), Dentatorubropallidoluysian atrophy (DRPLA), Fuch's Endothelial Corneal Dystrophy 2 (FECD2), schizophrenia, bipolar disorder (KCNN3), breast cancer risk factor AIB1 (also known as NCOA3, SRC-3, ACTR, pCIP, RAC3, and TRAM1). Individuals having a disease caused by a trinucleotide repeat DNA instability typically are identified using genetic analysis (e.g., PCR amplification, sequencing, restriction digest analysis, restriction fragment length polymorphisms) to determine the size of the repeat (e.g., the number of trinucleotide repeats) and/or the presence of an expanded region (e.g., an expansion).

NA can be formulated with a pharmaceutically acceptable carrier for delivery to an individual in a therapeutic (or effective) amount. The particular formulation and the therapeutic amount is dependent upon a variety of factors including the route of administration, the dosage and dosage interval of the NA, the sex, age, and weight of the individual being treated, the severity of the affliction, and the judgment of the individual's physician.

Determining the developmental timing of somatic expansions in a given tissue (skeletal muscle, heart, brain regions, etc.) may enhance the ability to administer NA in a way that prevents the onset of somatic expansions and/or more easily induces contractions to lengths closer to the non-affected lengths.

As used herein, "pharmaceutically acceptable carrier" is intended to include any and all excipients, solvents, dispersion media, coatings, antibacterial and anti-fungal agents, isotonic and absorption delaying agents, and the like, compatible with administration. The use of such media and agents for pharmaceutically acceptable carriers is well known in the art. Except insofar as any conventional media or agent is incompatible with a compound, use thereof is contemplated.

Pharmaceutically acceptable carriers for delivering compounds are well known in the art. See, for example *Remington: The Science and Practice of Pharmacy*, University of the Sciences in Philadelphia, Ed., 21$^{st}$ Edition, 2005, Lippincott Williams & Wilkins; and *The Pharmacological Basis of Therapeutics*, Goodman and Gilman, Eds., 12$^{th}$ Ed., 2001, McGraw-Hill Co. The type of pharmaceutically acceptable carrier used in a particular formulation can depend on various factors, such as, for example, the physical and chemical properties of the compound, the route of administration, and the manufacturing procedure. Pharmaceutically acceptable carriers are available in the art, and include those listed in various pharmacopoeias. See, for example, the U.S. Pharmacopeia (USP), Japanese Pharmacopoeia (JP), European Pharmacopoeia (EP), and British pharmacopeia (BP); the U.S. Food and Drug Administration (FDA) Center for Drug Evaluation and Research (CDER) publications (e.g., Inactive Ingredient Guide (1996)); and Ash and Ash, Eds. (2002) Handbook of Pharmaceutical Additives, Synapse Information Resources, Inc., Endicott, N.Y.

A pharmaceutical composition that includes NA as described herein is typically formulated to be compatible with its intended route of administration. Suitable routes of administration include, for example, oral, rectal, topical, nasal, pulmonary, ocular, intestinal, and parenteral administration. Routes of parenteral administration include intravenous, intramuscular, and subcutaneous administration, as well as intraperitoneal, intra-arterial, intra-articular, intracardiac, intracisternal, intradermal, intralesional, intraocular, intrapleural, intrathecal, intrauterine, and intraventricular administration.

Simply by way of example, for intravenous injection, the NA may be formulated as an aqueous solution using physiologically compatible buffers, including, for example, phosphate, histidine, or citrate for adjustment of the formulation pH, and a tonicity agent, such as, for example, sodium chloride or dextrose. For oral administration, NA can be formulated in liquid or solid dosage forms, and also formulated as an instant release or controlled/sustained release formulations. Suitable forms for oral ingestion by an individual include tablets, pills, hard and soft shell capsules, liquids, gels, syrups, slurries, suspensions, and emulsions. Solid oral dosage forms can be obtained using excipients, which can include fillers, disintegrants, binders (dry and wet), dissolution retardants, lubricants, glidants, anti-adherents, cationic exchange resins, wetting agents, antioxidants, preservatives, coloring, and flavoring agents. Examples of such excipients include cellulose derivatives, citric acid, dicalcium phosphate, gelatine, magnesium carbonate, magnesium/sodium lauryl sulfate, mannitol, polyethylene glycol, polyvinyl pyrrolidone, silicates, silicium dioxide, sodium benzoate, sorbitol, starches, stearic acid or a salt thereof, sugars (e.g., dextrose, sucrose, lactose), talc, tragacanth mucilage, vegetable oils (hydrogenated), and waxes.

NA can be administered topically, such as through a skin patch, a semi-solid, or a liquid formulation, for example a gel, a (micro-) emulsion, an ointment, a solution, a (nano/micro)-suspension, or a foam. Penetration of NA into the skin and underlying affected tissues can be regulated, for example, using penetration enhancers; the appropriate choice and combination of lipophilic, hydrophilic, and amphiphilic excipients, including water, organic solvents, waxes, oils, synthetic and natural polymers, surfactants, emulsifiers; by pH adjustment; and/or the use of complexing agents.

NA can be administered in a therapeutic amount to an individual having a disease caused by trinucleotide repeat DNA instability. Typically, a therapeutic amount or dose of NA refers to the amount of NA that results in either arresting somatic expansions, or a reduction in the inherited size of the trinucleotide repeat DNA sequence (e.g., a reduction in the number of trinucleotide repeats) and, eventually, a reduction in, or amelioration of, one or more symptoms without inducing any adverse effects. In some instances, the therapeutic amount correlates with the number of repeats present. Toxicity and therapeutic efficacy of NA can be determined by standard pharmaceutical procedures in cell cultures or experimental animals, e.g., by determining the LD50 (the dose lethal to 50% of the population) and the ED50 (the dose therapeutically effective in 50% of the population). The dose ratio of toxic to therapeutic effects is the therapeutic index, which can be expressed as the ratio LD50/ED50.

A therapeutic amount of NA can be administered in a single dose (i.e., a one-time dose) or a therapeutic amount of NA can be administered in more than one dose (i.e., a plurality of times) or even in a slow, continuous manner using, for example, a pump or a patch. As used herein, a therapeutic amount of NA refers to about 0.01 μM to about 1 M (e.g., about 0.05 uM to about 0.75 M; about 0.1 uM to about 0.5 M; about 0.5 uM to about 0.1 M; about 1 uM to about 50 mM; about 50 uM to about 1 mM; or about 100 uM to about 0.5 mM) of NA. In some embodiments, the concentration of NA in a composition as described herein can be between about 1% and about 50% (e.g., between about 5% and about 40%; between about 10% and about 30%; between about 15% and about 25%; or about 20%). In some instances, NA can be administered in a dose-dependent manner depending upon the number of trinucleotide repeats a person has inherited, or the rate of somatic expansions in a given tissue. It would be appreciated that, depending upon the disease, the severity of the symptoms, and the number of trinucleotide repeats, a therapeutic amount of NA (e.g., in one or more doses) can be administered once a week, once a month, once a year, or more or less frequently as needed (e.g., chronically with an intracranial pump).

It also would be appreciated that, given the tissue-specific expansion exhibited in several of the trinucleotide repeat diseases, the therapeutic amount of NA may differ for different tissues within the same individual. For example, in HD, the primary tissues that exhibit the most expansion (e.g., the largest expansion, the most rapid expansion, or combinations thereof) includes the striatum, the cerebral cortex, the basal ganglia, medium spiny neurons, and the male germline; in myotonic dystrophy type I, the primary somatic tissues that exhibit expansion includes the brain, heart, and the cerebral cortex. For DM1, see, for example, Lopez Castel et al. (2011, Hum. Mol. Genet., 20:1-15) and Seriola et al. (2011, Hum. Mol. Genet., 20:176-85); for Huntington's disease, see, for example, De Rooij et al. (1995, Hum. Genet., 95:270-4) and Telenius et al. (1994, Nat. Genet., 6:409-14); For DRPLA, see, for example, Aoki et al. (1996, Clin. Genet., 50:199-201); for spinal and bulbar muscular atrophy (SBMA), see, for example, Tanaka et al. (1996, J. Neurol. Sci., 135:43-50); for SCA1 and SCA3, see, for example, Cancel et al. (1998, Hum. Mutat., 11:23-7); for SCA7, see, for example, Yoon et al. (2016, Brain, 139(Pt 3):e20). See, also, Cleary & Pearson (2003, Cytogenet. Genome Res., 100:25-55), Abeliovich et al. (1993, Am. J. Hum. Genet., 52:1175-81), Wohrle et al. (1995, Hum. Mol. Genet., 4:1147-53), Peterlin et al. (1996, Pflugers Arch., 431(6 Suppl 2):R199-200), Anvret et al. (1993, Hum. Mol. Genet., 2:1397-400), Thornton et al. (1994, Ann. Neurol., 35:104-7), and Ishii et al. (1996, Hum. Genet., 98:138-40).

The methods described herein also can include the step of monitoring individuals that have received NA. For example, using routine methods in the art (e.g., PCR amplification, sequencing, restriction digest analysis, restriction fragment length polymorphisms), the size of the trinucleotide repeat can be monitored in cells from the individual. The monitoring step can occur with the desired frequency; for example, the individual, or cells from one or more tissues from the individual, can be monitored with the same frequency as the NA is administered (e.g., before or after the NA is administered) or can be monitored at another desired frequency (e.g., weekly, monthly, or yearly). In some instances, the results of the monitoring step can determine, or help determine, the tissue(s) that require treatment, the therapeutic amount, and/or the appropriate frequency with which the therapeutic amount should be delivered to the individual (or to the tissue).

It would be understood that the NA can be modified in a number of ways to increase its stability, tissue-selectivity, uptake, or combinations thereof in vivo. In some instances, the NA can be delivered via, for example, liposomes, an intracranial pump, intramuscular diffusion, a blood-brain barrier "key", or another formulation that stabilizes and/or provides protection for the NA during administration and delivery to the affected cells/tissues.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Characterization of NA-CAG/CAG Complex

Figure 2A:
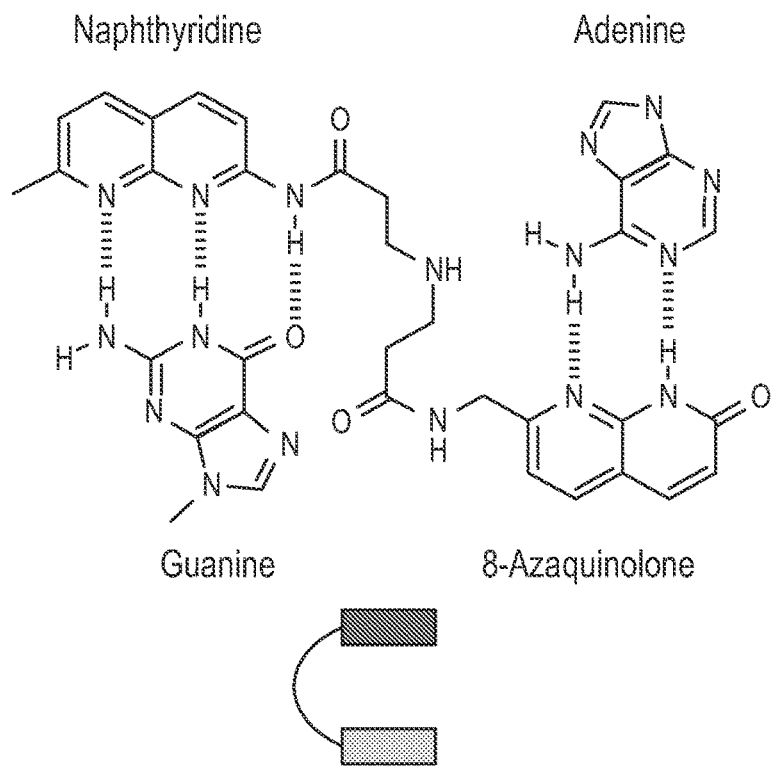
FIG. 2 are the results of experiments showing that NA binds to long CAG slip-outs. Panel A of FIG. 2 shows the structure of NA comprising of two heterocycles, naphthyridine (in red) and 8-azaquinolone moiety (in blue). Panel B of FIG. 2 shows a schematic illustration of the NA-(CAG)●(CAG) triad complex. The (CAG)n DNA sequence (left) can fold into an hairpin structure involving mismatched A-A pair flanking C-G base pairs (middle). NA molecules can intercalate into the DNA helix, with the 2-amino-1,8-naphthyridine moiety (in red) hydrogen bonding to guanine and 8-azaquinolone moiety (in blue) hydrogen bonding to adenine. Panel C of FIG. 2 demonstrates the binding of NA to gel-purified DNA fragments with repeats in both strands flanked by 59 bp and 54 bp of non-repetitive DNA upstream and downstream of the CTG tract $^{32}$P-labeled on both strands, where the repeats are (CAG)50●(CTG)50 in the fully-duplexed form, clustered short slip-outs on (CAG)50●(CTG)50, long (CAG)20 slip-outs from (CAG)50●(CTG)30, or long (CTG)20 slip-outs from (CAG)30●(CTG)50. Long slip-outs extruded as a single slip-out from a fully base-paired backbone of (CTG)n●(CAG)n, as described (Pearson et al., 2002, Nuc. Acids Res., 30:4534-47). DNAs were mixed with increasing concentrations of NA (0.15 µM, 0.75 µM, 7.5 µM and 50 µM) and resolved on 4% polyacrylamide gels. All lanes are from the same gel, and they were separated for clarity. NA-DNA complexes are shown by brackets, free DNA is indicated by arrowheads. For both the linear and the (CTG)20 slip-out DNA, there was no NA binding (white arrowheads); at the higher concentration of NA, a decrease of the clustered short slip-outs DNA was observed (grey arrowheads), but it was not possible to define a clear shifted band; band-shift was evident for the (CAG)20 slip-out DNA (black arrowheads). Panel D of FIG. 2 shows the quantification of NA binding. The relative migration was measured for the linear and the three slip-outs substrates as the ratio of the migration distance of each NA-DNA complex to the migration distance of the free DNA. The migration distance was measured from the well to a consistent center point of each band. Densitometry analysis was performed for the S-DNA substrate. Graphs indicate the mean of three independent experiments and the corresponding standard deviation. Panel E of FIG. 2 shows that the gel-purified DNA heteroduplex fragment with a long (CAG)20 slip-out from (CAG)50●(CTG)30, $^{32}$P-labeled on both strands, was heat denatured, snap-cooled on ice (to enhance intra-strand structure formation and inhibit inter-strand hybridization) and incubated in the presence or absence of 7.5 µM NA (left panel). The same DNAs were denatured by alkaline treatment and then rehybridized in presence or absence of 7.5 µM NA (right panel). DNAs were then resolved on a 4% polyacrylamide gel. Each DNA species is schematically indicated. NA-DNA complexes formed with both the (CAG)50 strand (both panels) and the heteroduplexed (CAG)50●(CTG)30 (right panel) are shown by brackets; free DNA is indicated by arrowheads. NA did not bind the (CTG)30 hairpin fragment in either experiment (white arrowheads). Notably, NA did not inhibit re-hybridization of complementary strands.
Figure 2B:
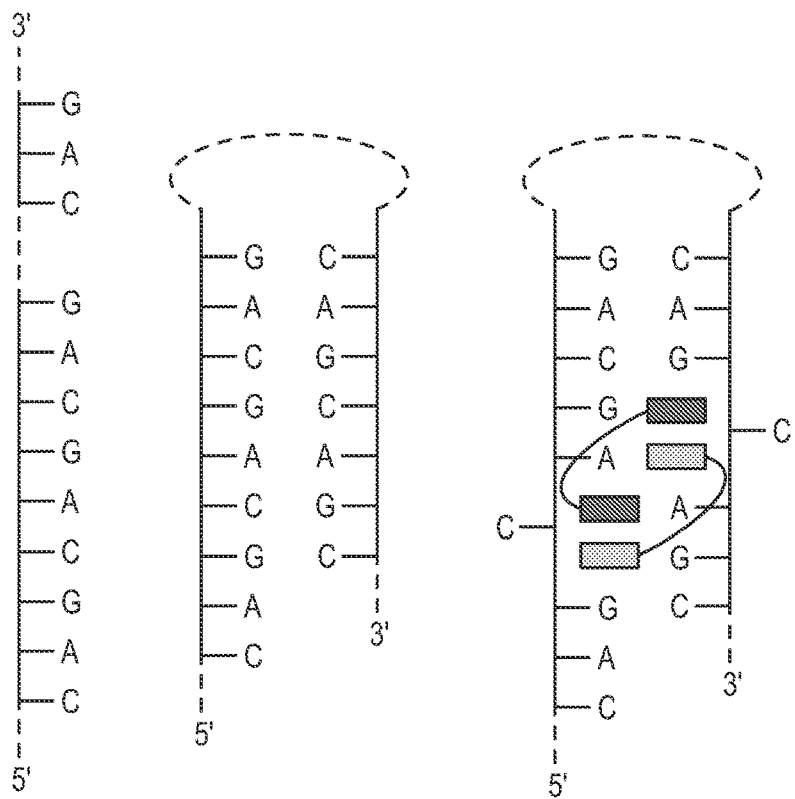

Previous characterizations of the NA-CAG used UV-melting, electrospray ionization time-of-flight mass spectrometry (ESI-TOF MS), isothermal titration calorimetry (ITC), surface plasmon resonance (SPR) assay, circular dichroism (CD) spectroscopy, SPR-imaging assay, and nuclear magnetic resonance (NMR) spectroscopy (Hagihara et al., 2006, Nuc. Acids Symp. Ser. (Oxf.), 50:147-8; Nakatani et al. 2005, Nat. Chem. Biol., 1:39-43; Hagihara et al., 2011, Chem. Bio. Chem., 12:1686-9). These studies revealed a unique NA-(CAG)●(CAG) structure of a distorted intra-strand hairpin. The naphthyridine and azaquinolone moieties in NA exhibit complementary hydrogen bonding to guanine and adenine, respectively, causing two cytosine bases to flip-out from the CAG hairpin (FIGS. 2A and 2B). The affinity of each NA molecule/CAG-CAG was estimated to be $1.8 \times 10^6$ $M^{-1}$ as Ka or $0.56 \times 10^{-6}$ M as Kd (Hagihara et al., 2006, Nuc. Acids Symp. Ser. (Oxf.), 50:147-8). NA increased the melting temperature of $(CAG)_{10}$ hairpins from 47.1 ($\pm 0.7$)° C. to 78.8 ($\pm 0.1$)° C. at 50 μM NA, surpassing the melting temperature of $(CTG)_{10}$ hairpins (54.4 ($\pm 0.3$)° C.). A large structural change of $d(CAG)_{10}$ shown by CD spectroscopy and SPR-imaging assay was induced by multiple NA-binding (at least 6 NA molecules) to the repeat as confirmed by ESI-TOF MS. NA-binding increased for longer repeats with isolated short oligonucleotides of (CAG)10-30 (Nakatani et al., 2005, Nat. Chem. Biol., 1:3943). The NA-CAG/CAG bound structure was determined by NMR spectroscopy, and this structure was deposited in the Protein Data Bank (PDB) and assigned Accession Number 1×26. These features explain the remarkable selectivity of NA for CAG hairpins; both sequence- and hairpin-specificity likely target the CAG/CTG expanded allele.

Example 2—NA Synthesis and Labeling

Solvents and starting materials were purchased by the standard suppliers and used without further purification. Analytical thin-layer chromatography (TLC) was performed on 0.2 mm silica 60 coated on plates with F254 indicator. Flash column chromatography was performed on Wako gel C-200 silica gel. High performance liquid chromatography (HPLC) was performed by a Gilson 811C Dynamic Mixer system with a UV detector set at 254 nm using a Cosmosil 5C18-MS-II column (150×20 mm) with a dual solvent system of 0.1% HOAc/$H_2O$ (Solvent A) and MCCN (Solvent B). Nuclear magnetic resonance (NMR) spectra were recorded on a Bruker Avance III 700 spectrometer at 21±3° C. unless otherwise indicated. Chemical shifts (δ) are reported in parts per million (ppm). Coupling constants (J) were reported in Hertz. $^1H$ NMR chemical shifts were referenced to the residual solvent peak at 3.31 ppm in CD3OD-d4. $^{13}C$ NMR chemical shifts were referenced to the center solvent peak at 49.00 ppm for CD3OD. ESI mass spectra were recorded on a Thermo LTQ Orbitrap XL mass spectrometer.

4-amino-N-(3-((3-((7-methyl-1,8-naphthyridin-2-yl)amino)-3-oxopropyl)(3-oxo-3-(((7-oxo-7,8-dihydro-1,8-naphthyridin-2-yl)methyl)amino)propyl)amino)propyl)butanamide (NA-Linker)

NA (40 mg, 0.09 mmol) and tert-butyl (4-oxo-4-((3-oxopropyl)amino)butyl)carbamate (34 mg, 0.13 mmol) was stirred in methanol (2 mL). Acetic acid was added to adjust the pH of the mixture about to 6. Then, sodium triacetoxyborohydride (31 mg, 0.13 mmol) was added to the mixture. The mixture was stirred at room temperature for 12 h. The solvent was evaporated to dryness, and the residue was purified by column chromatography on silica gel eluted with chloroform:methanol=50:1 to give Boc-NA-Linker (15 mg, 25%) as pale yellow solids. To a solution of Boc-NA-Linker (15 mg, 0.02 mmol) in chloroform (1 mL) was added ethyl acetate containing 4 M HCl (0.5 mL), and the reaction mixture was stirred at room temperature for 0.5 h. The solvent was evaporated to dryness. The residue was further purified by HPLC to give NA-Linker (11 mg, 86%) as white solids. $^1$H NMR (CD$_3$OD, 700 MHz): delta=8.20 (d, J=8.6 Hz, 1H), 8.06 (dd, J=8.4, 2.4 Hz, 2H), 7.76-7.60 (m, 2H), 7.33 (d, J=8.2 Hz, 1H), 7.02 (d, J=7.7 Hz, 1H), 6.43 (d, J=9.5 Hz, 1H), 4.42 (s, 2H), 3.26 (t, J=6.9 Hz, 2H), 3.01 (t, J=7.3 Hz, 2H), 2.92 (t, J=6.0 Hz, 2H), 2.87 (t, J=6.0 Hz, 2H), 2.70 (t, J=6.0 Hz, 2H), 2.69 (s, 3H), 2.63 (t, J=7.1 Hz, 2H), 2.56 (t, J=6.0 Hz, 2H), 2.37 (t, J=6.9 Hz, 2H), 1.93 (t, J=7.3 Hz, 2H), 1.76 (t, J=7.1 Hz, 2H). $^{13}$C NMR (CD$_3$OD, 175 MHz): delta=175.4, 174.1, 173.2, 172.9, 164.4, 162.8, 159.8, 153.7, 153.6, 148.3, 139.5, 138.8, 137.3, 136.6, 121.5, 120.9, 118.3, 115.8, 114.1, 113.1, 51.3, 50.4, 49.4, 44.3, 39.0, 37.2, 34.5, 33.7, 32.4, 26.3, 23.6, 23.0. HRMS (ESI) m/z: calcd for $[C_{31}H_{39}N_9O_4+Na]^+$, 624.3024; found, 624.3010.

N-(4-((3-((3-((7-methyl-1,8-naphthyridin-2-yl)amino)-3-oxopropyl)(3-oxo-3-(((7-oxo-7,8-dihydro-1,8-naphthyridin-2-yl)methyl)amino)propyl)amino)propyl)amino)-4-oxobutyl)-6-((7-nitrobenzo[c][1,2,5]oxadiazol-4-yl)amino)hexanamide (NA-NBD)

NA-Linker (15 mg, 0.02 mmol) and NBD-X, SE (Succinimidyl 6-(N-(7-nitrobenz-2-oxa-1,3-diazol-4-yl)amino)hexanoate) (12 mg, 0.03 mmol) was stirred in dimethylformamide (3 mL). Then, triethylamine (5 mg, 0.05 mmol) was added to the mixture. The mixture was stirred at room temperature for 6 h. The solvent was evaporated to dryness, and the residue was purified by column chromatography on silica gel eluted with chloroform:methanol=20:1 to give crude product. The crude product was further purified by HPLC to give NA-NBD (13 mg, 59%) as white solids. $^1$H NMR (CD$_3$OD, 700 MHz): delta=8.41 (d, J=8.6 Hz, 1H), 8.18 (bs, 1H), 8.04 (q, J=8.3 Hz, 2H), 7.73 (d, J=8.2 Hz, 1H), 7.66 (d, J=9.5 Hz, 1H), 7.29 (d, J=8.2 Hz, 1H), 7.02 (d, J=8.2 Hz, 1H), 6.44 (d, J=9.5 Hz, 1H), 6.22 (d, J=9.0 Hz, 1H), 4.43 (s, 2H), 3.44 (s, 2H), 3.26 (t, J=6.9 Hz, 2H), 3.14 (t, J=7.1 Hz, 2H), 3.09-2.97 (4H), 2.77 (s, 4H), 2.66 (s, 3H), 2.64 (t, J=6.3 Hz, 2H), 2.18 (t, J=7.5 Hz, 4H), 1.83 (t, J=7.1 Hz, 2H), 1.76-1.70 (4H), 1.65 (t, J=7.5 Hz, 2H), 1.47-1.37 (2H). $^{13}$C NMR (CD$_3$OD, 175 MHz): delta=174.6, 174.2, 174.1, 173.5, 172.3, 164.4, 162.8, 159.8, 153.7, 153.6, 148.3, 145.1, 144.4, 144.0, 139.5, 138.7, 137.2, 136.6, 121.4, 121.0, 118.3, 115.8, 114.2, 113.1, 98.1, 51.2, 50.0, 49.3, 44.3, 43.1, 38.5, 38.3, 36.9, 35.4, 33.5, 33.0, 32.6, 27.5, 26.1, 25.8, 25.4, 25.1, 23.6. HRMS (ESI) m/z: calcd for $[C_{43}H_{51}N_{13}O_8+Na]^+$, 900.3883: found, 900.3875.

These reactions are shown in FIG. 1B, and the structure of the NBD-labeled NA was confirmed by NMR (FIG. 28).

Example 3—Cell Culture

The construction of the HT1080-(CAG)850 cell model was described previously (Sathasivam et al., 1997, Hum. Genet., 99:692-5). Briefly, HT1080 (ATCC) human fibrosarcoma cells were co-transfected with a plasmid (LC15-R) containing 800-850 (CTG)●(CAG) repeats (Nakatani et al., 2005, Nat. Chem. Biol., 1:39-43) and a plasmid encoding PhiC31 integrase. Transfection was performed with a Nucleofector (Lonza, Basel, Switzerland), and stably transfected clones were selected with puromycin. The HT1080-non transcribing (CAG)$_{850}$ cell model was established by transfecting a plasmid modified from pLC16 by adding a SV40 polyadenylation signal downstream of the repeats, instead of LC15-R. The HT1080-non-transcribing (CAG) 850 cell model was established by transfecting a plasmid modified from pLC16 by inserting an additional SV40 polyadenylation signal downstream of the repeats (in addition to the original polyadenylation signals located upstream of the repeats), so that CAG/CTG repeats are floxed by transcription-terminator elements. The AttB-PhiC31 system has been widely used for single copy integration. As expected, this AttB-PhiC31-mediated integration resulted in a confirmed single integration of the transgene, that was only transcribed only when induced (FIG. 16A). The HT1080 model cells and an HD primary fibroblast cell line, GM09197 (Coriell Biorepository) with a large expanded allele of 180 CAG repeats and a non-expanded allele of 23 repeats (Sathasivam et al., 1997, Hum. Genet., 99:6692-5), the HD primary fibroblast cell line, GM02191 (Coreill Biorepository) with an expanded allele of 43 CAG repeats and a non-expanded allele of 19 repeats, were cultured at 37° C. with 5% CO$_2$ in Dulbecco's modified Eagle's medium supplemented with 10% fetal bovine serum and 1% penicillin/streptomycin. Cells were treated with or without continuous exposure to 50-μM NA for 30 days (HT1080 cells) or for 40 days (fibroblast cells). For experiments on non-proliferating cells, HT1080 cells were grown to confluence and then treated for the same period. WST-1 assay was performed according to the manufacturer's instructions (Roche, Basel, Switzerland). All cell lines were tested to be free of *Mycoplasma*. Three biological replicates were performed for each experiment.

Proliferation was inhibited by growth under contact inhibition and serum starvation, as previously performed. Degree of arrest from proliferation was assessed in living cells by counting BrdU positive cells after 24 hrs incubation with BrdU in proliferating or contact-inhibited (and serum starved) HT1080-(CAG)850 cells. The percentage of BrdU positive cells was 92.6% in proliferating cells and 8.17% in contact-inhibited cells. Although a small portion of HT1080-(CAG)850 cells were still proliferating even under contact-inhibition and serum starvation, the ratio is very small. Based on a calculation how many cells derive from a single cell after 30 days (the period that was studied) (proliferating, 1.926^30=348653546.6; contact inhibition, 1.0817^30=10.55), the effect of proliferation in contact-inhibited cells can be ignored.

Example 4—Microscopy

HT1080-(CAG)850 cells were incubated with 50-μM NBD-labeled NA for 48 hr and Cell Light Plasma Membrane-RFP, BacMam 2.0 (Life Technologies, Carlsbad, Calif.), then fixed for 15 min at RT with 4% paraformaldehyde and washed 2 times for 10 min in phosphate buffered saline (PBS). Cells were mounted with Vectashield hard-set mounting media that contains DAPI (Vector Laboratories, Burlingame, Calif.). Fluorescence images were obtained using Olympus FV1000D confocal laser scanning microscope (Olympus, Tokyo, Japan).

Example 5—Repeat Length Analysis

Genomic DNA was extracted from HT1080-(CAG)850 clones and HD primary fibroblasts using the Gentra Puregene Cell Kit (Qiagen, Valencia, Calif.). The expanded (CTG)●(CAG) repeats were sized by small-pool PCR (sp- PCR) followed by Southern blot as described previously (Sathasivam et al., 1997, Hum. Genet., 99:692-5). For HT1080 models, small-pool PCR (spPCR) was performed with the input of 1.4-1.7 genome equivalents. The repeat size difference in the models is, at most, 3000 base-pairs, therefore, being strictly conservative, a bias toward amplifying the shorter allele can be possible, even under optimized PCR conditions described herein. For HD primary fibroblasts, sp-PCR & Southern blots were performed as described previously with slight modifications (Tome et al., 2013, PLoS Genet., 9:e1003280). Briefly, the PCR primers listed in Table 1 were used, and blots were hybridized with a DIG-labeled (CAG)7 locked nucleic acid probe (Nakamori et al. 2009, Neuromuscul. Disord., 19:759-62). At least 50 alleles were analyzed for each of the three experiments (more than 150 alleles for a total study). Repeat analyses are summarized in Table 2, compiled from complete small-pool-PCR datasets for each repetition of each experiment. For the histograms in FIGS. 4D, 4E, 10, 11, 5B, 5D, 5E, 14 and 15B, the Y-axis, "% of repeat population" was calculated by determining the proportion of >50 individual small-pool PCR reactions across the CAG repeat tract, that harbored a certain size of repeat product with a certain length. Cell clones were grown 30 or 40 days with or without NA (see, for example, Sathasivam et al., 1997, Hum. Genet., 99:692-5). Specifically, the histograms of repeat length distributions were from at least two different cell clones. Length distributions were determined as follows: Small-pool PCR followed by Southern blot for analysis of CAG/CTG repeat length. DNA from fibroblast clones was diluted to produce, on average, one amplifiable expanded repeat allele per PCR tube. The repeat tract was amplified by 24 cycles of PCR Amplified products were electrophoretically resolved, detected by Southern blot probing with a CAG repeat oligonucleotide, and repeat lengths determined relative to a DNA size marker. The scale on the left shows molecular weight markers (M) converted into repeat number for CAG-repeat fragments of equivalent size. To facilitate comparisons, a dashed line indicates the unchanged CAG size. The distribution of unstable alleles is shown by gray bars (left vertical axis). The frequency of stable alleles is shown by black bars (right vertical axis). Allele lengths are grouped in bins spanning 50 repeats along the X-axis. For the statistical analysis, $\chi2$-tests were performed to compare the frequencies of expanded, unchanged, and contracted alleles in each set of experiments as reported previously (Nakamori et al., 2011, Mol. Ther., 19:2222-7). The trinucleotide and dinucleotide tract lengths of the HTT, CASK, ATXN8, Mfd15, TDP, and murine Mapkap1, Fgd4, and tdp loci were PCR amplified through use of primers (listed in Table 1) and amplification conditions described elsewhere (see, for example, Kremer et al., 1995, Am. J. Hum. Genet., 57:343-50; Brook et al., 1992, Cell, 69:385; Koob et al., 1999, 21:379-84; Dietmaier et al., 1997, Cancer Res., 57:4749-56; Kabbarah et al., 2003, Mol. Carcinogen., 38:155-9). Repeat length variability was studied in non-expanded CAG alleles and TBP alleles by PCR (electrophoresed in high resolution gel) and Agilent BioAnalyzer, respectively. PCR products were separated on 6% polyacrylamide gels supplemented with EnhanceIT polymer (Elchrom Scientific, Switzerland), stained by GelRed (Biotium Inc., Hayward, Calif.), and scanned on a Typhoon fluorescence imager (GE Life Sciences, Piscataway, N.J.). Repeat analyses are summarized in Table 2, compiled from complete small-pool-PCR datasets for each repetition of each experiment.

TABLE 1

Primers

|  |  | Forward Primer | SEQ ID NO | Reverse Primer | SEQ ID NO |
|---|---|---|---|---|---|
| Small pool PCR | HT1080 cell model (for 850 CAG/CTG) | ACC CTA GAA CTG TCT TCG ACT CC | 1 | TTC CCG AGT AAG CAG GCA GAG | 2 |
|  | HTT (in HD cells) | GCC CAG AGC CCC ATT CAT TG | 3 | AGG AAG CTG AGG AGG CGG CGG | 4 |
| HD CAG Analysis | HTT (in R6/2 mice) | ATG AAG GCC TTC GAG TCC CTC AAG TCC TTC | 5 | CGG CGG TGG CGG CTG TTG | 6 |
| Non-expanded repeat loci | CASK | TTC AGT ACA TTG CTG CTG CTG | 7 | AAA AAG GTT CTG CTG ATG GAA | 8 |
|  | ATXN8 | TTT GAG AAA GGC TTG TGA GGA CTG AGA ATG | 9 | GGT CCT TCA TGT TAG AAA ACC TGG CT | 10 |
|  | HTT | CCT TCG AGT CCC TCA AGT CCT TC | 11 | GGC GGC GGT GGC GGC TGT TG | 12 |
|  | Mfd15 | GGA AGA ATC AAA TAG ACA AT | 13 | GCT GGC CAT ATA TAT ATT TAA ACC | 14 |
|  | Murine Mapkap1 | CTC TGA CCT ATC TCC AAT CCT C | 15 | TCT CCT TCT CCC TGA TTC AG | 16 |
|  | Murine Fgd4 | TAG GTC ATA AAT GAT CTG CTG C | 17 | ATG ATA ATC TCT CAA TGA CCC | 18 |
| HPRT1 | Exons 2 & 3 | TGG GAT TAC ACG TGT GAA CCA ACC | 19 | TGT GAC ACA GGC AGA CTG TGG ATC | 20 |

Primer sequences used in this study for PCR analyses presented in FIGS. 4, 5, 6, and FIGS. 10-17, 25A-H.

Example 6—mRNA Quantification

RNA was harvested from the HT1080-(CAG)850 cells at 72 hr after adding or not adding NA using the RNeasy Plus Micro Kit (Qiagen). Total RNA was primed with random hexamers and reverse transcribed with Superscript III (Life Technologies, Carlsbad, Calif.), followed by treatment with RNase H. Quantitative reverse transcription (RT)-PCR was performed using TaqMan Gene Expression assays or PrimeTime qPCR assays on an ABI PRISM 7900HT Sequence Detection System (Life Technologies) and the primer sequences shown in Table 1. The level of transgene-derived mRNA was normalized to 18S rRNA. The results were statistically analyzed using paired t-tests. Primer sequences for transgene mRNA in the CAG-repeat direction were 5'-AGA GAA TAG GAA CTT CGG AAT AGG-3' (SEQ ID NO: 21) and 5'-CCA TGT TCA TGC CTT CTT CTT T-3' (SEQ ID NO: 22). The probe sequence was 5'-ACA GCA CAA TAA CCA GCA CGT TGC-3' (SEQ ID NO: 23).

Example 7—NA-DNA Binding

Structures for band-shift assays were made as previously described (Pearson et al., 1997, Hum. Mol. Genet., 6:1117-23; Pearson et al., 2002, Nuc. Acids Res., 30:4534-47; Axford et al., 2013, PLos Genet., 9:e1003866), with minor changes. Plasmids containing human DM1 genomic (CTG)n●(CAG)n repeats (n=30 or 50) were linearized by HindIII digestion. Homoduplex slipped structure (S-DNA) of 50 repeats were formed by alkaline denaturation/renaturation, as described in Pearson et al. (1996, Biochem., 35:5041-53; 1998, Nuc. Acids Res., 26(3):816-23). Heteroduplex SI-DNA with long (CAG)20 or (CTG)20 slip-outs were prepared as previously described (Pearsons et al., 2002, Nuc. Acids Res., 30:4534-47; Axford et al., 2013, PLos Genet., 9:e1003866). Briefly, DNAs of (CAG)50 and (CTG)30 repeats, or DNAs of (CAG)30 and (CTG)50 repeats, were mixed in equimolar amount and then heteroduplexed by alkaline denaturation/renaturation. Repeat containing fragments were released by EcoRI digestion, electrophoretically resolved on a 4% polyacrylamide gel and gel purified. Purified fragments were radiolabeled with [$\alpha$-$^{32}$P]dNTPs on both strands by fill-in reaction. The radioactivity of each structure was determined using Cerenkov counting, and an equivalent radioactive concentration of each structure was incubated with increasing concentration of NA for 30 minutes at room temperature with 1× hypotonic buffer. Binding products were resolved by electrophoresis on a 4% (w/v) polyacrylamide gel in 1×TBE buffer at a constant 200 V for 2.5 hours. The affinity of each NA molecule/CAG-CAG was estimated as $1.8\times10^6$ M$^{-1}$ as Ka or $0.56\times10^{-6}$ M as Kd (Nakatani et al., 2005, Nat. Chem. Biol., 1:3943).

Example 8—Replication Assay

For in vitro replication, templates were designed as previously described (Panigrahi et al., 2002, J. Biol. Chem., 277:13926-34; Cleary et al., 2002, Nat. Genet., 31(1):37-46). Briefly, genomic clones containing EcoRI/HindIII (CTG)79●(CAG)79 fragments were subcloned into pBluescript KSII. The SV40-ori was cloned as a blunted XbaI fragment into either the HindIII or EcoRI sites of pBluescript KSII placing the SV40 origin of bidirectional replication 103 and 98 bp 5' and 3' of the CAG repeat, respectively. These templates containing repeats (pDM79EF and pDM79HF) and another substrate with SV40-ori and no-repeats (pKN16) were replicated in vitro by HeLa cell extract adding [$\alpha$-$^{32}$P]dCTP and T-Antigen, as described in detail in Panigrahi et al. (2002, J. Biol. Chem., 277:13926-34) and Cleary et al. (2002, Nat. Genet., 31(1):37-46). Replication reaction was performed without or with NA (7.5 µM and 15 µM). Radioactive replication products were purified, linearized with BamHI, and treated with DpnI (for details see FIG. 9). An equal amount of unreplicated pKN16 plasmid DNA was taken and treated with DpnI to show the complete digestion of unreplicated plasmid DNA. Equal quantities of reaction products were resolved by electrophoresis on a 15-cm 1% agarose gel. The gel was run for 16 h at 4 V/cm in TBE buffer, dried, and exposed to Kodak film.

Example 9—Repair Assay

To determine how the binding of NA to slipped DNA structures affects repair, a series of circular slipped heteroduplex substrates was made with an excess of repeats with a nick located either 5' or 3' of the slip-out (FIG. 3). As described in detail (Panigrahi et al., 2005, Nat. Struct. & Mol. Biol., 12:654-62; Panigrahi et al., 2010, PNAS USA, 107:12593-8), substrates were prepared by hybridizing single-stranded circular plasmids with their complementary linearized strand of differing repeat lengths, resulting in nicks located at the sites of linearization. Substrates were identical except for a single slip-out that varied only in the number of excess repeats, or in the location of the nick. In all substrates, the slip-out extruded at a unique point from a fully base-paired backbone of (CTG)n●(CAG)n, where n could equal 30, 47, 48, or 50 repeats. G-T mismatched substrate was prepared as described previously (Panigrahi et al., 2005, Nat. Struct. & Mol. Biol., 12:654-62; Panigrahi et al., 2010, PNAS USA, 107:12593-8). All these substrates were processed in Utro by HeLa extracts and then were assessed for repair. Repair products were analyzed by Southern blotting, probed for the repeat-containing fragment, and compared with starting material, which permitted quantitative assessment of repair efficiency at a molar level. Each repair assay was performed in three to five independent experiments.

Example 10—R-Loop Formation and Processing

Plasmids bearing an expanded (CAG)79●(CTG)79 repeat tract with convergent T3 and T7 RNA polymerase promoters have been previously described in detail (Panigrahi et al., 2002, J. Biol. Chem., 277:13926-34). Transcription reactions were performed as previously described (Reddy et al., 2014, Nuc. Acids Res., 42:10473-87). Briefly, 500 ng of template DNA in 1× transcription buffer (Roche) and 1× bovine serum albumin (NEB) were mixed for 1 h with 20 U of the appropriate RNA polymerase: T7, T3 or T7+T3 (Roche), with or without NA 120 µM. Samples were purified and then treated with either 1 g of RNase A (Roche) alone or with 1 g of RNase A (Roche) and 1 U of E. coli RNase H (Roche), at room temperature for 30 min, in the presence or in the absence of NA (120 µM). All in vitro transcription reaction products were analyzed on 1% agarose gels run in 1×TBE buffer at 80 V for 3 h. Gels were subsequently stained with ethidium bromide (0.5 mg/ml) to allow visualization of total nucleic acid under ultraviolet (UV) light.

R-loop templates prepared from in vitro transcription and RNase A treatments were incubated with NA and then processed by extracts of HeLa or SH-SY5Y neuroblastoma cells, where the latter were terminally differentiated by retinoic acid, as previously described (Panigrahi et al., 2005, Nat. Struct. & Mol. Biol., 12:654-62). These cell extracts are functional, processing slipped-strand DNAs formed by CAG/CTG repeats, and are capable of inducing replication-mediated CAG/CTG expansions and contractions. Nucleic acid material was subsequently extracted. Samples were further purified using QIAquick enzyme clean-up kits as per manufacturer's instructions prior to transforming into bacteria for Stability of Trinucleotide Repeats by analysis of Individual Products (STRIP) analysis. The STRIP assay has been previously described in detail (Panigrahi et al., 2002, J. Biol. Chem., 277:13926-34; Cleary et al., 2002, Nat. Genetics, 31:37-46). Briefly, products of human cell extract processing were transformed into E. coli XL1-MutS (Agilent).

Individual bacterial colonies, each representing one processed template, were picked and cultured for a limited growth period (maximum of 6 h, 4-6 generations). Miniprep DNA was analyzed for changes in repeat length by analysis of the repeat-containing fragment on 4% polyacrylamide gels. The magnitudes of repeat length changes were determined by electrophoretic sizing of the repeat-containing fragments on 4% polyacrylamide gels relative to the starting length material and a known set of size markers.

The non-transcribed DNA template (no transcription from T3 or T7 promoter) that was treated with human cell extract and subjected to STRIP served as the cell extract processing control to assess basal levels of length heterogeneity present in the starting material (instability during preparation in bacteria), as well as any instability that may be incurred by exposure of the fully-paired DNA repeat to the HeLa extract. As has been published, some level of length heterogeneity is expected for the DNA template due to its unstable starting length of 79 repeat units, resulting from processing of endogenous DNA damage (potentially including single strand breaks, oxidative damage, nucleotide mismatches, etc.) by human cell extract, repeat length heterogeneity present in the starting plasmid, as well as from bacterial culturing during the STRIP procedure. The tract length heterogeneity in this starting template serves as the background level of tract length instability above which any potential R-loop processing instability must rise. Only values that were significantly greater than background are reported. Instability analysis of products from R-loop processing by human cell extract. (A) Percentage of total unstable products following processing. Products were characterized as either stable (having 79 repeats) or unstable (having fewer than or greater than 79 repeats), based on electrophoretic migration and plotted. Data are derived from three independent in vitro transcription and human cell extract processing reactions with ~150 colonies (~50 colonies per replicate) representing 150 individual products of cell extract treatment analyzed for each R-loop configuration. Individual experiments were compared with each other within a triplicate using the $\chi2$ test to ensure there were no significant differences between experiments and then data were pooled for each experimental condition. As described (Reddy et al., 2014, Nuc. Acids Res., 42:10473-87), products of R-loop processing were compared to the DNA control processing products using the $\chi2$ test. Percentage of contractions and expansions from processing. Unstable products were further separated into contractions (fewer than 79 repeats) and expansions (greater than 79 repeats) and plotted. The distribution of contractions and expansions were compared between R-loop products and DNA control products using the $\chi2$ test. Distribution of unstable products of R-loop processing. Sizes were estimated for each unstable product of processing from electrophoretic migration position relative to known size markers as previously described (Panigrahi et al., 2002, J. Biol. Chem., 277:13926-34) and plotted.

Example 11—MutS Beta Binding Assay

MutS beta was purified from baculovirus-infected Sf9 cells expressing his-tagged hMSH2 and hMSH3 as previously described (Panigrahi et al., 2010, PNAS USA, 107: 12593-8). Binding reactions were performed at room temperature. Heteroduplex SI-DNA with long (CAG)20 was prepared and end-labelled as described above. Protein was incubated with DNA for 30 minutes in a buffer containing 10 mM HEPES-KOH pH 7.5, 110 mM KCl, 1 mM EDTA, and 1 mM DTT with or without ATP in the buffer as indicated. Reactions were loaded onto a 4% native polyacrylamide gel with non-denaturing loading dye (20 mM Tris-HCl pH 7.4, 4% glycerol, bromophenol blue). Gel was run in 1×TBE buffer for 2 h.

Example 12—FAN1 Nuclease Assay

FAN1 nuclease was purified from baculovirus-infected S9 cells using a double-affinity purification strategy as described previously for PALB2 (Buisson et al., 2010, Nat. Struct. Mol. Biol., 17(10):1247-54). Briefly, FAN1 was tagged at the N-terminus by a GST-tag and FLAG/His10-tagged at the C-terminus. Following GST-pull-down, the GST tag was removed by incubation with PreScission Protease and affinity purified on Talon beads (GE Healthcare).

1 pmol of 32P labelled, gel-purified, DNA structures containing a 5'-flap and either no repeats, or a (CAG)20 slip-outs in the flap or in the duplex region (see sequences in FIG. 22D-22F) were treated or non-treated with increasing concentration of NA for 10 min at RT, and incubated with 200 nM FAN1 for 30 min at 37° C. The reaction was performed in 1× nuclease buffer, as previously described (Liu et al., 2010, Science, 329:693-6), in 10 µl reaction volume. Nuclease reactions were stopped by adding 20 mM EDTA and purified by extraction with phenol/chloroform/isoamyl alcohol (25:24:1, v/v/v) following by ethanol precipitation. Reaction products were run on a 8% polyacrylamide gel at 200 V for 1 h. To identify FAN1 digestion sites, Maxam-Gilbert sequencing (G>A and T reactions) of the $^{32}$P labelled oligos was performed. Digestion fragments were separated on a 8% sequencing gel at 2500V and 82W for 75 min.

Example 13—Polymerase Extension Assay

Human DNA polymerase beta (Pol beta) was isolated from E. coli clones and purified by ion exchange and affinity chromatography (Chimerx, catalog #1077, Lot #2203007). Protein concentrations were determined using a Bradford assay.

Recombinant human polymerase delta (Pol delta) was prepared in insect cells using a recombinant baculovirus vector and purified by immunoaffinity column chromatography, as described (Zhou et al., 2012, PLoS ONE, 7(6): e39156). Protein concentrations determined using a Bradford assay.

Purification of recombinant RPA complexes were expressed in BL21(DE3) cells and purified as described in Binz et al (2006, Methods Enzymol., 409:11-38).

Pol delta extension assay was performed as previously described (Mason et al., 2010, Biochem., 49:5919-28), using an oligo containing (CAG)10 repeats. Oligo's sequence and primer condition were previously described (Hagihara et al., 2011, Chem. Bio. Chem., 12:1686-9). Briefly, 0.1 µM primer and 0.1 µM oligo were denatured at 95° C. for 3 min, annealed for 30 min at RT, and incubated with NA for 30 min. at RT. RPA and/or Pol delta were added and the reactions was started by adding 0.1 mM dNTPs in 10 µl reaction volume, and incubated at 37° C. for 15 min. The reaction was stopped by adding 20 mM EDTA and purified by extraction with phenol/chloroform/isoamyl alcohol (25:24:1, v/v/v) following by ethanol precipitation. Pellets were resuspended in formamide buffer, denatured at 95° C. for 10 min and run on a 6% sequencing gel at 2000 V and 90 W for 40 min.

Example 14—Stereotaxic Injections into R6/2 Mice

Mouse handling and experimental procedures were conducted in accordance with the Osaka University guidelines for the welfare of animals. A single drug application involved six separate stereotactic injections, three injections of drug or saline into three different striatal regions of either the left or right striatum, respectively (outlined in FIG. 24). Under sterile conditions, 6-week-old R6/2 mice were anesthetized with 50 mg/kg pentobarbital sodium, and stereotaxically injected with 5 µl of saline (right side) or 500 µM NA dissolved in saline (left side) into three different sites of the striatum. The mice received injections once or twice bi-weekly, or weekly for 4 consecutive weeks. Stereotaxic injections were delivered to three sites within the striatum with the following coordinates: (anterior-posterior (AP)=0.0 mm, medial-lateral (ML)=1.5 mm from bregma, dorsal-ventral (DV)=2.5 mm below the dural surface; AP=1.0 mm, ML=1.5 mm, DV=2.5 mm; and AP=0.5 mm, ML=1.5 mm, DV=2.5 mm), using a 10-µl Hamilton microsyringe at a rate of 0.5 µL/min. Refer to FIG. 24 outlining dosing regimen. Each mouse had an internal control, as both sides of the brain were stereotaxically injected with either saline, in the right striatum, and NA, in the left striatum. The control of our NA treatment is therefore the contralateral side of the striatum of each mouse. Both right and left striatum were assessed for repeat length at the HD CAG transgene and at endogenous, long CAG tracts. For the mice treated four times, DNAs from the tail prior to and following NA administration, as well as left and right frontal cortex and left and right cerebellum were harvested.

Example 15—Genescan Analysis

At 4 weeks after the first injection, DNA was isolated from mouse brain tissue as previously described (Nakamori et al. 2009, Neuromuscul. Disord., 19:759-62). PCR was performed as described previously (Tome et al., 2013, PLoS Genet., 9:e1003280), and PCR products were sized on an ABI310 Gene Analyser using GENESCAN 3.1 software (Life Technologies).

Example 16—Instability Index Calculation

The procedure for instability index calculation was done as previously described (Lee et al., 2010, BMC Syst. Biol., 4:29) and is illustrated and outlined in FIG. 27A.

Example 17—HPRT1 Sequence Analysis by SMRT-CCS Sequencing

DNAs were extracted from three independent NA treatments of the HD primary fibroblast cell line GM09197 and from three independent untreated control cells. HPRT1 exons 2 and 3 were amplified using the high fidelity Platinum Taq DNA Polymerase (Invitrogen, Cat #11304) and the primers shown in Table 1. Amplification products were analyzed using single molecule, real-time (SMRT) sequencing on the PacBio RSII instrument (see FIG. 13A).

Figure 13A:
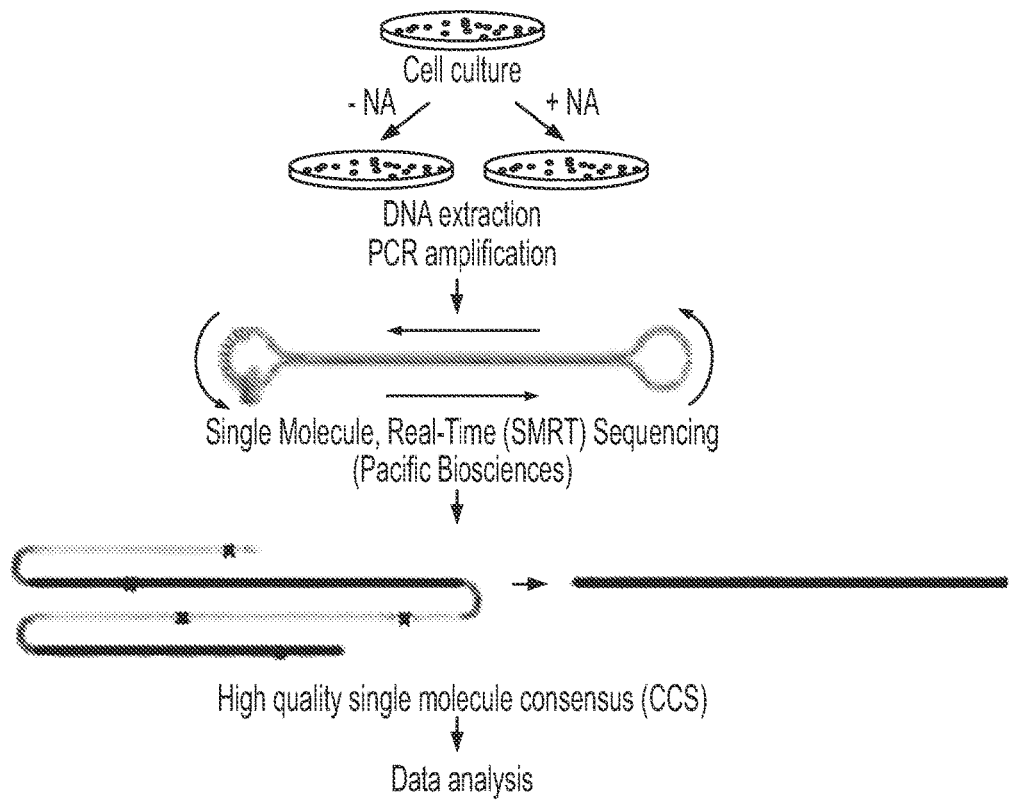
FIG. 13 shows data that demonstrates that NA is not a general mutagen. Towards assessing whether NA-treatment acted as a general mutagen to sequences other than CAG slip-outs, the high read accuracy and depth of single molecule, real time, circular consensus sequencing (SMRT-CCS) was harnessed. Single-molecule sequencing was done on the HPRT1 gene—widely used as a surrogate indicator of the global effect of induced genetic variation. Single-molecule sequencing can detect mutations at frequencies below 0.5% with no false positives. Panel A of FIG. 13 is a schematic of HPRT1 sequencing for mutation detection. Briefly, cells were grown under identical conditions differing only by the addition of NA (50 µM) or saline, DNAs were isolated, HPRT1 exons 2 and 3 PCR amplified and sequenced. Panel B of FIG. 13 are graphs showing the comparison of sequence variations between NA-treated and saline-treated samples. We chose to compare the single-molecule sequence reads of individual X chromosome-linked HPRT1 alleles (exons 2 and 3, 2,897 nucleotides) from the male HD patient-derived cells that had been NA- or saline-treated. In this manner, each read would represent a single cell. Graphs show the distribution of sequence variants by relative mutation rate between three experimental replicates of NA-treated and saline-treated cells sequenced with PacBio single-molecule long reads. Comparison of up to 2,402 individual HPRT1 alleles did not reveal any sequence differences. While there was minimal sequence variation, this did not differ significantly between NA- and saline-treated cells (p=0.1083, two-sample Kolmogorov-Smirnov test). Panel C shows that SMRT long read sequencing was ideal for this application because it can sequence the whole length of the amplicon in a single contiguous read, using multiple passes through the read to generate high quality consensus sequence. Thus, the absence of sequence differences between the separate replicates is evidence that NA does not act as a general mutagen.
Figure 13B:
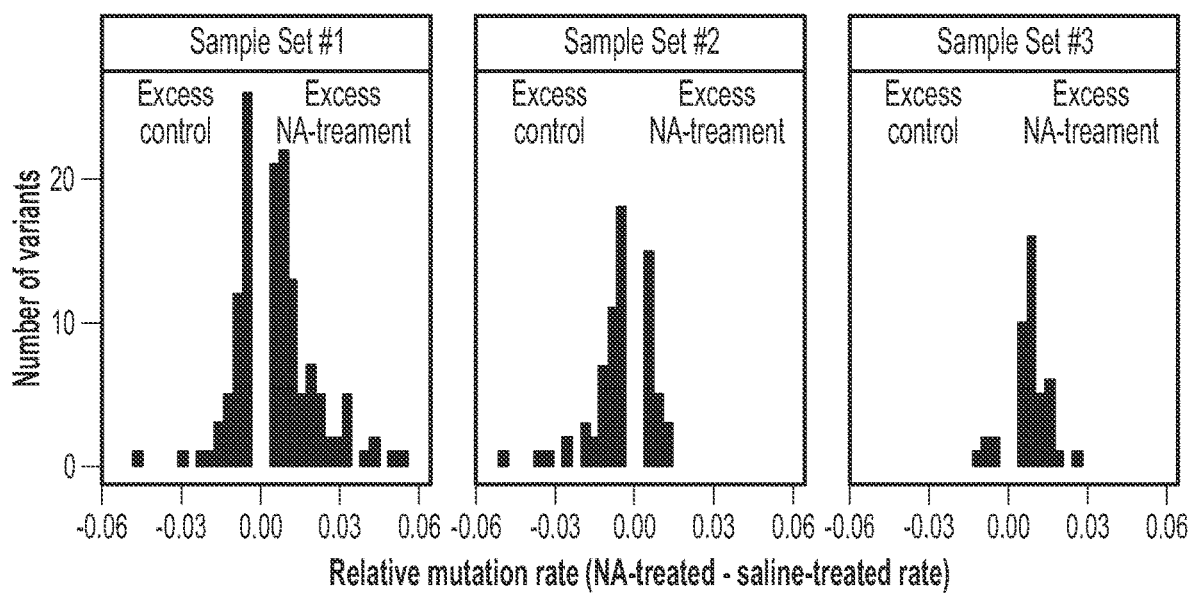
Figure 14:
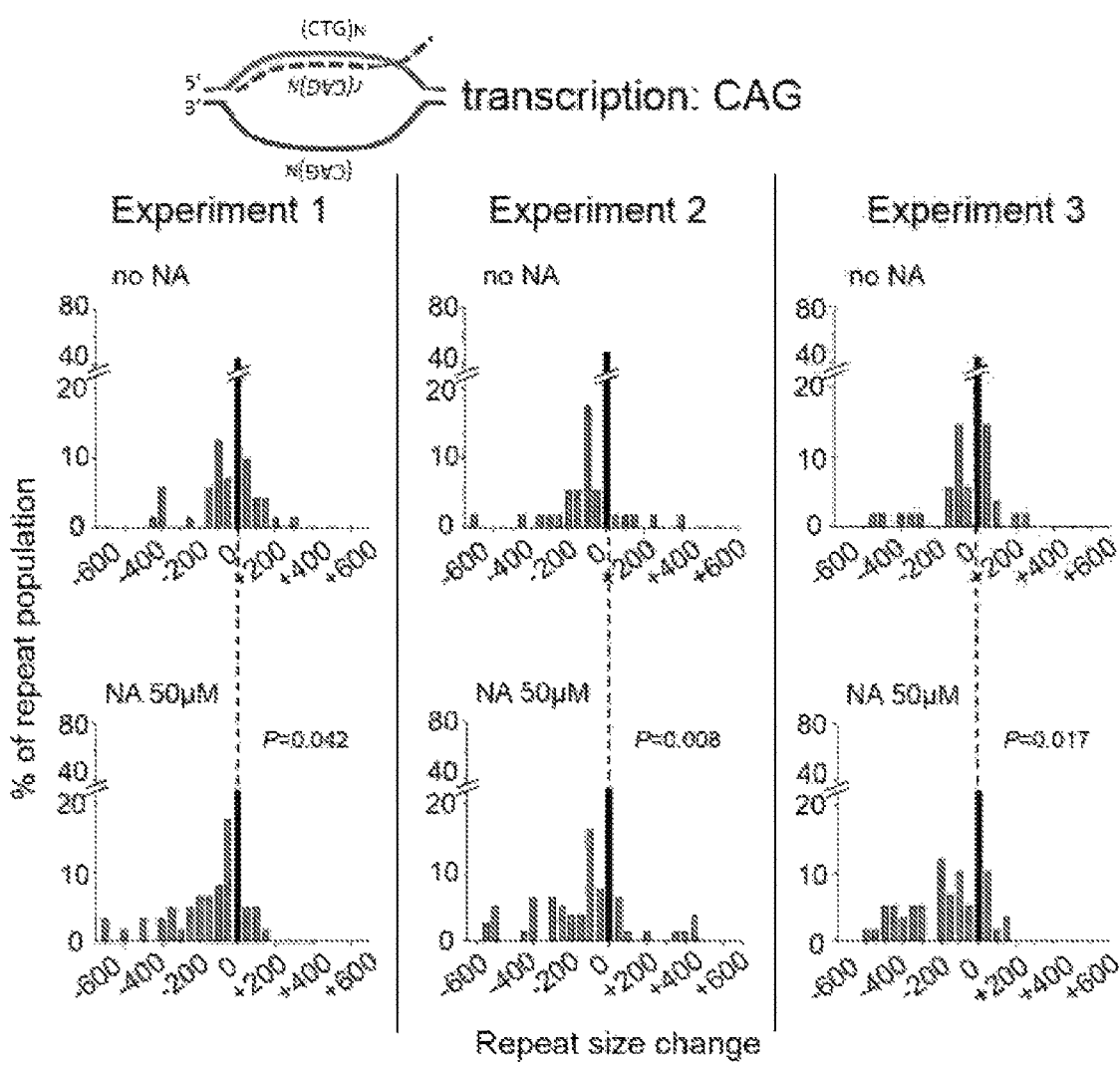
FIG. 14 shows independent analyses of the effects of NA on repeat instability in HT1080-(CAG)850, producing an rCAG transcript. Histograms showing repeat length distributions in HT1080-(CAG)850 cells. Repeat lengths were analyzed by small-pool PCR in both untreated and NA-treated cells, in three independent experiments. The frequency distribution of unstable alleles is shown by gray bars. The frequency of stable alleles is shown by black bars. A reduction of the CAG length tracts is evident in the NA-treated cells in each experiment. To facilitate comparisons, a dashed line indicates the starting unchanged CAG size. P-values were calculated by chi-square test.
Figure 15:
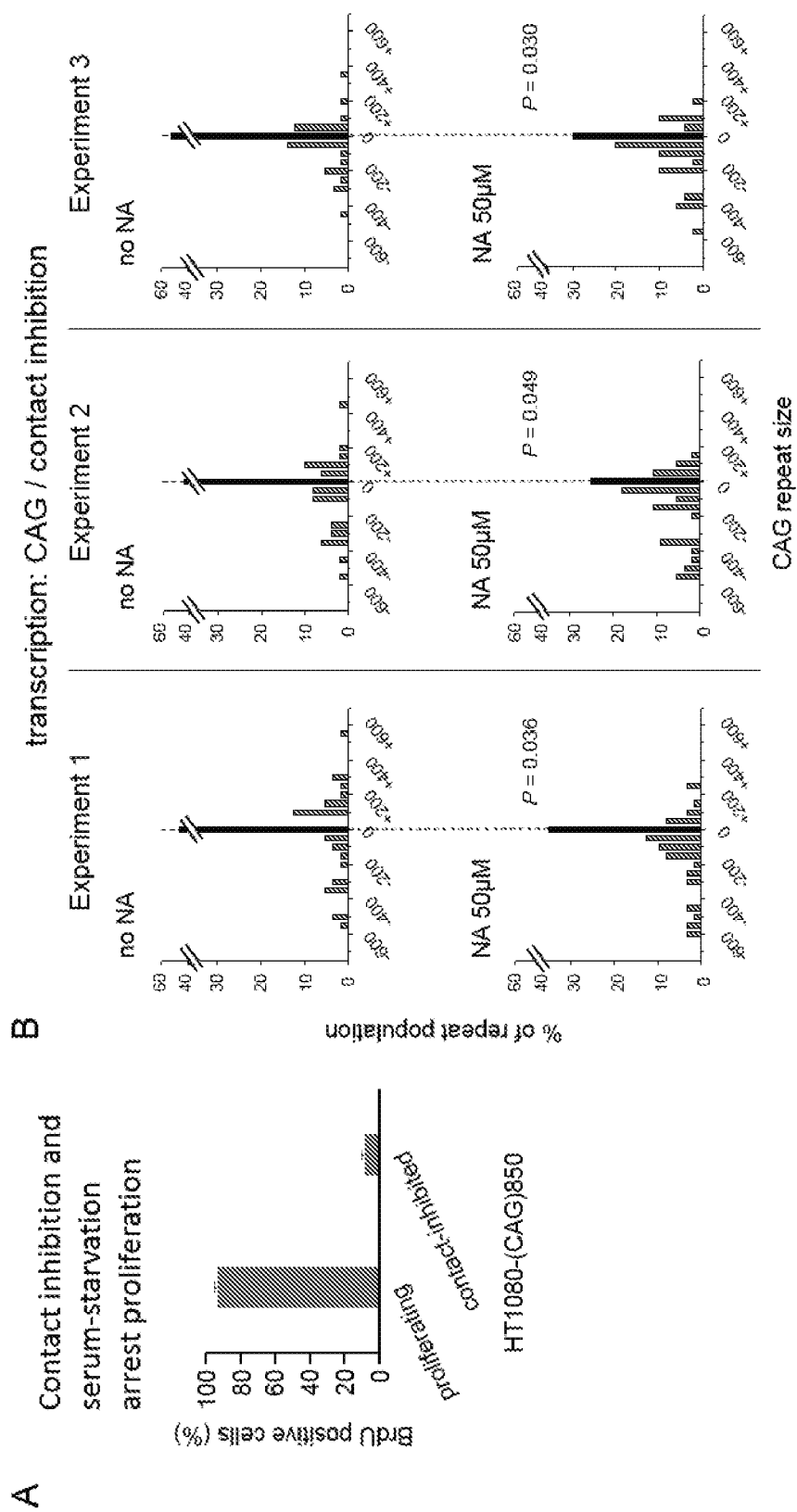
FIG. 15 shows the effect of NA in (CAG)850 cells is independent of proliferation. The effect of NA was tested in non-proliferating cells maintained in contact inhibition for the same interval as in FIG. 4. Panel A of FIG. 15 shows the contact inhibition and serum-starvation arrest proliferation, as measured by the proportion of BrdU positive cells after 24 h in BrdU-containing media. Panel B of FIG. 15 shows histograms showing repeat length distributions in HT1080-(CAG)850 cells under contact inhibition. Repeat lengths were analyzed by small-pool PCR in both untreated and NA-treated cells, in three independent experiments. The frequency distribution of unstable alleles is shown by gray bars. The frequency of stable alleles is shown by black bars. The effect of NA was independent of cell proliferation. NA induced a shift toward contraction of expanded repeats in the contact-inhibited cells (P<0.05). To facilitate comparisons, a dashed line indicates the unchanged CAG size. P-values ware calculated by chi-square test.

Specifically, a ~2.8 kb PCR product spanning exons two and three of HPRT1 was sequenced for three replicates of male HD patient-derived cells in both NA- and saline-treated colonies on a Pacific Biosciences (PacBio) RSII with P6-C4v2 chemistry, 360 minute movies, and one SMRT cell per replicate/treatment combination. Individual molecules from the original cell colony were represented by single long reads from the corresponding SMRT cell. PacBio's SMRTbell construct allows a single molecule to be sequenced one or more times in a single long read based on the number of "passes" the sequencing polymerase makes around the SMRTbell insert. An average of 99,023 distinct reads were sequenced per SMRT cell. The resulting long reads contained an average of ~7 passes through the insert sequence. The average median insert length per SMRT cell was 2,873 bp. Using PacBio's "reads of insert" pipeline (SMRT Analysis 2.3.0), high-quality consensus sequences were created for each long read that contained more than 18 copies of the original molecule and eliminated consensus sequences with either an incomplete PCR molecule (<2.5 kbp) or with incorrectly detected PacBio adapters that resulted in overly long consensus sequences (>3 kbp) (FIG. 13C). Based on these filters, an average of 1,343 consensus sequences per replicate/treatment pair were produced with a range of up to 2,402 sequences. Consensus sequences were aligned to the corresponding region of the human reference (GRCh38, chrX:134,473,062-134,475,958) with BLASR (SMRT Analysis 2.3.0; parameters: -affineAlign-affineOpen 8-affineExtend 0-bestn 1-maxMatch 30-sdpTupleSize 13-m 5) and all single base pair differences were identified between sequences and the reference (mismatches, insertions, and deletions) for sequences with full-length alignments (2.5-3 kbp). The average alignment identity of the consensus sequences was 99.698%+/−0.3321% SD with a range of 94.7679% to 100%. To estimate the mutation rate for each replicate/treatment combination, the number of times a specific variant occurred was calculated between high-quality PacBio consensus reads at a specific position in the human reference (GRCh38) divided by the total number of high-quality reads aligned across each position. For each replicate, the relative mutation rate was calculated between NA- and saline-treated cells as the mutation rate for NA-treated cells minus the rate for saline-treated cells and identified excess mutation rates based on an absolute relative rate >0.5%. Of the 15,277 variants identified across all three replicates, there were extreme mutation rates in 149 (1.0%) NA-treated sequences and 101 (0.7%) saline-treated sequences. Across the 2,897 positions assessed in the human reference, extreme relative mutation rates were identified at 113 distinct sites in treated sequences (3.9%) and 84 sites in control sequences (2.9%). Mutation rates were not significantly different between NA- and saline-sequences for variants with extreme relative mutation rates (p=0.1083, two-sample Kolmogorov-Smirnov test) (FIG. 13B).

Example 18—Results

A CAG-specific DNA binding compound, Naphthyridine-Azaquinolone (NA) (Nakatani et al., 2005, Nat. Chem. Biol., 1:39-43; Hagihara et al., 2006, Nuc. Acids Symp. Ser. (Oxf.), 50:147-8; Hagihara et al., 2011, Chembiochem., 12:1686-9) previously was designed. Detailed characterization revealed NA bound a distorted intra-strand CAG hairpin, where the naphthyridine and azaquinolone moieties in NA exhibit complementary hydrogen bonding to guanine and adenine, respectively, causing two cytosine bases to flip-out from the CAG hairpin (FIGS. 2A and 2B). NA bound with high affinity and increased the melting temperature of (CAG)10 hairpins by >30° C. (Hagihara et al., 2011, Chembiochem., 12:1686-9). NA also bound with a preference for longer CAG hairpins, where the greatest binding was to (CAG)30, followed by binding for (CAG)20, and (CAG)10 (Nakatani et al., 2005, Nat. Chem. Biol., 1:39-43). This remarkable selectivity of NA for longer CAG hairpin structures coupled with the presence of slipped-DNAs at a mutant repeat locus (Axford et al., 2013, PLos Genet., 9:e1003866) may permit targeting of the expanded allele.

Figure 2C:
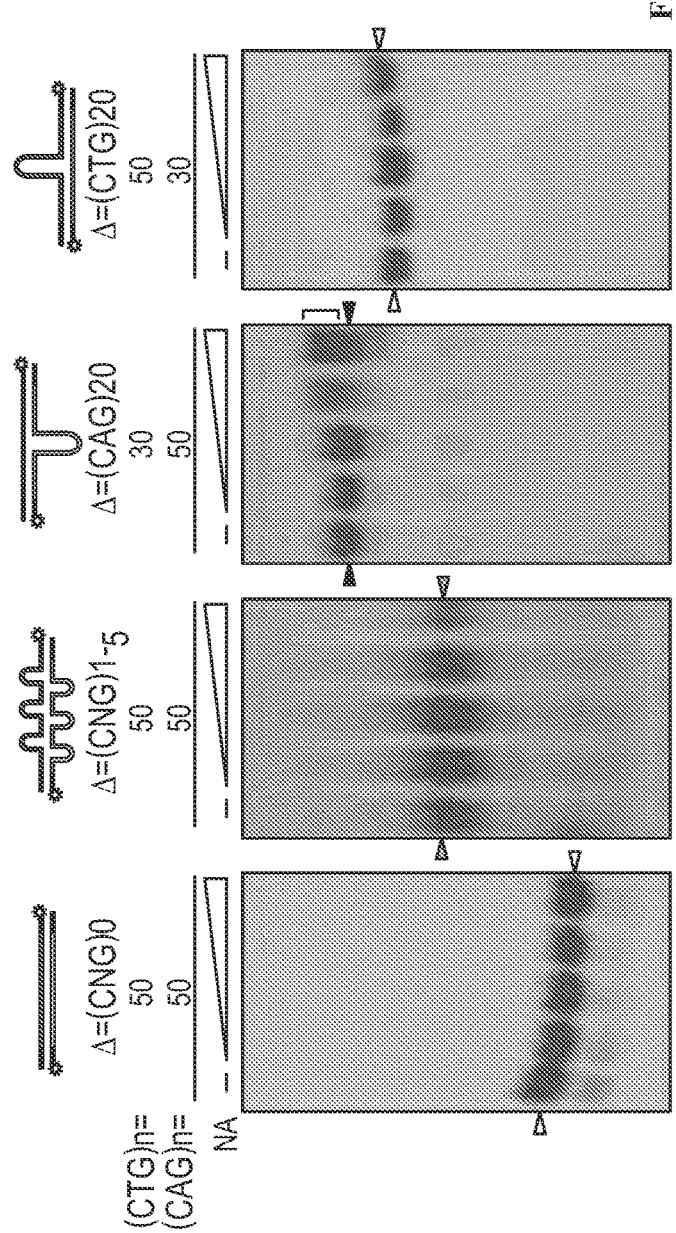
Figure 2D:
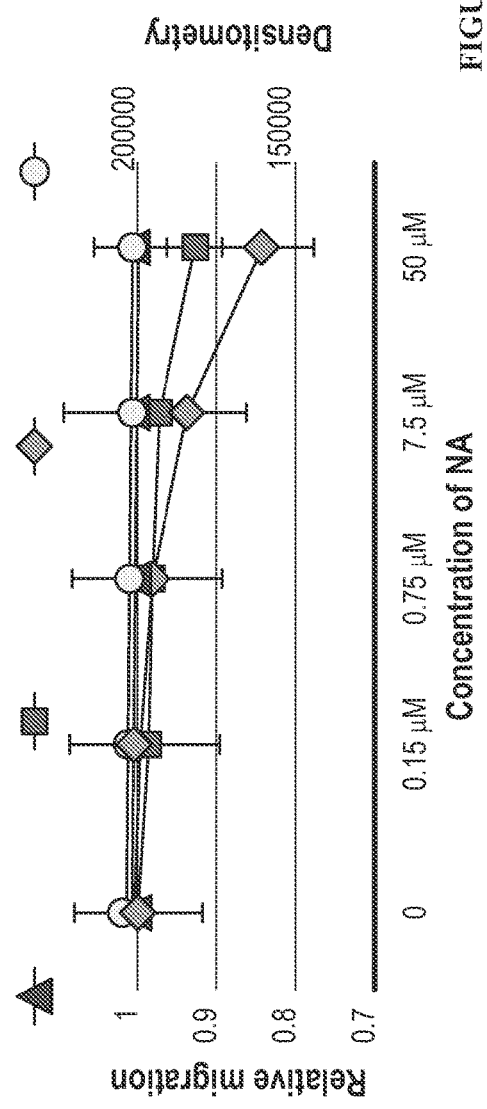
Figure 2E:
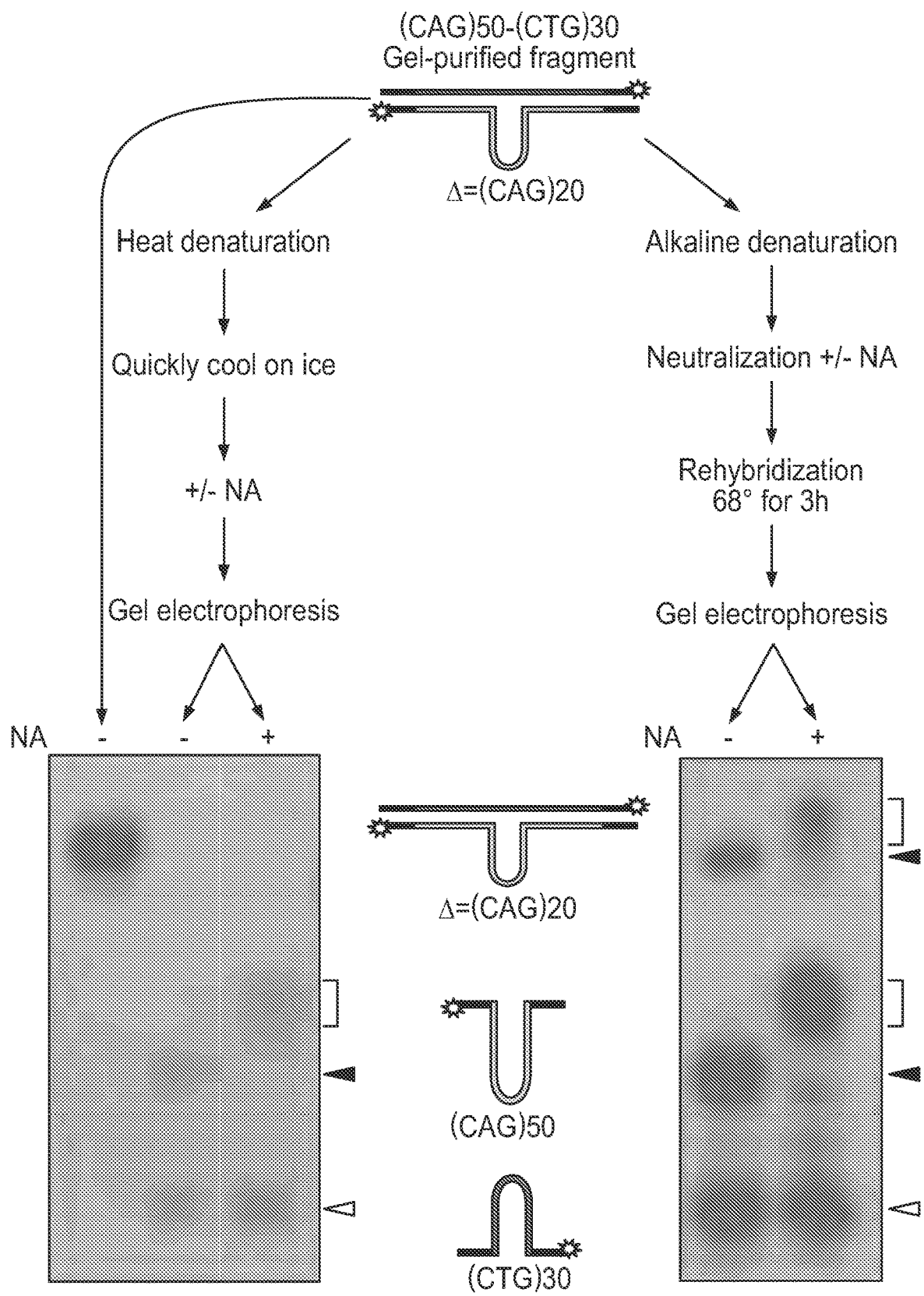
Figure 7:
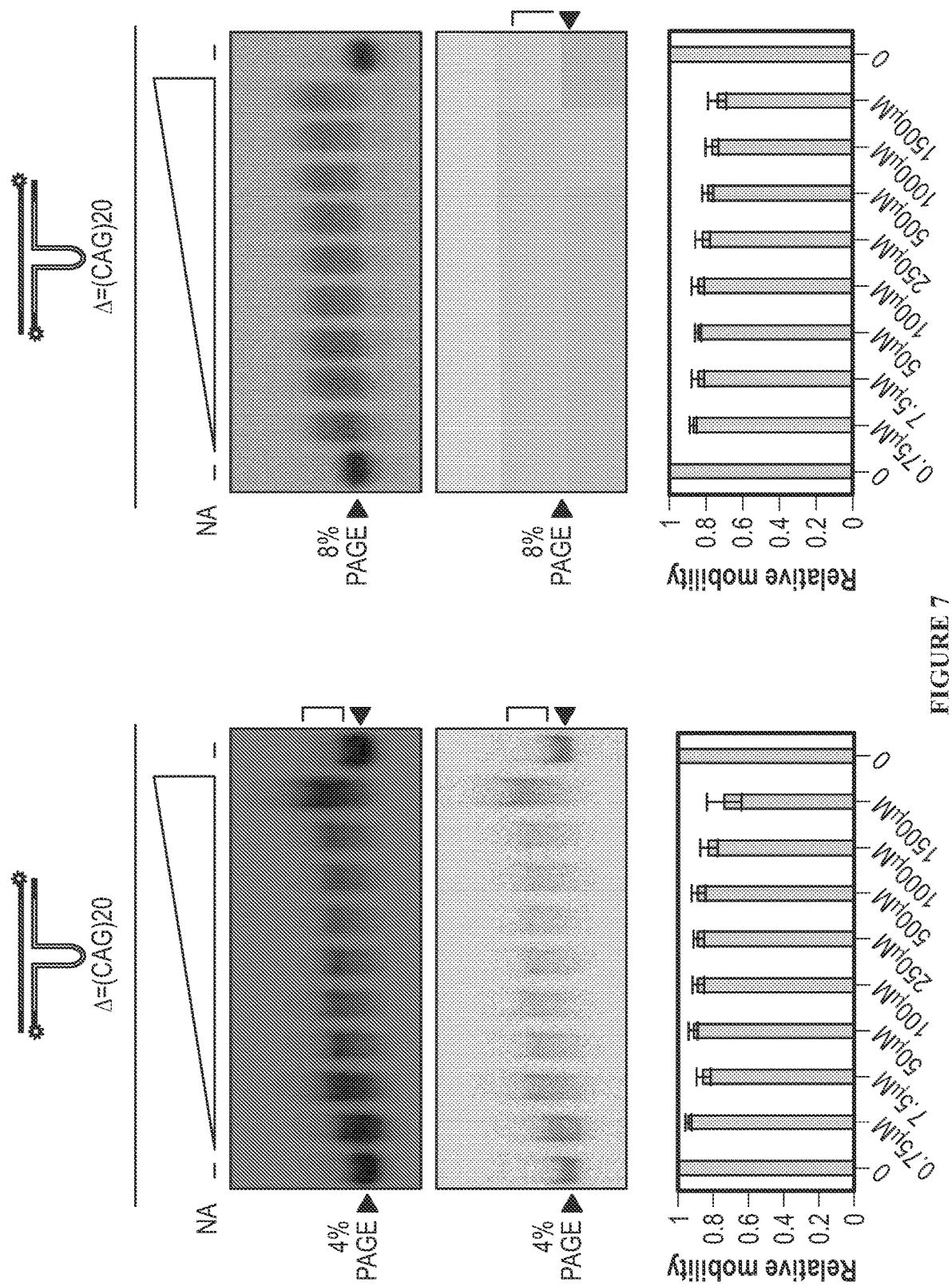
FIG. 7 shows high-resolution polyacrylamide gel electrophoretic separation of NA-bound CAG slip-outs. 1 pmol of gel-purified DNA heteroduplex with a long (CAG)20 slip-out, from (CAG)50●(CTG)30, $^{32}$P-labeled on both strands, was mixed with increasing concentrations of NA (0.75 µM, 7.5 µM, 50 µM, 100 µM, 250 µM, 500 µM, 1000 µM and 1500 M) and resolved on 4% polyacrylamide gels (left panels) or 8% polyacrylamide gels (right panels). NA-DNA complexes are shown by brackets, free DNA is indicated by arrowheads. The relative mobility shift (Rm) was measured (graph panel) as the ratio of the migration distance of each NA-DNA complex to the migration distance of the free DNA. The migration distance was measured with a ruler from the well to a consistent centre point of each band. Histograms indicate the mean of three independent experiments and the corresponding standard deviation. NA-binding to (CAG)50●(CTG)30 caused a band-broadening, previously observed for other DNA-binding ligands (Nielsen et al., 1988, Biochem., 27:67-73; Barcelo et al., 1991, Biochem., 30:4863-73; Carlsson et al., 1995, Nuc. Acids Res., 23:2413-20; Fox et al., 1988, Nuc. Acids Res., 16:2489-507).
Figure 8:
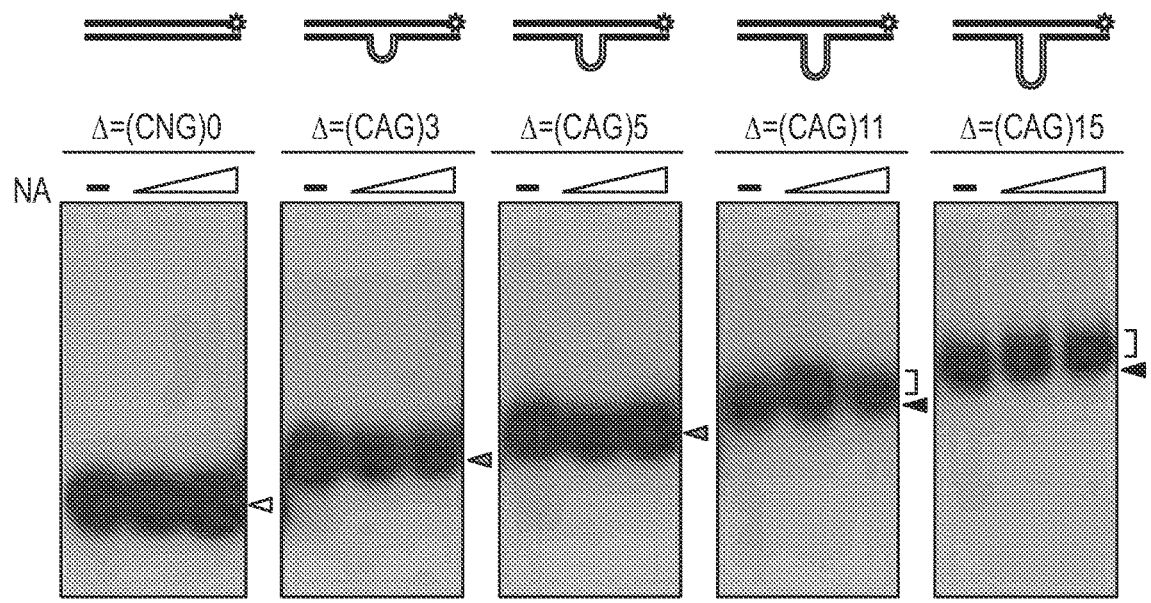
FIG. 8 shows binding of NA to DNA substrates with either no repeats (left panel) or (CAG)n repeats in one strand, $^{32}$P-labeled on the common strand. Slip-outs of 3, 5, 11 or 15 CAG repeats extruded as a single slip-out from a fully base-paired backbone (see top panel, DNAs sequence and structure). One pmol of each substrate was mixed with increasing concentrations of NA (15 µM and 50 µM) and resolved on 4% polyacrylamide gels. All lanes are from the same gel, and they were separated for clarity. NA-DNA complexes are shown by brackets, free DNA is indicated by arrowheads. For the linear substrate, there is no NA binding (white arrowheads); at the higher concentration of NA, a small decrease of the short slip-outs DNAs (3 and 5 repeats) is observed (grey arrowheads), but it is not possible to define a clear shifted band; band-shift is evident for the (CAG)$_{11}$ and (CAG)$_{15}$ slip-out DNAs (black arrowheads). The relative mobility shift was measured (graph panel) as the ratio of the migration distance of each NA-DNA complex to the migration distance of the free DNA. The migration distance was measured from the well to a consistent centre point of each band. Histograms indicate the mean of three independent experiments and the corresponding standard deviation. P-values were calculated by Student's t test.
Figure 8:
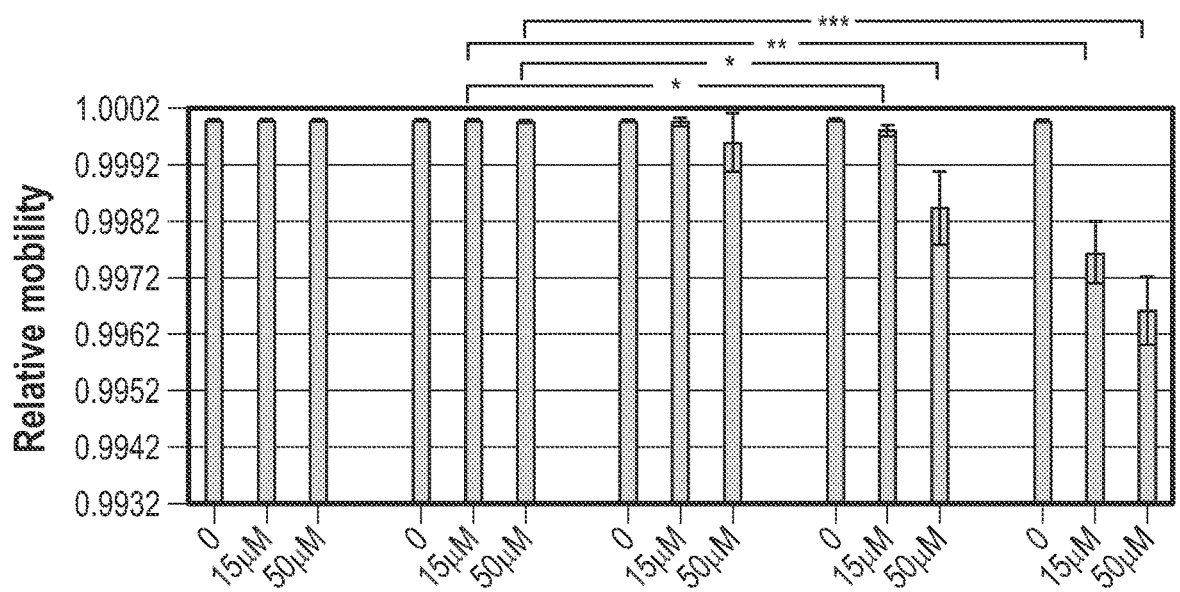

To determine if NA can bind to disease-relevant (CAG)●(CTG) duplexes with and without slip-outs, band-shift analysis was performed using slipped-DNAs, which are models of mutagenic intermediates of repeat instability (Pearson et al., 2002, Nuc. Acids Res., 30:4534-47). Detailed biophysical characterization of these in vitro structures show that they reflect the slipped-DNAs recently identified at the mutant DM1 locus in DM1 patient tissues (Axford et al., 2013, PLos Genet., 9:e1003866). NA did not bind to fully-duplexed DNA fragments containing (CAG)50●(CTG)50 repeats, and high concentrations of NA did not induce structural alterations of the fully-duplexed repeat (FIG. 2C-2D). The same (CAG)50●(CTG)50 molecules could be induced to harbor clustered short slip-outs, called S-DNAs, which comprise a heterogeneous mixture of molecules, each containing 2-62 short slip-outs of mostly 1 to 5 repeat units each, extruding at various locations from both strands along the repeat tract (Pearson et al., 1998, Nuc. Acids Res., 26:816-23; Panigrahi et al., 2010, PNAS USA, 107:12593-9). S-DNAs can bind NA to a limited degree, but their short slip-outs and electrophoretic heterogeneity may not permit detection of a single-shifted species. Slipped-heteroduplexes with an excess of twenty CAG repeats in the slip-out of (CAG)50●(CTG)30 were extensively bound by NA (FIG. 2C-2D, see also FIG. 7). NA-binding caused a band-broadening, previously observed for other DNA-binding ligands (Neilsen et al., 1988, Biochem., 27:67-73; Carlsson et al., 1995, Nuc. Acids Res., 23:2413-20; Barcelo et al., 1991, Biochem., 30:4863-73; Fox et al., 1988, Nuc. Acids Res., 16:2489-507; Fox & Woolley, 1990, Biochem. Pharmacol., 39:941-8). The progressively slower migration of the slipped-DNA in the presence of NA is consistent with NA binding to additional (CAG)●(CAG) pairs in the hairpin (FIG. 7; Nakatani et al., 2005, Nat. Chem. Biol., 1:39-43). In contrast, heteroduplexes with long slip-outs of CTG repeats, (CAG)30●(CTG)50, were not bound by NA (FIG. 2C-2D, the multiple panels of FIG. 2C were all derived from a single gel, and were separated for clarity). Thus, NA bound CAG but not CTG slip-outs. Binding was quantitatively specific for the CAG slipped-DNA structures (FIG. 2D). Denaturation of purified slipped (CAG)50●(CTG)30 to isolated (CAG)50 and (CTG)30 single-strands (without renaturation) in the presence of NA also showed NA binding specifically to the single-stranded (CAG)50 strand (FIG. 2E, left panel). Renaturation of individual (CAG)50 and (CTG)30 single-strands in the presence of NA revealed that NA did not block the ability of complementary strand hybridization, but did bind specifically to the slipped-out CAG strand and not the CTG strand (FIG. 2E, right panel). The degree of electrophoretic shift of the isolated single-stranded (CAG)50 tract is greater than for the heteroduplex (CAG)50●(CTG)30, which has a slip-out of only 20 excess CAG repeats, whereas, once rendered single-stranded, the full 50 CAG repeats is forced into a long hairpin of all 50 repeats (FIG. 2, compare panels E)—which can bind more NA molecules. The CTG hairpin strand is not bound by NA (FIG. 2C-2E). Binding was significantly better for longer than shorter CAG slip-outs (FIG. 8). Based upon these results and the established binding mode of NA, a ratio of 2 NA molecules to 1 CAG-CAG was previously estimated, wherein a slip-out of (CAG)20 would bind 20 NA molecules. Together, these findings support the structure-specificity of NA for long CAG repeat slip-outs of disease-relevant tract lengths, but do not support the contention that NA will induce slip-out extrusion from an expanded fully duplexed molecule.

Figures 3D, 3E:
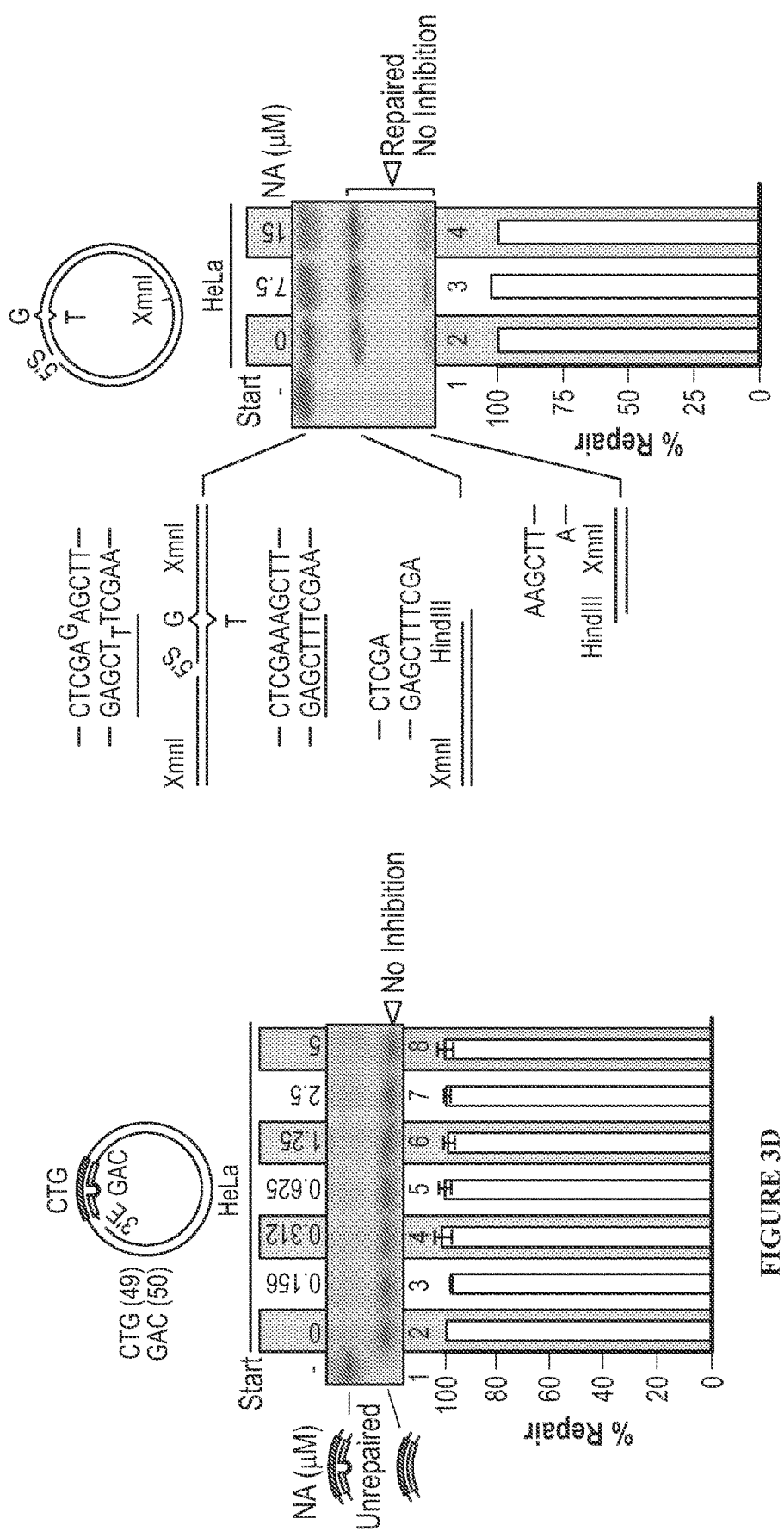
FIG. 3 shows that NA specifically inhibited repair of long CAG slip-outs by human cell extracts (HeLa cells). Panel A of FIG. 4 is a schematic of the in vitro repair assay. Starting DNAs and repair products released the repeat-containing fragment, which is resolved on PAGE and assessed on a molar level by Southern blotting and densitometry. Repair of different DNA substrates containing a long (CAG)20 slip-out (Panel B of FIG. 3) long (CTG)20 slip-out (Panel C of FIG. 3), a single CAG slip-out (Panel D of FIG. 3) or a single G-T mismatch (Panel E of FIG. 3), in the absence or in the presence of NA. Slipped-DNA substrates were prepared from hybrids of (CAG)50●(CTG)30, (CAG)30●(CTG)50 or of (CAG)50●(CTG)49. Repair of the G-T mismatch reconstitutes a HindIII restriction site, as shown schematically. Graphs show percentage repair efficiencies to repaired product relative to all repeat-containing fragments in the lane, values are normalized to the NA-free efficiency. Values represent the mean of three to five independent experiments±standard deviation. NA inclusion inhibits the repair of the long (CAG)20 slip-out (Panel B of FIG. 3), but doesn't affect the repair efficiency of all the other substrates (Panels C, D, and E of FIG. 3).
Figure 4A:
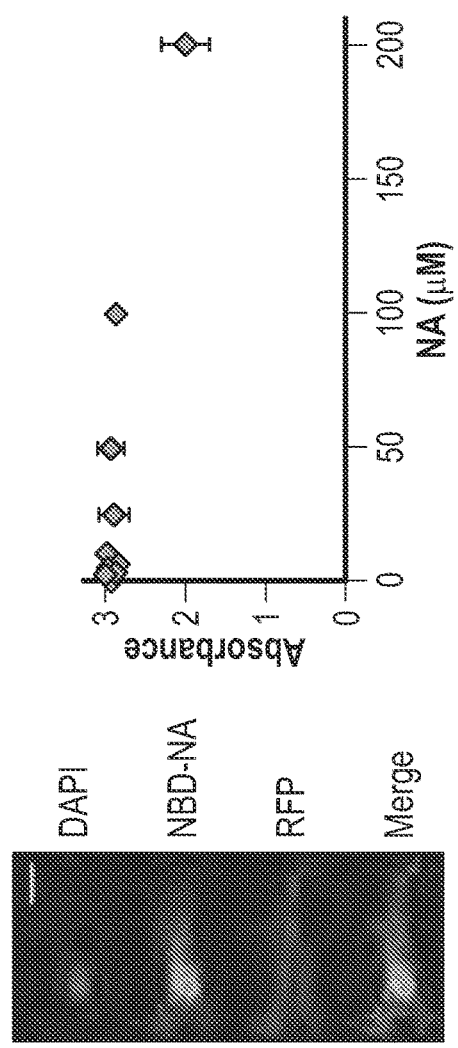
FIG. 4 are results of experiments showing NA cellular distribution, non-toxicity, and effects on repeat instability in HD patient cells. Panel A of FIG. 4 shows the cellular distribution of NA in HT1080 cell model with (CAG)850. NBD-labeled NA (green) was distributed throughout the nuclei and cytoplasm. Nuclei and cell membranes were stained with DAPI (blue) and Cell Light Plasma Membrane-RFP (red), respectively. Scale bar represents 20 µm. Panel B of FIG. 4 shows the cell toxicity of HT1080-(CAG)850 cells treated with NA for 72 hr. The cell viability was estimated with WST-1 assays. Values represent the means of three independent measures±SD. Panel C of FIG. 4 shows the growth curves of HT108-(CAG)850 cells treated with or without 50 µM NA. Error bars indicate the SD of triplicate experiments. Panels D & E of FIG. 4 show that repeat instability was analyzed by small-pool-PCR across the HD repeat tract (see Table 2). Histograms show repeat-length distributions in human HD primary fibroblasts GM09197 with (CAG)180 or GM02191 with (CAG)43, after 40 days growth with or without NA. The frequency distribution of repeat alleles is indicated as gray bars. The dashed line indicates the peak CAG size. Allele lengths are grouped in bins spanning 10 repeats. More than 230 alleles were sized per group. Percentage of repeat population was calculated by dividing the number of alleles grouped in bins spanning 10 repeats by the number of total alleles. Shown is a summary of 3 independent experiments (see FIGS. 10 & 11). Panels G & H of FIG. 4 show the average repeat size in HD fibroblasts after 40 days incubation with or without NA. *$P<0.001$, Student's t test. Panel H shows repeat-tract lengths of the CASK, HTT (normal allele), and Mfd15 loci in HD fibroblasts (after 40 days incubation with or without NA) (see also FIGS. 12A & 12C). Length variation was not observed at any of these non-expanded.
Figure 4B:
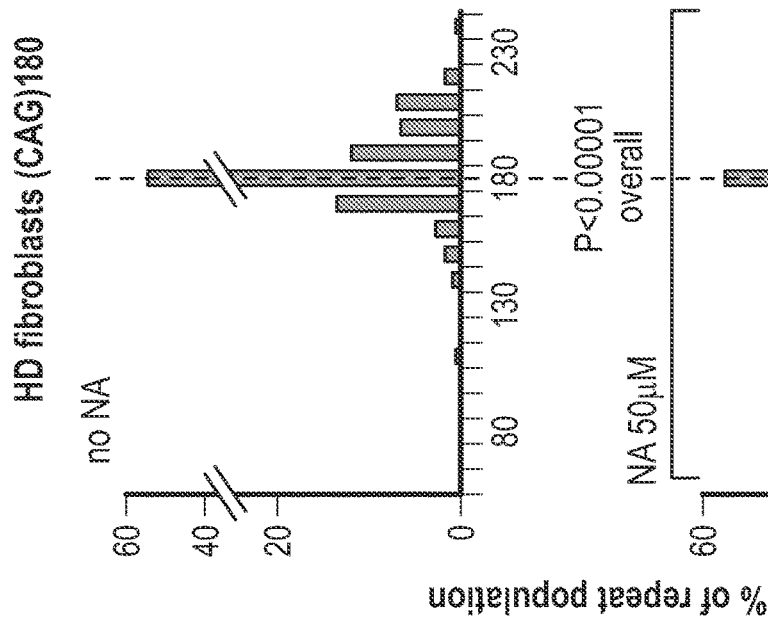
Figure 4D:
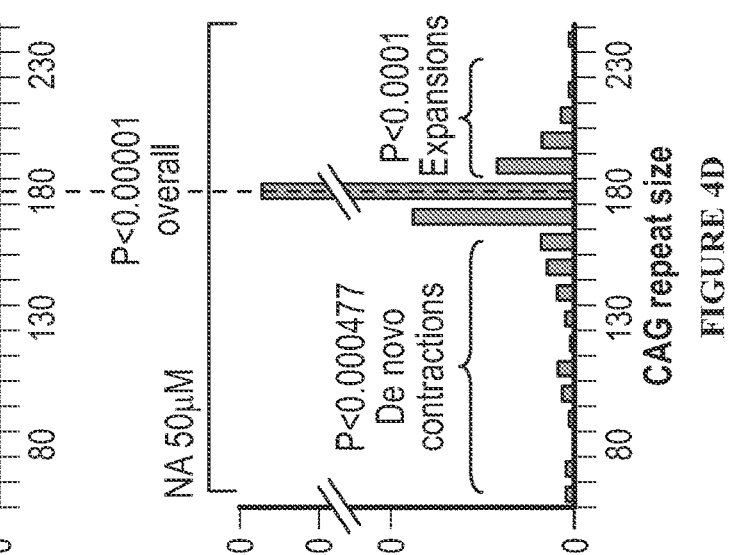
Figure 4C:
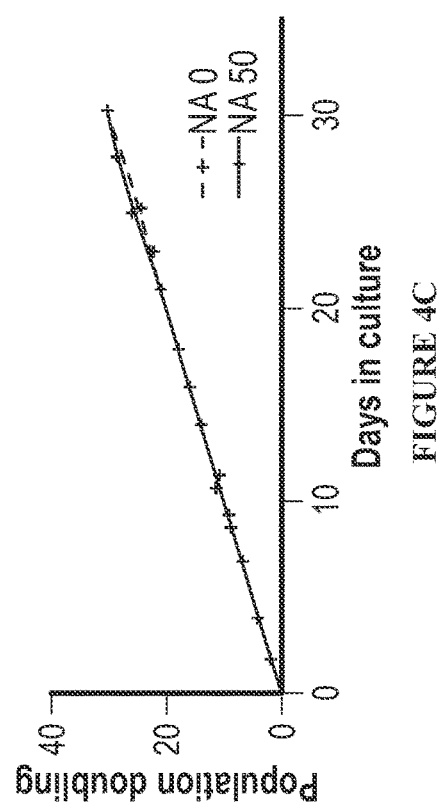

NA blocks processing of slipped-DNAs, suggesting it may modify repeat instability. NA specifically inhibits repair of slipped-DNAs with long (CAG)20 slip-outs, but not (CTG)20 slip-outs (FIG. 3A-3C), consistent with its designed specificity for CAG hairpins (FIG. 2). That NA blocked the repair of a (CAG)20 slip-out, is consistent with the inability of human and other DNA polymerases to extend primers along NA-bound (CAG)10-(CAG)20 templates. The repair of long (CAG)20 slip-outs is independent of mismatch repair (MMR), indicating that the effect of NA does not require an involvement of MMR. In contrast, single repeat slip-outs, too small to bind NA, require the mismatch repair MutS beta (MSH2-MSH3) complex. The effects of NA upon repair of a single extra CAG repeat slip-out, too small to be bound by NA, were assessed. Repair of a single repeat CAG or CTG slip-out was unaffected by NA, indicating that MutS beta function in this process was unaffected by NA (FIG. 3D).

To explore the specificity of NA for CAG/CTG slipped-heteroduplexes, the effect of NA on the repair of the most frequent base-base mismatch, a G-T mispair, was assessed. Repair of this mispair depends upon the mismatch repair MutS beta complex (MSH2-MSH6). NA had no effect upon G-T repair, further indicating that NA does not block MMR and is unlikely to cause genome-wide mutations known to occur in the genetic absence of MMR (FIG. 3E). Thus, the preference of NA to block repair of long CAG slip-outs may forecast the ability to modulate repeat instability.

To address questions of potential therapeutic use of NA, it was determined that NA is cell-permeable and can enter the nuclei without causing acute cytotoxicity or slowed proliferation to human cells (FIG. 2E-2G) or DNA replication (FIG. 8).

Figure 9:
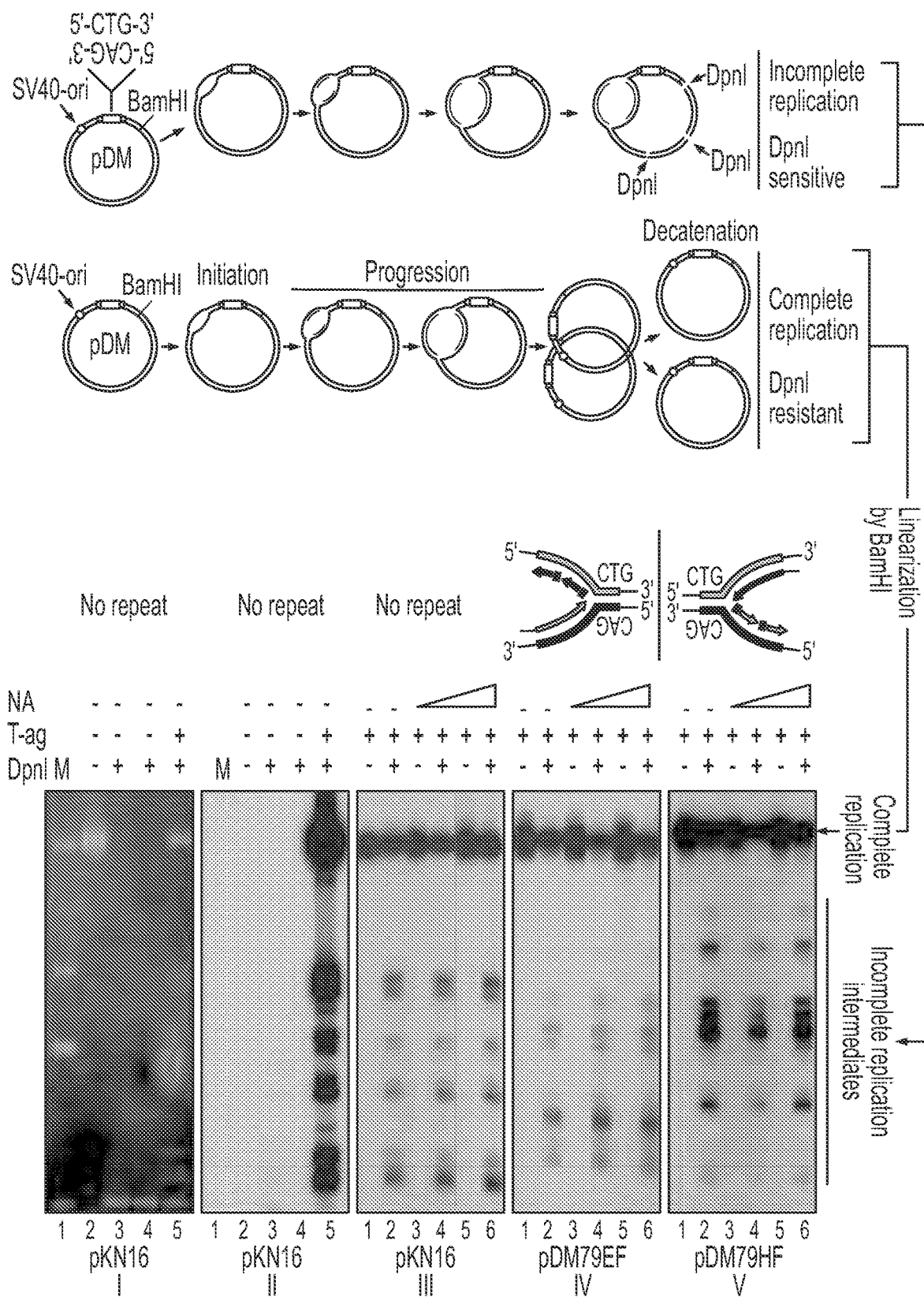
FIG. 9 shows that NA does not affect replication efficiency or replication fork progression, regardless of the presence of a CAG/CTG tract or replication direction. Three circular plasmids containing the SV40 origin of replication, and an expanded (CAG)79●(CTG)79 repeat tract (pDM79EF and pDM79HF) or no repeats (pKN16), were replicated in vitro by human HeLa cell extracts and added recombinant SV40 T-Ag, without or with NA (7.5 µM or 15 µM) treatment. The location of SV40-ori determines the replication direction and which strand will be used as the leading or the lagging strand template. pDM79HF uses the CAG strand as the lagging strand template, while pDM79EF uses the CTG strand as the lagging strand template (schematic on the top of the gel panel). Replication products were purified and linearized with BanHI. An equal portion of the reaction material was also digested with BamHI and Dpnl; DpnI digests un-replicated and partially-replicated material, as shown in the schematic (top figure). The digestion products were electrophoresed on a 1% agarose gel to resolve completely replicated and un-replicated material, as previously described (Panigrahi et al., 2002, J. Biol. Chem., 277:13926-34; Cleary et al., 2002, Nat. Genet., 31(1):37-46; bottom figure). An equal amount of unreplicated plasmid DNA was digested with DpnI and stained with ethidium bromide to show the complete digestion of unreplicated plasmid DNA (bottom panel). Panel I, ethidium bromide stained, Panel II, autorad: marker (lane 1); DpnI undigested plasmid DNA (lane 2); DpnI digested unreplicated plasmid DNA (lane 3-4); replicated plasmid DNA, DpnI resistant (lane 5). No difference in DpnI resistant material was observed between replication in the presence or absence of NA, in all the three templates tested (panel III, IV, and V).
Figure 10:
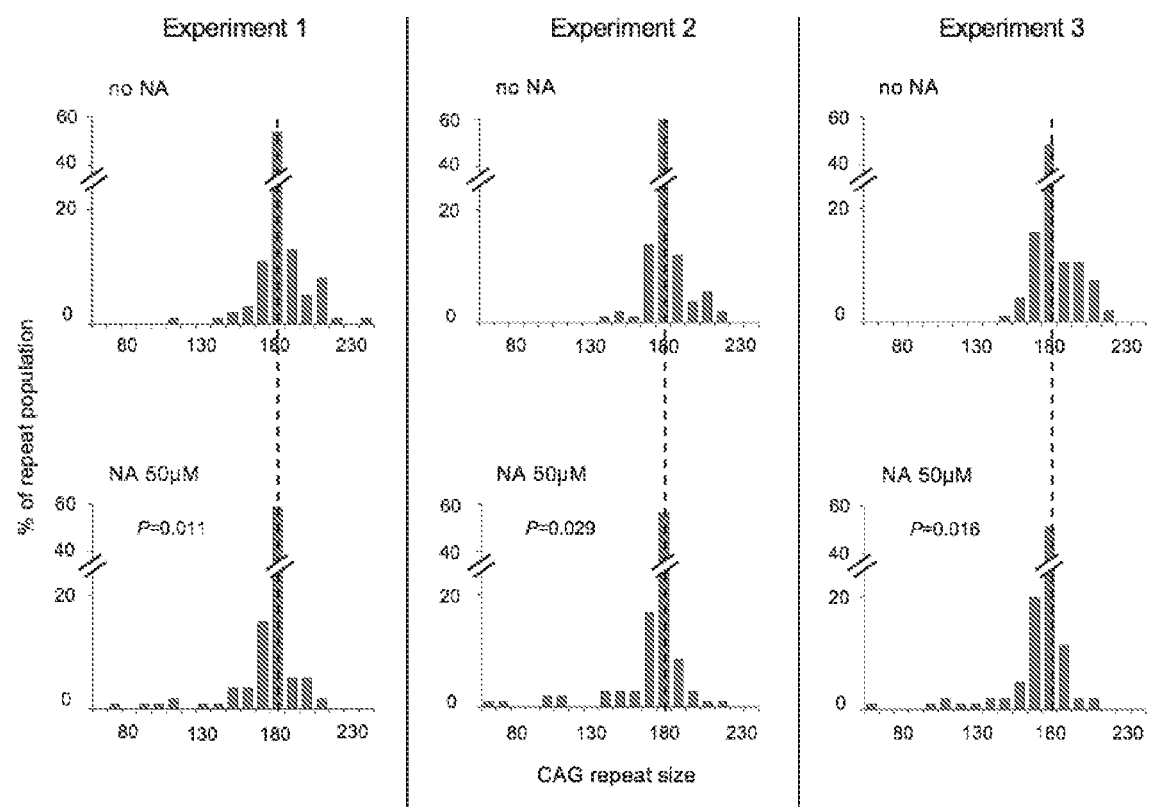
FIG. 10 shows an independent analyses of the effects of NA on repeat instability in HD fibroblast cells with a (CAG)180 expansion from 3 independent experiments. Small-pool PCR across the HD repeat tract was used to assess repeat instability. Histograms show the repeat-length distributions in the HD primary fibroblast cells after 40-days incubation with or without NA. The frequency distribution of repeat alleles is indicated as gray bars. Dashed lines indicate the peak CAG size.
Figure 11:
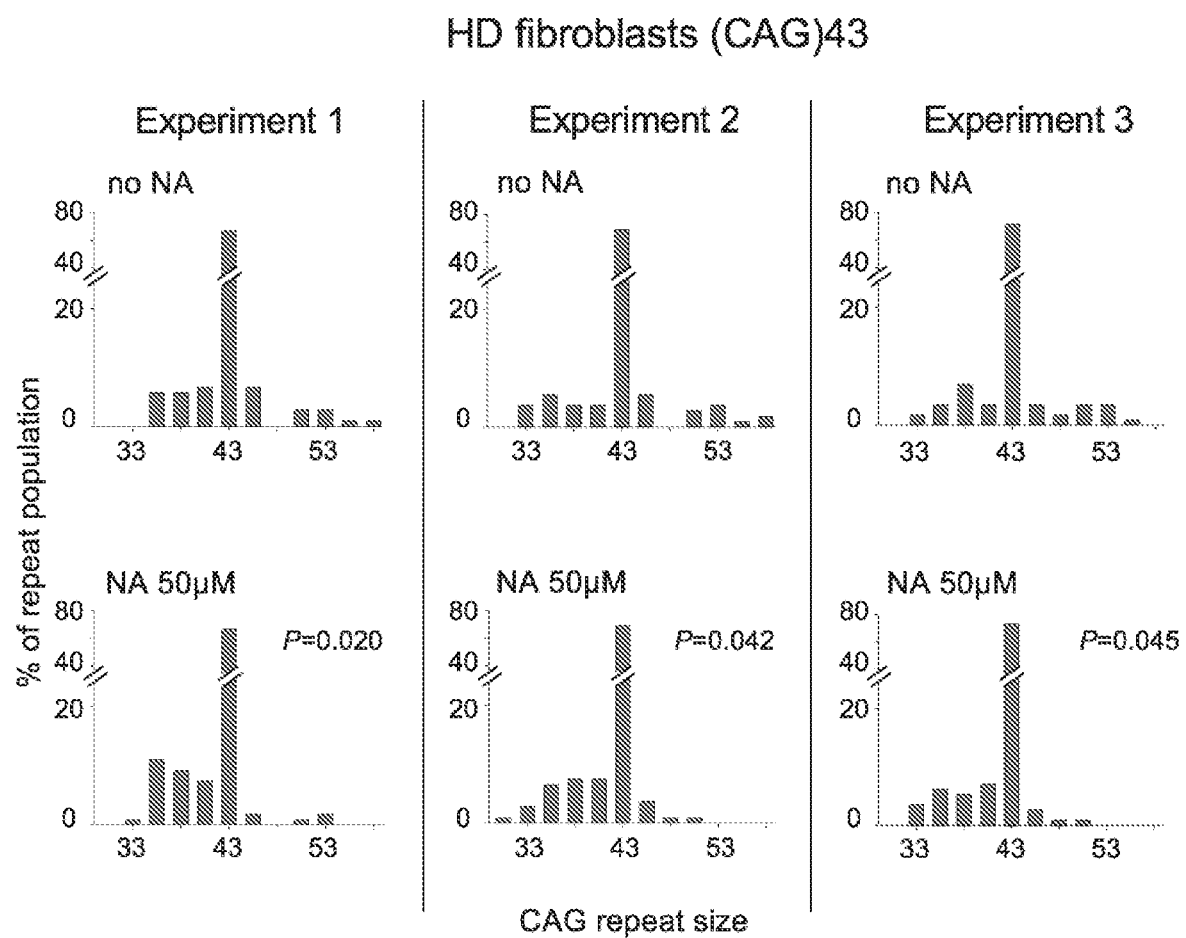
FIG. 11 shows the effects of NA on repeat instability in HD fibroblast cells with a (CAG)43 expansion from 3 independent experiments. Small-pool PCR across the HD repeat tract was used to assess repeat instability. Histograms show the repeat-length distributions in the HD primary fibroblast cells after 40-days incubation with or without NA. The frequency distribution of repeat alleles is indicated as gray bars. Dashed lines indicate the peak CAG size.
Figure 12:
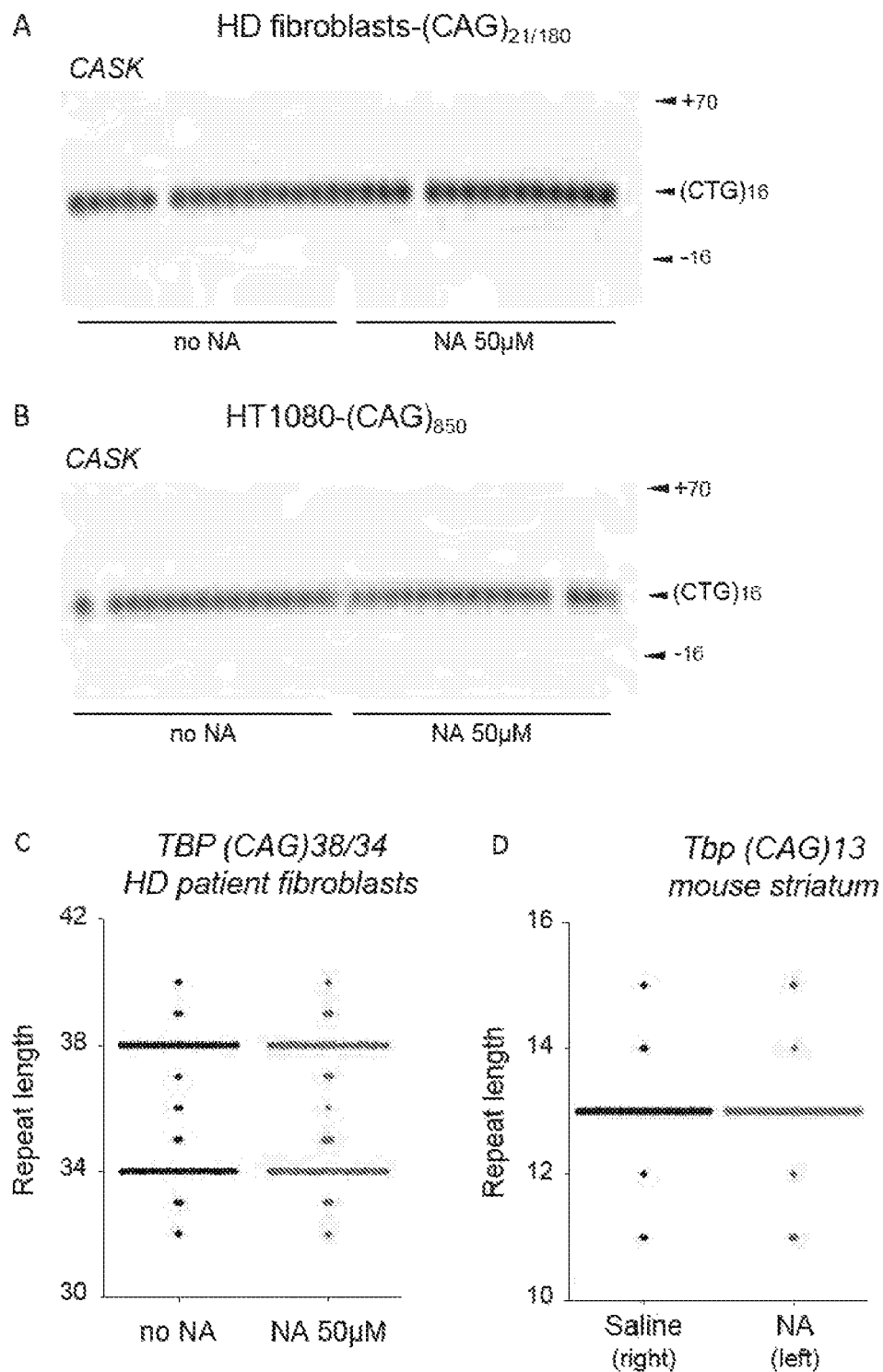
FIG. 12 are representative data showing ultra-sensitive small-pool PCR for the non-expanded CAG/CTG repeat length of CASK in HD primary fibroblast cells (Panel A of FIG. 12) and HT1080-(CAG)850 cells (Panel B of FIG. 12). Even under the highly sensitive mutation detection capacity of spPCR, length variation was not observed in either NA treated- and untreated-cells. Some reactions did not show any product, which is typical of the low genomic DNA template dilutions used in small-pool PCR. Repeat length variability in non-expanded CAG tracts in TBP alleles in HD patient fibroblasts treated with or without NA for 40 days (Panel C of FIG. 12) and in HD R6/2 mouse striatum with four injections of NA or saline (Panel D of FIG. 12). Repeat lengths were analyzed by Agilent BioAnalyzer.

Treatment of HD patient cells with NA induced contractions of expanded repeats. NA is cell-permeable and can enter the nuclei without causing acute cytotoxicity or slowing proliferation of human cells (FIG. 4A-4C) or altering DNA replication (FIG. 9). Tract lengths >200 repeats are frequent amongst brain cells that have incurred somatic expansions in HD individuals that inherited the common mutations of (CAG)40-50. NA induced a significant shift in repeat population towards contraction of a (CAG)180●(CTG)180 tract at the Huntington's disease locus in primary fibroblasts derived from an HD patient. NA enhanced the number of contractions of the expanded HD repeat (FIG. 4D; P=7.25E-06, FIG. 10, repeat analyses are summarized in Table 2, compiled from complete small-pool-PCR datasets for each repetition of each experiments), incurring significant losses of repeats (FIG. 4F; P=0.0003). NA also reduced the number of expansions of the expanded HD repeat (FIG. 4D; P=4.339E-05, FIG. 10, Table 2). An HD patient fibroblast also was treated with an expanded allele of 43 CAG repeats, a mutation common to the majority of patients. A significant number of NA-treated cells incurred contractions of the expanded repeat, with contractions as low as 20 repeats, below the HD disease threshold of 35 units (FIGS. 4E & 4G; P=3.28E-03, FIG. 11, Table 2). NA also reduced the number of expansions (FIG. 4E; P=8.32E-05, FIG. 4E; FIG. 11, Table 2). Thus, NA can induce contractions of expanded tract lengths common to inherited and somatically expanded alleles. In contrast, NA does not affect either the non-expanded HD repeat or other microsatellite repeats known to be prone to instability under stressed conditions (FIG. 4H & FIG. 12), suggesting that NA is specific for the expanded CAG/CTG repeat and will not deleteriously affect other repeats. As an additional control for the specificity of NA to slipped-DNA structures, the effect of NA was assessed at the very long, but not genetically unstable, CAG tract of the TBP gene in the NA-treated HD patient cells. The normal range of repeats in TBP is 25-41, while stretches of >49 repeats cause fully-penetrant disease (SCA17) and stretches of 42-48 are lead to reduced penetrance. In the HD patient cells, the non-mutant TBP gene has lengths of 38 and 34 repeats, above and just below the HD disease CAG length threshold of 34/35 repeats. Importantly, NA would only be expected to have an effect if the TBP repeat were actively undergoing events of instability that would lead to the formation of slipped-DNA structures—to which NA binds. Using established spPCR methods, NA did not change the length distribution of the TBP repeats (FIG. 12C, Table 2). Thus, the fact that NA has no effect upon the large, but not mutant repeat lengths at the TBP gene (FIG. 12C, Table 2), but did affect mutant HD tracts of (CAG)43-180 (FIG. 4D-4G), supports the specificity of NA for repeats actively undergoing instability, presumably involving slipped-DNAs. The inability of NA to affect a non-expanded repeat tract is likely due to the poor ability of short tracts to form slipped-DNAs, which is consistent with the absence of these structures at non-expanded loci. Moreover, sequence analysis of up to 2,402 individual alleles of the HPRT1 gene (exons 2 to 3), often used as a surrogate of mutation induction, did not show sequence changes for cells treated with NA (FIG. 13—see panel B) arguing against NA being a general mutagen. This finding is consistent with the inability of NA to affect base-base mismatch repair (FIG. 3E). Together, these results suggest that NA is specific for expanded repeat lengths that are commonly inherited and lengths that are frequent amongst brain cells that incurred somatic expansions, the effect of NA is specific for tracts that are actively unstable and will not deleteriously affect other repeats or sequences.

Figure 5A:
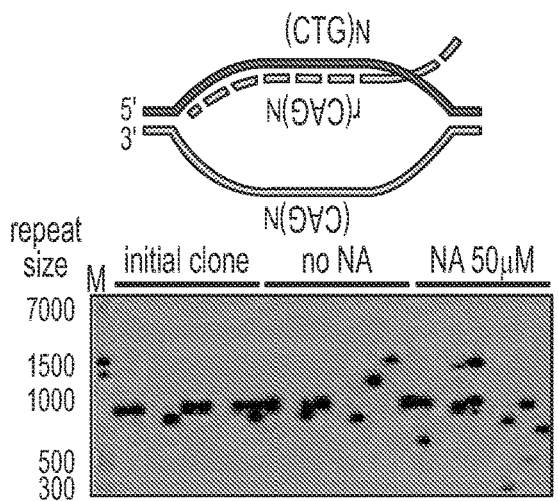
FIG. 5 are results from experiments showing that NA induces CAG contractions in HT1080-(CAG)850 cells, independent of proliferation, dependent upon rCAG transcription. Panel A of FIG. 5 shows a schematic transcription bubble, and representative data showing small-pool-PCR CAG/CTG repeat length analysis of HT1080-(CAG)850 cells (initial cell clone and cells after 30 days incubation with or without NA). Scale at left shows molecular weight markers (M) converted into repeat number for CAG-repeat fragments of equivalent size. Panel B of FIG. 5 are histograms showing repeat length distributions in HT1080-(CAG)850 cells. Frequency distribution of unstable alleles is shown by gray bars. Frequency of stable alleles is shown by black bars. To facilitate comparisons, a dashed line indicates the unchanged CAG size. Allele lengths are grouped in bins spanning 50 repeats. Percentage of repeat population was calculated by dividing the number of alleles grouped in bins spanning 50 repeats by the number of total alleles. More than 50 alleles were sized for each group. P-value was calculated by chi-square test (Table 2). Shown is a summary of 3 independent experiments (see FIGS. 10 & 11). Panel C of FIG. 5 shows the average repeat size change in HT1080-(CAG)850 cells after 30 days incubation with or without NA. P-value was calculated by Student's t-test. Panel D shows the repeat length distributions in non-proliferative HT1080-(CAG)850 cells with and without NA treatment, with average repeat size change shown below (see also FIGS. 15A & 15B). NA still has an effect, demonstrating that its activity is independent of cell proliferation. Panel E of FIG. 5 shows proliferating HT1080-(CAG)850 cells that do not transcribe the repeat (FIG. 16A) after 30 days with and without NA. Repeat length distributions and average repeat size changes are shown. NA has no effect, showing dependence upon transcription. Panel F of FIG. 5 shows that NA does not block transcription across the expanded CAG tract (see also FIGS. 10A & 10B). RNA transcript levels of transgene (transcript in the CAG-direction) in HT1080-(CAG)850 cells treated with or without NA (50 µM). Quantitative reverse transcription (RT)-PCR was performed using TaqMan Gene Expression assays. NA (50 µM) did not affect transcription of the CAG-repeats containing transcript. Data are the mean±SD of triplicates. Panel G of FIG. 5 shows the repeat-tract lengths of the CASK, ATXN8, and Mfd15 loci in HT1080-(CAG)850 cells (initial clone and cells after 30 days incubation with or without NA). Length variation was not observed at any of these repeats of normal length. loci in HT1080-(CAG)850 cells (after 30 days incubation with or without NA) (see also FIGS. 12A & 12C).
Figure 5C:
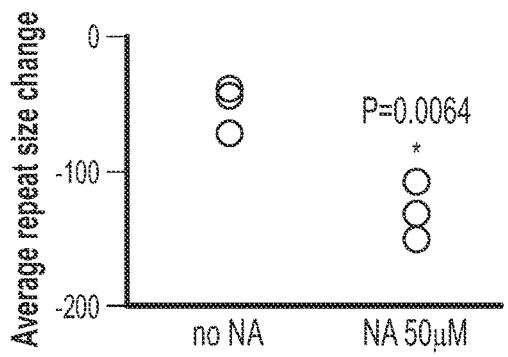
Figure 5F:
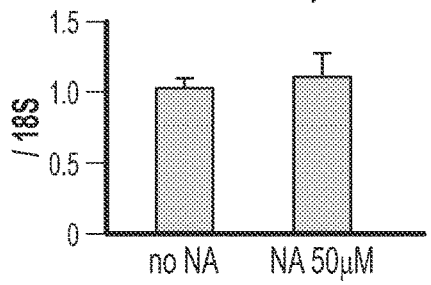
Figure 5G:
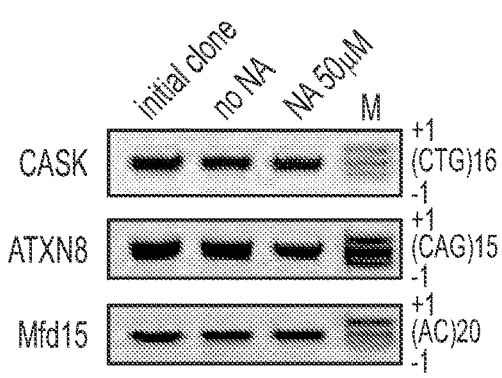
Figure 5B:
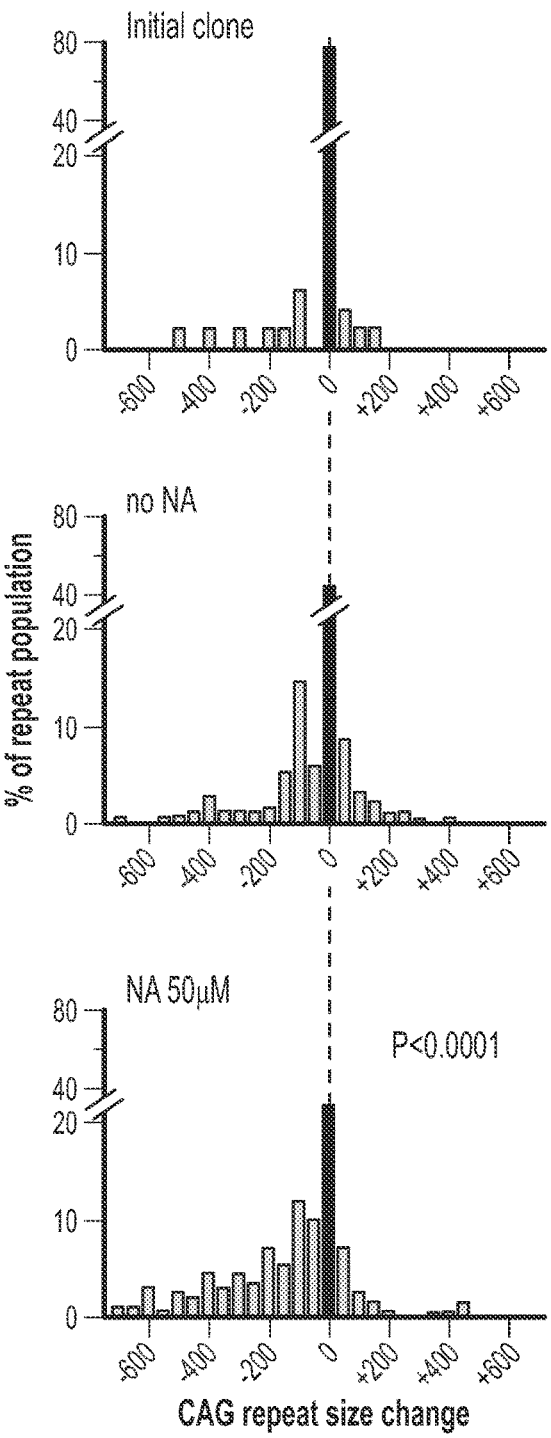

NA induced a significant shift in repeat population towards contraction of a (CAG)850●(CTG)850 tract in human cells, expressing r(CAG)850 (Nakamori et al., 2011, Human Mol. Genet., 20:580-8) (FIGS. 5A and 5B, and FIG. 14; P=4.78E-05, repeat analyses are summarized in Table 2). NA significantly shortened the average size of the repeat tract, where the magnitude of repeat units lost was as great as 790 repeats (FIG. 4C; P=6.44E-03). The effect of NA was independent of cell proliferation and DNA replication (FIG. 5D, FIG. 15), consistent with NA's lack of an effect upon cell proliferation (FIG. 4C) or replication progression (FIG. 9). The effect of NA depended upon transcription across the repeat (FIG. 5E, FIG. 16A-16C), yet NA did not alter transcription across the expanded repeat (FIG. 5F). NA does not affect non-expanded CAG/CTG tracts or other microsatellite repeats (FIG. 5G and FIG. 12). Together, these results suggest that NA is effective independent of proliferation and dependent upon transcription across the repeat.

Transcriptionally-induced R-loops can lead to CAG/CTG instability. The transcription dependency of NA upon repeat instability that was observed above (FIG. 5E) might suggest NA may affect either transcription, R-loop formation, biophysical stability of R-loops, and/or R-loop processing to instability. These alternatives were tested and found that NA did not alter transcript levels of the expanded repeat in cells (FIG. 5F, FIG. 16A-16C), nor did it affect transcription in vitro (FIG. 17B). NA (120 µM) did not affect R-loop formation (FIG. 17B), nor RNaseA or RNaseH processing of pre-formed R-loops (FIG. 17C). At NA concentrations similar to that used on cells (50 µM) or higher (500 µM), R-loops were still detectable suggesting that NA did not affect the biophysical stability of R-loops (FIG. 17D). However, NA altered the processing of CAG/CTG R-loops by extracts of neuron-like human SH-SY5Y cells, significantly increasing the number of contraction products but not expansion products (FIG. 18C, p=0.002). Results from these model systems suggest NA causes preferential R-loop processing to repeat contractions.

A plausible mechanism for NA to enhance contractions of expanded repeats is through the aberrant repair of slipped-DNAs that arise from transcription-induced R-loops—a path that is supported by the data presented herein as well as other reports (Nakamori et al., 2011, Human Mol. Genet., 20:580-8; Lin et al., 2010, PNAS USA, 107:692-7; Reddy et al., 2014, Nuc. Acids Res., 42:10473-87). As outlined in FIG. 19, during transcription of the CTG strand to produce a CAG transcript, as occurs at the HTT gene, there is a predisposition to form slipped-DNAs on the displaced CAG DNA strand, NA may bind the intra-strand hairpins formed on the displaced dCAG strand and possibly further extend these to longer hairpins (FIG. 19A). These NA-bound slipped-DNAs would escape repair and lead to contractions. When retaining or removing slip-outs, by endonucleolytic incisions (Hou et al., 2009, Nature Struct. Mol. Biol., 16:869-75; Pluciennik et al., 2013, PNAS USA, 110, 12277-82) (see arrows in FIG. 19B), DNA repair synthesis on NA-bound (CAG)n templates will be blocked (Hagihara et al., 2006, Nuc. Acids Symp. Ser. (Oxf.), 50:147-8; Hagihara et al., 2011, Chembiochem., 12:1686-9), thereby favouring contractions over expansions. This model is consistent with NA inducing repeat contractions in the absence of DNA replication, in a transcription-dependent manner, where NA exerts its effect via perturbing repair of repeat structures (FIGS. 3-5).

There are many paths by which repeat instability can arise, and various ways through which NA may act (DNA replication, transcription, epigenetic changes, DNA-damage, etc), all of which involve slipped-DNAs. That the effect of NA upon CAG instability was independent of proliferation/replication (FIG. 5D) and dependent upon transcription through the repeat (FIG. 5E), coupled with the dependence of CAG instability upon transcription, the formation of slipped-DNAs through R-loop processing, the likely involvement of slipped-DNAs in instability, the specificity of NA for CAG hairpins (FIG. 2), and NA's ability to block repair of CAG contraction intermediates (FIG. 3B) all support this proposed model.

Might NA act by blocking the interaction of DNA repair proteins with slipped-DNAs? While the proteins required for large slip-out repair are not known, towards testing this hypothesis we assessed the effect of NA upon four candidate proteins MutS beta, FAN1, and RPA-pol delta. Many mouse models demonstrate that the mismatch repair MutS beta complex with a functioning ATPase, drives CAG/CTG expansions. While NA blocks the repair of a large CAG slip-out of 20 excess repeats, a process that is independent of MutS beta, we, and others have suggested that MutS beta may be involved in the formation of slipped-DNAs which subsequently lead to expansions. This process, expected to involve MutS beta binding to DNA, may be affected by NA. Here, it was found that MutS beta can bind long CAG slip-outs repeats, a complex that can be dissociated by ATP (FIG. 20), similar to previous reports. NA did not block binding of MutS beta to CAG slip-outs or block ATP-mediated dissociation of this complex (FIG. 20). Since NA does not block MutS beta from binding slip-outs, and since NA does not disallow formation of slip-outs from denatured repeat-containing DNAs (FIG. 2E), does not support a role of NA in blocking the formation of slipped-DNAs either alone or enhanced by MutS beta. MutS beta, if involved in the action of NA upon repeat instability, likely acts upstream, possibly forming slipped-DNAs during transcription, as suggested.

Figure 22A:
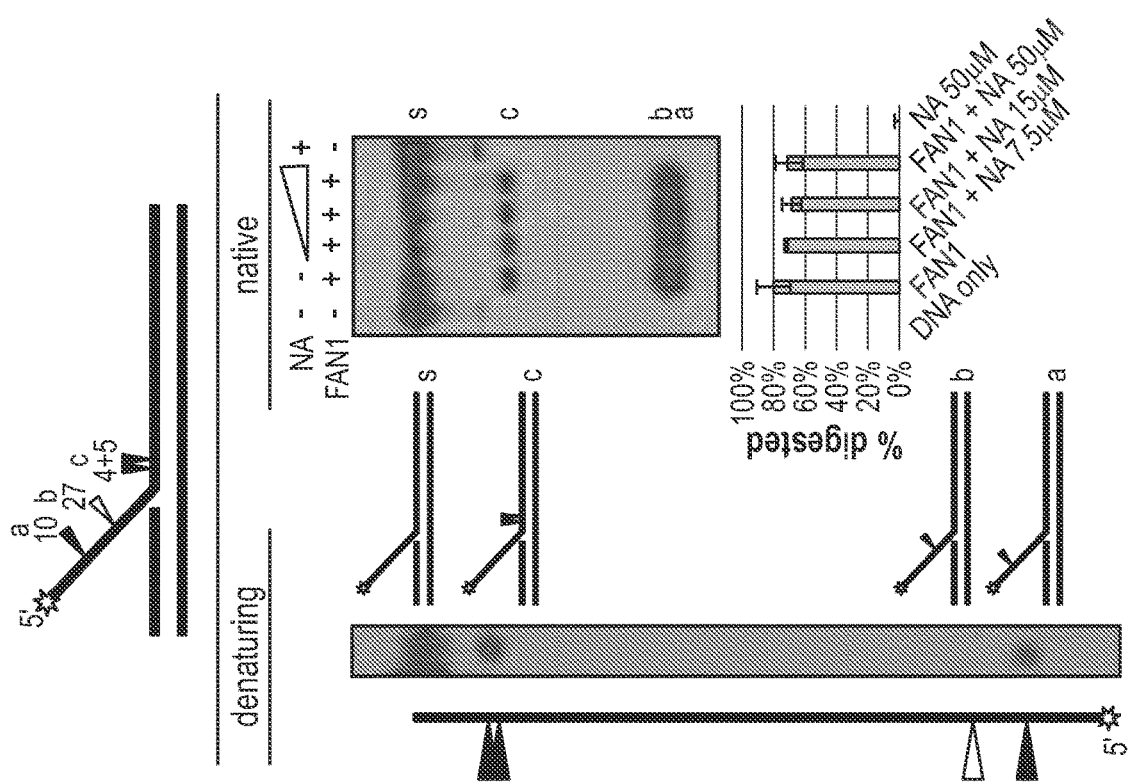
Figure 22B:
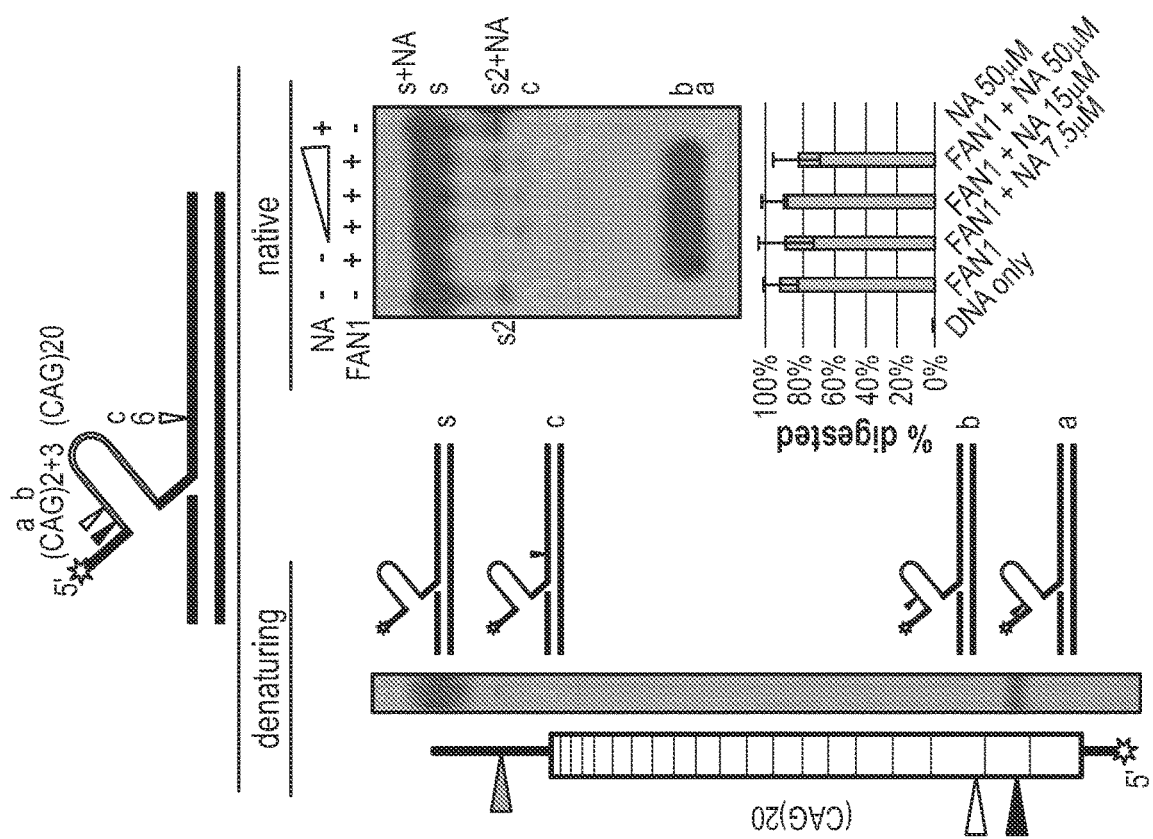
Figure 22C:
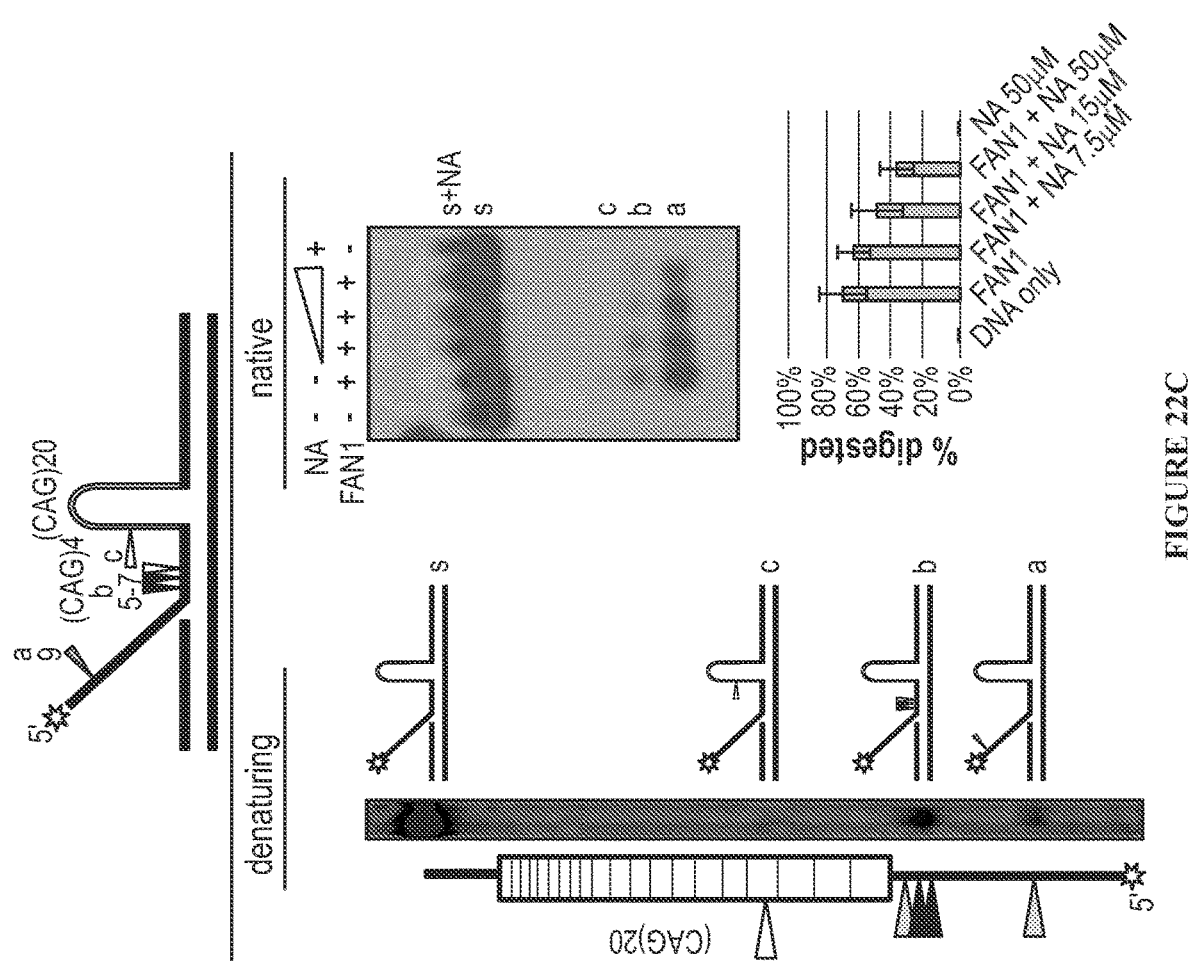
Figure 22E:
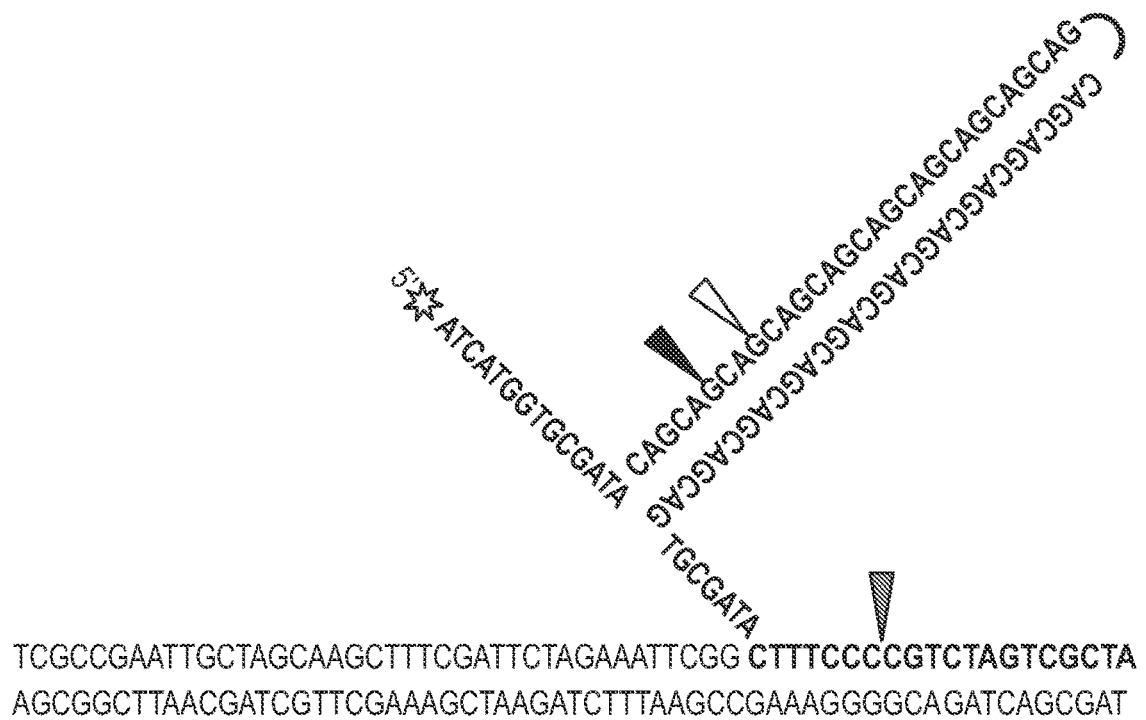
Figure 22F:
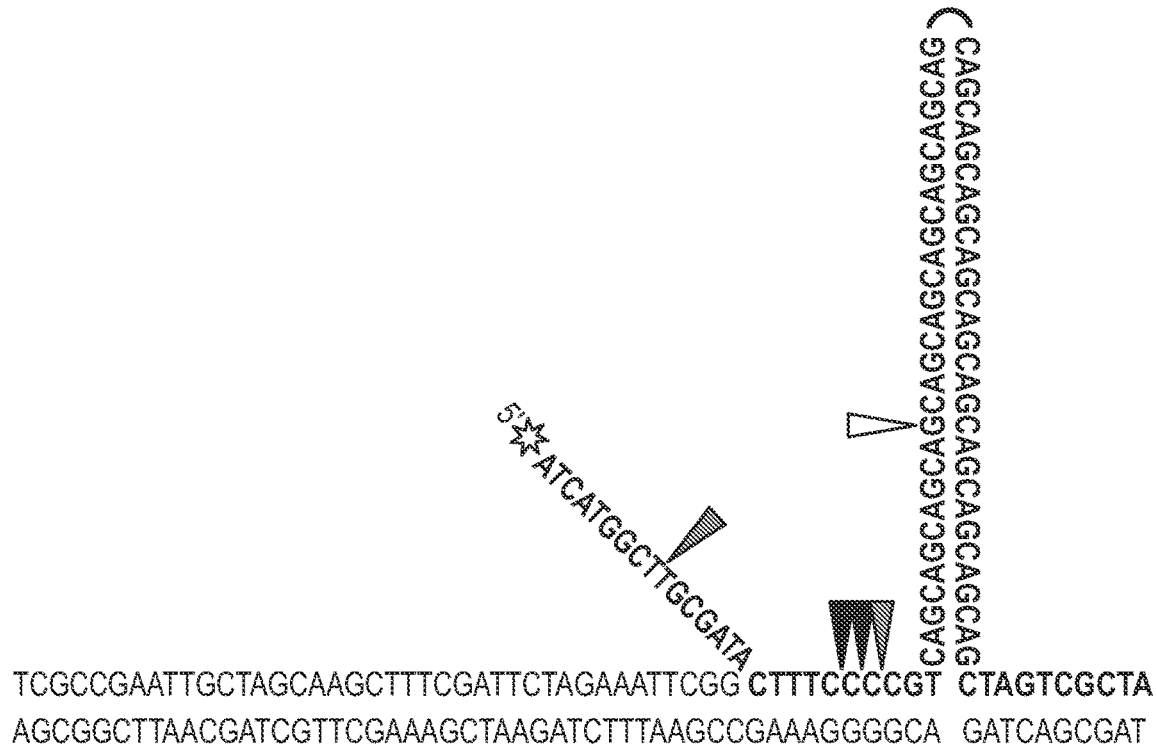

FAN1/KIAA1018/MTMR15, initially identified in brain, is a DNA repair nuclease with a preference for DNA structures. FAN1 was recently identified as the top in several searches for modifiers of age-of-onset of HD and five other CAG diseases (SCA1, SCA2, SCA3, SCA7, & SCA17). While the manner by which FAN1 modulates age-of-onset is unknown, it could be speculated to do so by modulating somatic repeat instability. The action of FAN1 upon repeat DNAs was tested, for which there is no precedent. As previously demonstrated, FAN1 can cleave supercoiled and linear DNAs (FIG. 21, left panel), and can cleave transcription-induced R-loop containing DNAs—thereby releasing the supercoil-dependent RNA portion (FIG. 21, right panel). Slipped-DNAs may arise from misaligned DNA annealing following loss of the RNA from R-loops. FAN1 cleavage was mapped on three different slipped-DNA junctions: a control junction devoid of repeats; one with a CAG hairpin in the flap; and one with a CAG hairpin in the duplex region beyond the junction (FIG. 22, top panels: Table 1). As with other studies, FAN1 cuts in the 5' single-strand flap and in the duplex beyond the flap. Cleavage at both sites is approximately equal for the control substrate (FIGS. 22A & 22D). However, for the CAG-substrates, cleavage is reduced at the duplex and hairpin regions (FIGS. 22B-22C & 22E-22F, denaturing gels, see arrowheads). This suggests that the presence of a CAG hairpin may affect FAN1 activity. Inclusion of increasing amounts of NA in the reaction markedly reduced nuclease activity on the CAG in-duplex substrate, specifically affecting cleavage proximal to and within the CAG hairpin (FIGS. 22C & 22F). The demonstration herein that FAN1 cleavage of a slipped-CAG substrate can be altered by NA, a drug that has been shown to modify CAG instability (FIGS. 3, 5 & 6), supports the possibility that NA can modify the action of a DNA structure-specific nuclease, FAN1. The manner by which FAN1 may modulate HD age-of-onset is a focus of future studies.

Replication Protein A (RPA), a key player in many DNA repair processes, inhibits the formation of unusual DNA structures, like hairpins, through binding and stabilizing single-stranded regions. RPA has been reported to enhance DNA polymerase progression through difficult DNA templates by melting the structured template. The effect of NA upon RPA-binding to slipped-DNAs was assessed and upon enhancing progression by polymerase delta (pol delta, a polymerase implicated in CAG repeat instability) and active in brains in a repair capacity. NA competitively blocked the interaction of RPA to slipped-CAG repeats (FIG. 23A). Pol delta was unable to synthesize across a CAG tract and this was rescued by the addition of RPA, likely through its ability to melt the impeding hairpin (FIG. 23B, lanes 2-4). NA blocked the enhanced progression of pol delta along the CAG template (FIG. 23A, lanes 5-6), a result consistent with NA binding competitively against RPA for the CAG tract (FIG. 23A). These results support a mechanism of NA inducing CAG contractions through an inability of polymerases to synthesize through NA-bound CAG templates (FIG. 23C). This result supports a process by which NA may induce contractions (see lower portion of FIG. 19). Together, our FAN1, pol delta, and RPA results provide proof-of-principle supporting the concept that NA may act by disrupting interaction or activity of repair proteins on CAG slip-outs. Defining the exact players and steps that NA can alter to induce CAG contractions is to be determined.

Would NA be effective in vivo in neural tissues that show rampant CAG expansions and are susceptible to degeneration? In both mice and patients, the largest CAG expansions and most degeneration occur in the striatum (Lopez Castel et al., 2010, Nature Reviews, Mol. Cell. Biol., 11:165-170; Kennedy et al., 2003, Human Mol. Genet., 12:3359-67; Goula et al., 2009, PLoS Genet., 5:e1000749; Larson et al., 2015, Neurobiol. Dis., 76:98-111; Kovalenko et al., 2012, PLoS One, 7:e44273), with the medium-spiny neurons being the most vulnerable and incur the greatest CAG expansions (Kovalenko et al., 2012, PLoS One, 7:e44273). Therefore, the effect of NA on the instability of the expanded (CTG)150 in Huntington's disease R6/2 transgenic mice was tested, each inheriting around 150-160 CAG repeats, focusing upon the striatum (Goula et al., 2009, PLoS Genet., 5:e1000749; Larson et al., 2015, Neurobiol. Dis., 76:98-111), where each mouse was injected with either NA+saline on the left striatum or with saline only on the right, as an internal control, spanning 4-weeks (FIG. 24). CAG expansions are evident in the striatum of these mice as early as a few weeks, which continue as the mice age (Goula et al., 2009, PLoS Genet., 5:e1000749; Larson et al., 2015, Neurobiol. Dis., 76:98-111). In one model, the CAG repeats have been quantified to gain broadly distributed sizes of additional repeats at a rate of ~3.5 CAG unit per month per cell (Lee et al., 2011, PLoS One, 6:e23647; Mollersen et al., 2010, PLoS Genet., 6:e1001242). Repeated intra-striatal injections of NA (dissolved in saline) in 6-week-old R6/2 mice led to seeming contractions of the expanded repeat, relative to saline-only injections into contralateral striatum of the same mice (FIG. 6A, compare blues scans NA-treated with red scans saline-treated striatal portions, injections were once, twice, or four administrations spanning four weeks when DNAs were harvested (FIG. 24)). The effect of NA was localized to the injection site, so only the NA-injected (blue scans), but not the saline injected striatal regions (red scans), showed repeat contractions, thereby permitting the saline injected half of the same mouse brain to serve as an internal control. In the absence of any treatment, for a given mouse the CAG length distributions between left and right halves of the striatum were indistinguishable. That the NA (in saline) treated half has shorter CAG tracts than the saline only treated half supports the interpretation that NA induced the CAG length differences (FIG. 6A).

Continued contractions were induced with additional NA administrations over a four-week period (this was highly reproducible for a total of 13 mice (one for 1 injection, two for 2 injections, and ten for 4 injections, see FIG. 25A-25H, NA injection did not alter brain morphology, FIG. 26). The effect of NA is consistent between mice, regardless of inherited repeat length differences between mice. A bimodal distribution of repeat sizes is present in HD patient brains. This second peak of larger expansions is evident in the striatum of most CAG mouse models and was found to consist of the most vulnerable HD cells, the medium spiny neurons and to have greater levels of expanded CAG transcript. Interestingly, NA had a greater effect upon the larger expansions of the bimodal repeat distribution (FIG. 6D). This portion of larger sized expansions in the striatum may have arisen by mutation events involving large slip-outs, large enough to be bound by NA. Instability analyses in HD individuals suggests that the number of CAG units gained or lost at each mutation event are predominantly changes of one repeat unit, but may include changes of 5-15 repeat units, sizes that could be bound by NA. It is noteworthy that slipped-DNAs at the DM1 locus, isolated from various tissues of DM1 patients, including brain, presented a bimodal distribution of slip-out sizes, with peaks of ~30 and <10 repeats, where the former could be bound by NA.

Most, if not all, alleles in the NA-treated striatum had incurred repeat contractions, indicating that NA had affected most cells (FIG. 6A, FIG. 25A-H). Using an established method, the somatic "instability index" was quantified: greater indices reflect greater expansions, lower indices reflect lower expansions or greater contractions (FIG. 27). The number of contracted versus expanded peaks (FIG. 6B) or the relative composition (%) of contracted versus expanded peaks (FIG. 6C) was greater with subsequent treatments. The repeat size distributions in striatum treated four times with NA were significantly different from the mock-treated striatum (Mann-Whitney, p=00.00034, or paired t-test, p-0.000019). The effect of NA was localized to the site of injection, as the CAG tract in the cerebral cortex and cerebellum from the same mice that had intra-striatal injections showed identical patterns of CAG length heterogeneity in the right and left sides (FIGS. 6C and 6D, FIG. 25A-25H).

Figures 5D, 5E:
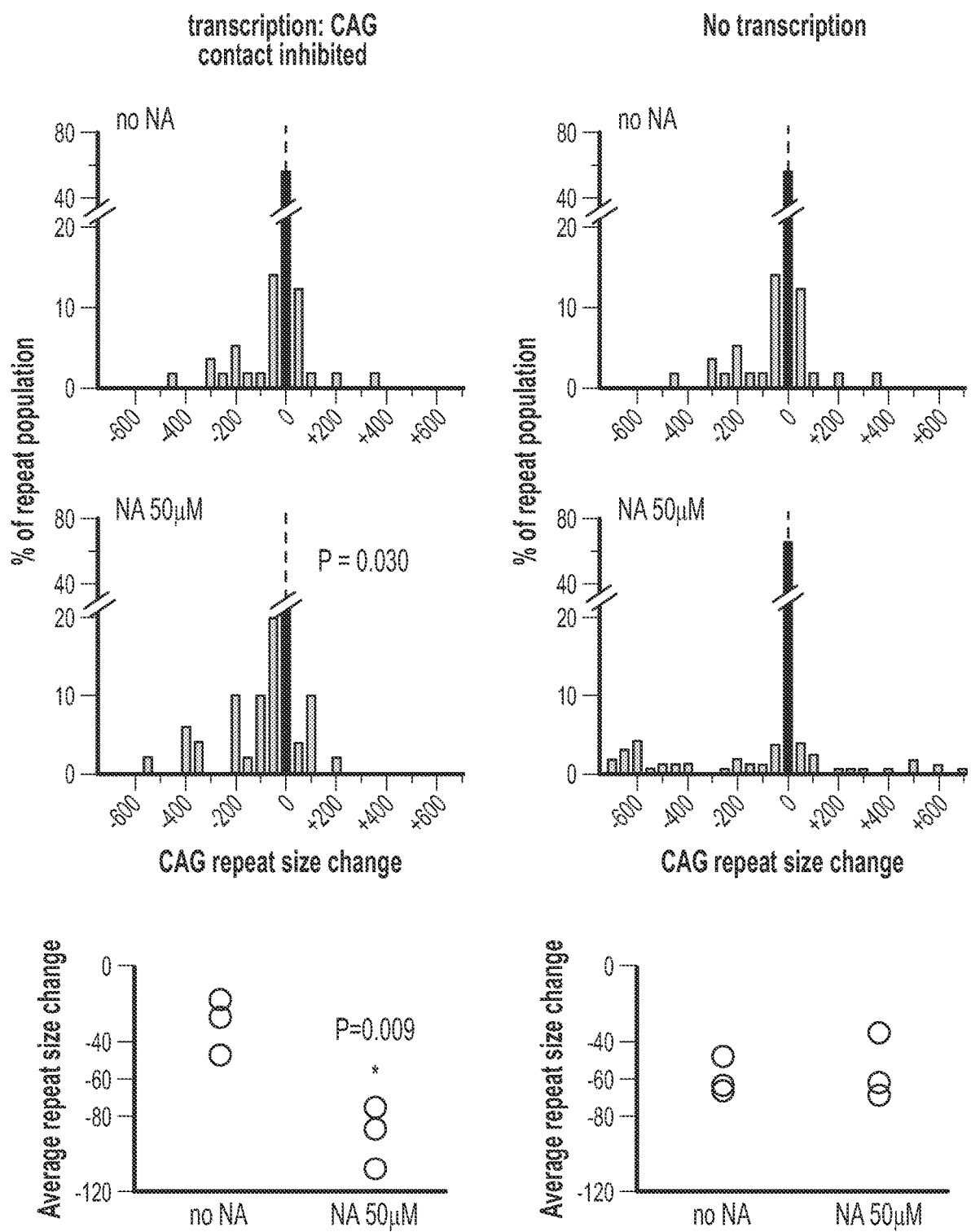

That NA induced contractions, rather than only arresting expansions, is supported by the fact that the peak repeat length in the NA-treated striatum was shorter than the inherited tract length in the tail of the same mouse, which does not change through the life of the mouse (FIG. 5D and FIG. 25). Importantly, for a given mouse, the repeat size distributions in the half of the striatum treated with NA were shifted towards contraction, relative to the inherited length in the tail, while the saline-treated half of the striatum continued to incur expansions (FIG. 6B-6E, FIG. 25A-25H, see delta of main peaks where the saline—versus the NA-treated versus the tail CAG lengths differ by 4-7 CAG units). This suggests that injections of NA into the striatum induced contractions of the expanded CAG tract, and can do so countering the expansion-bias in that tissue (showing a spontaneous expansion rate of ~5.75 CAG units/month), a finding that is consistent with the NA-induced contractions observed in cells (FIG. 3 and FIG. 5). The effect of NA in vivo was specific for the expanded repeat, having no effect upon non-expanded repeats (FIGS. 6E and 12D). The effect of NA likely involved genome maintenance rather than DNA replication, as the 6-week-old treated mice had passed the postnatal 'brain growth spurt', where replication peaks 6-17 days after murine birth. It is likely that it involved transcription as CAG-RNA levels were greatest in striatal cells with the largest expansions and NA did not alter transcription across the repeat (FIG. 16C). This is consistent with NA inducing contractions independent of cell proliferation (FIG. 5E). Thus, NA could induce contractions of expanded CAG repeats in most cells in a tissue, which, in HD individuals, show selective neuronal vulnerability.

These findings in mice with about 150 CAG repeats over a four-week period of NA treatment shows neurons en masse incurred contractions of ~0.5 repeats lost/week. Extrapolating this to an HD-affected human, applying a drug like NA prior to the rapid onset of somatic CAG expansions could effectively block expansions and induce contractions of the inherited expanded allele to shorter lengths, where treatments spanning one year could contract the repeat by 5-25 repeats. For an above average HD allele of 60-70 repeats, this could be significant and modify disease onset and progression.

Data from diverse approaches using multiple model systems led to harmonious interpretations. For example, the NA-enhanced contractions in various cell models are consistent with the increased contractions in vivo, and the absence of an effect of NA at replication forks and an independence from replication but a requirement of transcription are all consistent with the absence of a requirement of proliferation in cells or striatum where transcription occurs. In addition, that NA affects R-loop processing to contractions is consistent with NA affecting instability in cell lines and striatum undergoing transcription producing rCAG-dCTG R-loops, displacing the CAG DNA strand and allowing it to be bound by NA. Further, that NA binds to and inhibits repair of long, but not short, CAG slip-outs is consistent with NA preferentially affecting the larger repeat sizes in striatum, which undergo large salutatory expansions.

Previous studies using cell models of CAG/CTG instability demonstrated that exogenously added compounds can modulate levels of repeat instability (Yang et al., 2003, Am. J. Hum. Genet., 73:1092-105; Gomes-Pereira et al., 2006, Mutat. Res., 598:15-34). However, the effective compounds were DNA damaging agents lacking specificity for the expanded repeat (ethylmethanesulphonate, ethidium bromide, mitomycin C and DNA polymerase inhibitors), and, thus, would induce deleterious mutations throughout the genome. In a separate strategy, a (CAG)6 antisense oligonucleotide was able to reduce instability of a (CTG)800, but did not induce contractions of an expanded repeat (Nakamori et al., 2011, Mol. Ther., 19:2222-7).

A mitochondria-directed compound, XJB-5-131, by unknown processes, was reported to mildly suppress CAG expansions rather than induce contractions; this compound also suppressed contractions. A sequence-specific polyamide directed to the duplex GAA repeat that is expanded in Friedreich's ataxia patients prevents GAA triple-stranded structure formation and suppressed GAA repeat expansions in FRDA cells, but did not induce contractions. CRISPR/Cas9 treatment of HD cells, to target the mutant allele, deleted ~44 kb DNA spanning promoter region, transcription start site, and the CAG expansion of the mutant HTT allele, resulting in haplo-insufficiency with a functional non-mutant allele. A small molecule approach may overcome some of the in vivo hurdles (delivery, specificity, etc.) of enzyme-mediated paths.

In contrast to these previous approaches, our results indicate that NA, a DNA ligand that binds slipped-strand DNA structures comprised of CAG repeats, can shift the dynamic of repeat instability in favor of contractions rather than further expansions. NA likely acts by inhibiting cycles of aberrant repair of slipped-DNA, possibly by perturbing the interaction of DNA repair proteins with the slipped-DNA. Other nucleic acid binding compounds demonstrated to be effective towards attacking deleterious repeat r(CUG) RNA-protein interactions or CAG/CTG transcription (Bernat et al., 2015, Neuron, 87:28-46) may also affect repeat instability. The attributes of NA—its sequence- and structure-specificity, its preferential effect upon expanded repeat harboring slipped-DNAs, its ability to induce contractions in vivo in an affected brain region—make it a first-in-class example showing the potential of small molecule DNA-binding compounds to impact CAG repeat instability by inducing contractions and inhibiting expansions of disease-causing expanded repeats. Administration of such small molecules, once optimized for therapy, to human brains might effectively target the root cause and address all downstream effects caused by the expansion mutation.

TABLE 2

| | | | | | | | Average Change of | |
| Cell Type | Study | Treatment | % Expansion[a] | % Unchanged | % Contraction[a] | P value[b] | Repeat Size[c] | P value[c] |
|---|---|---|---|---|---|---|---|---|
| HT1080-(CAG)850 | Initial Clone | | 7.7 | 76.9 | 15.4 | | −28.8 | |
| | Ex 1 | No NA | 8.8 | 49.1 | 42.1 | 0.042 | −68.1 | |
| | | 50 uM NA | 14.8 | 28.4 | 56.8 | | −107.2 | |
| | Ex 2 | No NA | 21.1 | 45.1 | 33.8 | 0.008 | −36.1 | |
| | | 50 uM NA | 11.3 | 27.4 | 60.0 | | −129.3 | |
| | Ex 3 | No NA | 21.8 | 43.6 | 34.5 | 0.017 | −41.3 | |
| | | 50 uM NA | 15.2 | 23.7 | 61.0 | | −147.1 | |
| | Total | No NA | 17.5 | 45.9 | 36.6 | 4.78E−05 | −47.2 | 6.44E−03 |
| | | 50 uM NA | 13.9 | 26.7 | 59.4 | | −125.7 | |
| HT1080-(CAG)850 contact inhibition | Ex 1 | No NA | 26.8 | 46.4 | 26.8 | 0.036 | −17.9 | |
| | | 50 uM NA | 15.9 | 34.9 | 49.2 | | −86.9 | |
| | Ex 2 | No NA | 22.0 | 44.0 | 34.0 | 0.049 | −46.8 | |
| | | 50 uM NA | 17.9 | 25.0 | 57.1 | | −107.6 | |
| | Ex 3 | No NA | 17.5 | 52.6 | 29.8 | 0.030 | −26.2 | |
| | | 50 uM NA | 16.0 | 30.0 | 54.0 | | −105.0 | |
| | Total | No NA | 22.1 | 47.9 | 30.1 | 8.78E−05 | −30.0 | 9.36E−03 |
| | | 50 uM NA | 16.6 | 30.2 | 53.3 | | −90.9 | |
| HT1080-non transcribing (CAG)850 | Ex 1 | Nona | 14.0 | 62.0 | 24.0 | 0.862 | −48.5 | |
| | | 50 uM NA | 11.1 | 66.7 | 22.2 | | −68.8 | |
| | Ex 2 | No NA | 15.5 | 62.1 | 22.4 | 0.990 | −64.4 | |
| | | 50 uM NA | 16.1 | 62.5 | 21.4 | | −36.6 | |
| | Ex 3 | No NA | 9.8 | 67.2 | 23.0 | 0.976 | −66.1 | |
| | | 50 uM NA | 9.1 | 69.1 | 21.8 | | −62.8 | |
| | Total | No NA | 13.0 | 63.9 | 23.1 | 0.918 | −60.3 | 0.766 |
| | | 50 uM NA | 12.1 | 66.1 | 21.8 | | −55.9 | |
| HD fibroblasts (CAG)180 | Ex 1 | No NA | 28.0 | 54.0 | 18.0 | 0.011 | 187.0 | |
| | | 50 uM NA | 12.6 | 58.6 | 28.8 | | 178.5 | |
| | Ex 2 | No NA | 22.9 | 59.6 | 17.4 | 0.029 | 185.8 | |
| | | 50 uM NA | 13.1 | 56.1 | 30.8 | | 176.5 | |
| | Ex 3 | No NA | 30.5 | 48.4 | 21.1 | 0.016 | 187.5 | |
| | | 50 uM NA | 15.1 | 50.9 | 34.0 | | 177.5 | |
| | Total | No NA | 27.0 | 54.3 | 18.8 | 7.25E−06 | 186.7 | 2.90E−04 |
| | | 50 uM NA | 13.6 | 55.2 | 31.2 | | 177.5 | |
| HD fibroblasts (CAG)43 | Ex 1 | No NA | 14.4 | 67.3 | 18.3 | 0.020 | 43.7 | |
| | | 50 uM NA | 4.6 | 67.0 | 28.4 | | 40.6 | |
| | Ex 2 | No NA | 14.7 | 68.8 | 16.5 | 0.042 | 43.2 | |
| | | 50 uM NA | 5.6 | 69.2 | 25.2 | | 40.4 | |

TABLE 2-continued

Results from Small Pool PCR

| Cell Type | Study | Treatment | % Expansion[a] | % Unchanged[a] | % Contraction[a] | P value[b] | Average Change of Repeat Size[c] | P value[f] |
|---|---|---|---|---|---|---|---|---|
| | Ex 3 | No NA | 12.9 | 71.6 | 15.5 | 0.045 | 43.3 | |
| | | 50 uM NA | 4.5 | 73.2 | 22.3 | | 41.0 | |
| | Total | No NA | 14.0 | 69.3 | 16.7 | 3.28E−05 | 43.4 | 2.94E−04 |
| | | 50 uM NA | 4.9 | 69.8 | 25.3 | | 40.7 | |

Data summarized from analysis of HD patient fibroblasts (GM09197; (CAG)180 and GM02191, (CAG)43), and HT1080-(CAG)850, presented in FIGS. 5, 6, and FIGS. 10 and 11, 14, and 15.
[a]A cut-off point of ±25 repeats was used to determine expansion and contraction.
[b]P-values were calculated using the $\chi^2$ test to compare the proportions of expanded, unchanged, and contracted alleles within the population of HT1080-(CAG)850 cells.
[c]for all alleles (expanded + unchanged + contracted), the average change in the repeat size is expressed as the number of repeats. Note that the average change in the repeat size was biased toward contraction because of the preferential amplification of shorter alleles by small pool PCT.
[d]A cut-off point of ±10 repeats was used to determine expansion and contractions.
[e]P-values were calculated using the $\chi^2$ test to compare the proportions of expanded, peak repeat, and contracted alleles within the populations of HD fibroblasts.
[f]P-values were calculated by Student's t test.

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method of inhibiting the expansion or inducing the contraction of a repeat DNA sequence in a cell, comprising:
   contacting the cell at least once with an effective amount of naphthyridine-azaquinolone (NA),
   thereby inhibiting the expansion or inducing the contraction of a repeat DNA sequence in the cell.

2. The method of claim 1, wherein the contacting is in vivo and comprises administering the NA to an individual.

3. The method of claim 1, wherein the contacting step is performed a plurality of times.

4. The method of claim 1, further comprising, prior to the contacting step, determining the number of repeats within the repeat DNA sequence.

5. The method of claim 1, further comprising, after the contacting step, determining the number of repeats within the repeat DNA sequence.

6. The method of claim 1, wherein the cells are contacted with an amount of NA that is dependent on the number of repeats within the repeat DNA sequence.

7. The method of claim 1, wherein the NA is modified.

* * * * *

SEQUENCE LISTING

<160> NUMBER OF SEQ ID NOS: 23

<210> SEQ ID NO 1
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 1
accctagaac tgtcttcgac tcc                                          23

<210> SEQ ID NO 2
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 2
ttcccgagta agcaggcaga g                                            21

<210> SEQ ID NO 3
<211> LENGTH: 20
<212> TYPE: DNA
<213> ORGANISM: Artificial Sequence
<220> FEATURE:
<223> OTHER INFORMATION: synthetically generated oligonucleotide -continued

<400> SEQUENCE: 3
gcccagagcc ccattcattg                                              20

<210> SEQ ID NO 4
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 4
aggaagctga ggaggcggcg g                                            21

<210> SEQ ID NO 5
<211> LENGTH: 30
<212> TYPE: DNA
<213> ORGANISM: Artificial Sequence
<220> FEATURE:
<223> OTHER INFORMATION: synthetically generated oligonucleotide

<400> SEQUENCE: 5
atgaaggcct tcgagtccct caagtccttc                                   30

<210> SEQ ID NO 6
<211> LENGTH: 18
<212> TYPE: DNA
<213> ORGANISM: Artificial Sequence
<220> FEATURE:
<223> OTHER INFORMATION: synthetically generated oligonucleotide

<400> SEQUENCE: 6
cggcggtggc ggctgttg                                                18

<210> SEQ ID NO 7
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 7
ttcagtacat tgctgctgct g                                            21

<210> SEQ ID NO 8
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 8
aaaaaggttc tgctgatgga a                                            21

<210> SEQ ID NO 9
<211> LENGTH: 30
<212> TYPE: DNA
<213> ORGANISM: Artificial Sequence
<220> FEATURE:
<223> OTHER INFORMATION: synthetically generated oligonucleotide

<400> SEQUENCE: 9
tttgagaaag gcttgtgagg actgagaatg                                   30

<210> SEQ ID NO 10

```
<211> LENGTH: 26
<212> TYPE: DNA
<213> ORGANISM: Artificial Sequence
<220> FEATURE:
<223> OTHER INFORMATION: synthetically generated oligonucleotide

<400> SEQUENCE: 10
ggtccttcat gttagaaaac ctggct                                          26

<210> SEQ ID NO 11
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 11
ccttcgagtc cctcaagtcc ttc                                             23

<210> SEQ ID NO 12
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 12
ggcggcggtg gcggctgttg                                                 20

<210> SEQ ID NO 13
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 13
ggaagaatca aatagacaat                                                 20

<210> SEQ ID NO 14
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 14
gctggccata tatatttta aacc                                             24

<210> SEQ ID NO 15
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 15
ctctgaccta tctccaatcc tc                                              22

<210> SEQ ID NO 16
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 16
```
tctccttctc cctgattcag                                               20

<210> SEQ ID NO 17
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 17
taggtcataa atgatctgct gc                                            22

<210> SEQ ID NO 18
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 18
atgataatct ctcaatgacc c                                             21

<210> SEQ ID NO 19
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 19
tgggattaca cgtgtgaacc aacc                                          24

<210> SEQ ID NO 20
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 20
tgtgacacag gcagactgtg gatc                                          24

<210> SEQ ID NO 21
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 21
agagaatagg aacttcggaa tagg                                          24

<210> SEQ ID NO 22
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 22
ccatgttcat gccttcttct tt                                            22

<210> SEQ ID NO 23
<211> LENGTH: 24
<212> TYPE: DNA

```
<213> ORGANISM: Artificial Sequence
<220> FEATURE:
<223> OTHER INFORMATION: synthetically generated oligonucleotide

<400> SEQUENCE: 23
acagcacaat aaccagcacg ttgc                                      24
```